US009598487B2

(12) United States Patent
Borras et al.

(10) Patent No.: US 9,598,487 B2
(45) Date of Patent: Mar. 21, 2017

(54) STABLE AND SOLUBLE ANTIBODIES

(71) Applicant: ESBATech, An Alcon Biomedical Research Unit LLC, Fort Worth, TX (US)

(72) Inventors: Leonardo Jose Borras, Schlieren (CH); David Urech, Hombrechtikon (CH)

(73) Assignee: ESBATech, an Alcon Biomedical Unit LLC, Zurich-Schlieren (CH)

( * ) Notice: Subject to any disclaimer, the term of this patent is extended or adjusted under 35 U.S.C. 154(b) by 0 days.

(21) Appl. No.: 14/011,831

(22) Filed: Aug. 28, 2013

(65) Prior Publication Data

US 2013/0344086 A1 Dec. 26, 2013

Related U.S. Application Data

(62) Division of application No. 13/278,500, filed on Oct. 21, 2011, now Pat. No. 8,545,849.

(60) Provisional application No. 61/405,798, filed on Oct. 22, 2010, provisional application No. 61/484,749, filed on May 11, 2011.

(51) Int. Cl.
  *A61K 39/35* (2006.01)
  *C07K 16/00* (2006.01)
  *C12N 5/16* (2006.01)
  *C07K 16/24* (2006.01)

(52) U.S. Cl.
  CPC ........ *C07K 16/241* (2013.01); *C07K 2317/24* (2013.01); *C07K 2317/94* (2013.01)

(58) Field of Classification Search
  None
  See application file for complete search history.

(56) References Cited

U.S. PATENT DOCUMENTS

| | | | |
|---|---|---|---|
| 4,275,149 A | 6/1981 | Litman et al. | |
| 4,318,980 A | 3/1982 | Bogulaski et al. | |
| 4,376,110 A | 3/1983 | David et al. | |
| 4,737,456 A | 4/1988 | Weng et al. | |
| 4,881,175 A | 11/1989 | Ladner | |
| 4,946,778 A | 8/1990 | Ladner et al. | |
| 5,013,653 A | 5/1991 | Huston et al. | |
| 5,091,513 A | 2/1992 | Huston et al. | |
| 5,132,405 A | 7/1992 | Huston | |
| 5,258,498 A | 11/1993 | Huston et al. | |
| 5,260,203 A | 11/1993 | Ladner et al. | |
| 5,455,030 A | 10/1995 | Ladner et al. | |
| 5,476,786 A | 12/1995 | Huston | |
| 5,482,858 A | 1/1996 | Huston et al. | |
| 5,854,027 A | 12/1998 | Steipe et al. | |
| 6,300,064 B1 | 10/2001 | Knappik et al. | |
| 6,815,540 B1 | 11/2004 | Pluckthun | |
| 7,431,927 B2 | 10/2008 | Couto et al. | |
| 2004/0132028 A1 | 7/2004 | Stumpp et al. | |
| 2011/0152505 A1 | 6/2011 | Urech et al. | |
| 2011/0159007 A1 | 6/2011 | Borras et al. | 424/158.1 |

FOREIGN PATENT DOCUMENTS

| | | |
|---|---|---|
| WO | 8906692 | 7/1989 |
| WO | 9101753 | 2/1991 |
| WO | 9729131 | 8/1997 |
| WO | 0194585 | 12/2001 |
| WO | WO2007/109254 | 9/2007 |
| WO | 2008004834 A1 | 1/2008 |
| WO | 2009000099 | 12/2008 |
| WO | 2009000099 A2 | 12/2008 |
| WO | 2009155723 | 12/2009 |
| WO | 2009155723 A2 | 12/2009 |
| WO | 2009155724 A2 | 12/2009 |
| WO | 2009155725 A1 | 12/2009 |
| WO | WO 2009155723 A2 | 12/2009 |
| WO | 2010003268 A2 | 1/2010 |
| WO | 2010006454 A2 | 1/2010 |

OTHER PUBLICATIONS

Foster et al. Efficacy of etanercept in preventing relapse of uveitis controlled by methotrexate. Archive of Ophthalmology. 2003; 121(4):437-440.*
Hale and Lightman. Anti-TNF therapeis in the management of acute and chronic uveitis. 2006, Cytokine; 33:231-237).*
Foster et al. Efficacy of etanercept in preventing relapse of uveitis controlled by methotrexate. Archive of Ophthalmology. 2003; 121 (4):437-440.*
Tynjala et al. Adalimumab in juvenile idiopathic arthritis-associated chronic anterior uveitis. Rheumatology. 2008; 47:339-344.*
Kasner et al. The paradoxical effect of tumor necrosis factor alpha (TNF-alpha) in endotoxin-induced uveitis. Investigative Ophthalmology and Visual Science. 1993; 34(10):2911-2917.*
Wendling et al. New onset of uveitis under anti-TNF therapy. Arthritis and Rheumatism. 2010; 62 Supplement 10: 904.*
Ottiger et al. (Investigative Ophthalmology & Visual Science, 2009, 50(2): 779-786).*
Androudi et al. (Ophthalmology 2010;117:1612-1616).*
Furrer et al. (Investigative Ophthalmology & Visual Science, 2009, 50(2):771-778).*
Borras et al.; "Generic approach for the generation of stable humanized single-chain Fv fragments from rabbit monoclonal antibodies"; The Journal of Biologicai Chemistry; vol. 285; No. 12; pp. 9054-9066 (Mar. 19, 2010).

(Continued)

*Primary Examiner* — Vanessa L Ford
*Assistant Examiner* — Sandra Dillahunt
(74) *Attorney, Agent, or Firm* — Jason J. Derry

(57) ABSTRACT

The invention provides antibodies that are modified to reduce aggregration propensity, and methods of producing such antibodies. The present invention also provides particularly stable and soluble scFv antibodies and Fab fragments specific for TNF, which comprise specific light chain and heavy chain sequences that are optimized for stability, solubility, in vitro and in vivo binding of TNF, and low immunogenicity. The nucleic acids, vectors and host cells for expression of the recombinant antibodies of the invention, methods for isolating them and the use of said antibodies in medicine are also disclosed.

5 Claims, 9 Drawing Sheets

(56) References Cited

OTHER PUBLICATIONS

Honegger et al.: "Yet another numbering scheme for immunoglobulin variable domains: An automatic modeling and analysis tool"; Journal of Molecular Biology; vol. 309; No. 3; pp. 657-670 (Jun. 8, 2001).
Alfthan, et al., "Properties of a Single-Chain Antibody Containing Different Linker Peptides," Protein Engineering, 1995, pp. 725-731, vol. 8, No. 7.
Beutler et al.; "Cachectin and tumour necrosis factor as two sides of the same biological coin"; Review Article; Nature; vol. 320; pp. 584-588 (Apr. 17, 1986).
Brennan et al.; "Preparation of bispecific antibodies by chemical recombination of monoclonal immunoglobulin G1 fragments"; Science; vol. 229; pp. 81-83 (1985).
Burks et al.; "In vitro scanning saturation mutagenesis of an antibody binding pocket"; Proc. Natl. Acad. Sci.; vol. 94; pp. 412-417 (Jan. 1997).
Calandra et al.; "Prognostic values of tumor necrosis factor/cachectin, interleukin-1, interferon-alpha, and interferon-y in the serum of patients with septic shock"; Journal of Infectious Diseases; vol. 161; pp; 982-987 (1990).
Choi et al.; "Recombinant chimeric OKT3 scFv IgM antibodies mediate immune suppression while reducing T cell activation in vitro"; Eur. J. Immunol.; vol. 31; pp. 94-106 (2001).
Cornette et al; "Hydrophobicity scales and computational techniques for detecting amphipathic stuctures in proteins"; J. Mol. Biol., vol. 195; pp. 659-685 (1987).
Debets et al.; "Plasma tumor necrosis factor and mortality in critically ill septic patients"; Critical Care Medicine; vol. 17; No. 6; pp. 489-494 (Jun. 1989).
Glennie et al.; "Preparation and performance of bispecific F(ab'y)2 antibody containing thioether-linked Fab'y fragments"; The Journal of Immunology; vol. 139; No. 7; pp. 2367-2375 (Oct. 1, 1987).
Holliger et al; "'Diabodies': Small bivalent and bispecific antibody fragments"; Proc. Natl. Acad. Sci.; vol. 90; pp. 6444-6448 (Jul. 1993).
Honegger and Pluckthun; "Yet another numbering scheme for immunoglobulin variable domains: an automatic modeling and analysis tool"; J. Mol. Biol.; vol. 309; pp. 657-670 (2001).
Hu et al.; "Minibody: a novel engineered anti-carcinoembryonic antigen antibody fragment (single-chain Fv-CH3) which exhibits rapid, high-level targeting of xenografts"; Cancer Research; vol. 56; pp. 3055-3061 (Jul. 1, 1996).
Keffer et al; Transgenic mice expressing human tumour necrosis factor: a predictive genetic model of arthritis; The EMBO Journal; vol. 10; No. 13; pp. 4025-4031 (1991).
Kipriyanov et al; "Bispecifc tandem diabody for tumor therapy with improved antigen binding and pharmacokinetics"; J. Mol. Biol.; vol. 293; pp. 41-56 (1999).
Smith and Baglioni; "The active form of tumor necrosis factor is a trimer"; Communicaton; The Jounal of Biological Chemistry: vol. 262; No. 15; pp. 6951-6954 (May 25, 1987).
Tisdale; "Cancer cachexia"; Langenbecks Arch. Surg.; vol. 389; pp. 299-395 (2004).
Sarah Hale, et al.; "Anti-TNF therapies in the management of acute and chronic uveitis"; Department of Clinical Ophthalmology, Institute of Ophthalmology and Moorfields Eye Hospital; Elsevier (www.elsevier.com/locate/issn/10434666); Dec. 7, 2005; pp. 231-237.
Sartani et al. 1996, Invest Ophthalmol Vis Sci. 37:2211-2218.
Dick et al. 1996, Eur. J. Immunol. 26: 1018-1025.
Dick et al. 1998, Journal of Autoimmunity 11: 255-264.
Hankey et al. 2001, Exp. Eye Res. 72, 341-350.
Robertson et al. 2003, Invest Ophthalmol Vis Sci. 44: 3034-3041.
Santos-Lacomba et al. 2001, Ophthalmic Res 33:251-255.
Smith et al. 1998, Immunology and Cell Biology 76, 497-512.
Koizumi et al. 2003, Invest Ophthalmol Vis Sci. 44: 2184-2191.
Avunduk et al., 2004, Exp. Eye Res. 79: 357-365.
Rosenbaum et al. 1993, Regional Immunology 5: 299-303.
Sfikakis et al. 2001, Lancet 358, 295-296.
Sfikakis et al., 2004; Annals of Internal Medicine 140, 404-406.
Braun et al. 2005, Arthritis & Rheumatism, 52, 2447-2451.
Sobrin et al. 2007, Arch Ophthalmol. 2007;125(7):895-900.
Rudwaleit et al. 2009, Ann Rheum Dis 2009, 68:696-701.
Cordero-Coma et al. 2011, Ophthalmology 118: 1892.e3-4.
Williams et al. 2012, J Ophthal Inflamm Infect 2: 231-233.
Dobner et al., 2013, Br. J. Ophthalmol. 97:134-138.
Levy-Clarke et al., 2014 Ophthalmology 121:785-796.
Wendling et al, 2011, Semin Arthritis Rheum 41:503-510.
Mo et al, 1998, Exp Eye Res. 66:547-557.
Alfthan et al., "Properties of a Single-Chain Amtibody Containing Different Linker Peptides," Protein Engineering, 1995, pp. 725-731, vol. 8, No. 7.
Beutler et al.; "Cachectin and tumor necrosis factotr as two sides of the same biological coin"; Review Article; Nature; vol. 320 pp. 584-588 (Apr. 17, 1986).
Bird et al.; "Single-chain antigen-binding proteins"; Science; vol. 242; pp. 423-426 (Oct. 21, 1988).
Brennan et al.; "Preparation of bispecific antibodies by chemical recombination of monoclonal immunoglobulin G1 fragments"; Science; vol. 229 pp. 81-83 (1985).
Brummell et al.; "Probing the combining site of an anti-carbohydrate antibody by saturation-mutagenesis: role of the heavy-chain CDR3 residues"; Biochemistry; vol. 32; pp. 1180-1187 (1993).
Burks et al. "In vitro scanning saturation mutagenesis of an antibody binding pocket"; Proc. Natl. Acad. Sci.; vol. 94; pp. 412-417 (Jan. 1997).
Calandra et al.; "Prognostic values of tumor necrosis factor/cachectin, interleukin-1, interferon-alpha, and interferon-y in the serum of patients with septic shock"; Journal of Infectious Diseases; vol. 161; pp. 982-987 (1990).
Cerami and Beutler; "The role of cachectin/TNF in endotoxic shock and cachexia"; Immunology Today; vol. 9; No. 1; pp. 28-31 (1988).
Choi et al.; Recombinant chimeric OKT3 scFv IgM anibodies mediate immune suppression while reducing T cell acitviation in vitro; Eur. J. Immunol; vol. 31; pp. 94-106 (2001).
Cornette et al.; "Hydrophobicity scales and computational techniques for detecting amphipathic structures in proteins": J. Mol. Biol., vol. 195; pp. 659-685 (1987).
Debets et al.; "Plasma tumor necrosis factor and mortality in critically ill septic patients"; Critical Care Medicine; vol. 17: No. 6; pp. 489-494 (Jun. 1989).
Feldmann et al.; "Anti-tumor necrosis factor-alpha therapy of rheumatoid arthritis"; Advances in Immunology; vol. 64; pp. 283-350, 1997.
Glennie et al.; "Preparation and performance of bispecific F(ab'y)2 antibody containing thioether-linked Faby'y fragments"; The Journal of Immunology; vol. 139; No. 7; pp. 2367-2375 (Oct. 1, 1987).
Grell et al.; "The transmembrane form of tumor necrosis factor is the prime activating ligand of the 80 kDa tumor necrosis factor receptor"; vol. 83; pp. 793-802; (Dec. 1, 1995).
Holliger et al; "'Diabodies'; Small bivalent and bispecific antibody fragments"; Proc. Natl. Acad. Sci.; vol. 90; pp. 6444-6448 (Jul. 1993).
Honegger and Pluckthun; "Yet another numbering scheme for immunoglobulin variable domains; an automatic modeling and analysis tool"; J. Moi. Biol.; vol. 309; pp. 657-670 (2001).
Hu et al; "Minibody; a novel engineered anti-carcinoembryonic antigen antibody fragment (single-chain Fv-CH3) which exhibits rapid, high-level tageting of xenograftis"; Cancer Research; vol. 56; pp. 3055-3061 (Jul. 1, 1996).
Huston et al.; "Protein engineering of antibody binding sites: recovery of specific activity in an anti-digoxin single-chain Fv analogue produced in *Escherichia coli*"; Proc. Natl. Acad. Sci.; vol. 85; pp. 5879-5883 (Aug. 1988).
Karpovsky et al.; "Production of target-specific effect or cells using hetero-cross-linked aggregates containing anti-target cell and anti-Fcy receptor antibodies"; Journal of Experimental Medicine; vol. 160; pp. 1686-1701 (Dec. 1984).
Keffer et al; Transgenic mice expressing human tumour necrosis factor: a predictive genetic model of arthritis; The EMBO Journal; vol. 10; No. 13; pp. 4025-4031 (1991).

(56) References Cited

OTHER PUBLICATIONS

Kipriyanov et al; "Bispecific tandem diabody for tumor therapy with improved antigen binding and pharmacokinetics"; J. Mol. Biol.; vol. 293; pp. 41-56 (1999).
Kobayashi et al; "Tryptophan H33 plays an important role in pyrimidine (6-4) pyrimidone photoproduct binding by a high-affinity antibody"; Protein Engineering; vol. 12; No. 10; pp. 879-884 (1999).
Kriegler et al.; "A novel form of TNF/cachectin is a cell surface cytotoxic transmembrane Protein: ramifications for the complex physiology of TNF;" Cell; vol. 53; pp. 45-53 (Apr. 8, 1988).
Liu et al.; "Heteroantibody duplexes target cells for lysis by cytotoxic T lymphocytes"; Proc. Natl. Acad. Sci.; vol. 82; pp. 8648-8652 (Dec. 1985).
McKnown et al.; Lack of efficacy of oral bovine type II collagen added to existing therapy in rheumatoid arthritis; Arthritis & Rheumatism; vol. 32; pp. 1204-1208 (Jun. 6, 1999).
Myers and Miller; "Optimal alignments in linear space"; CABIOS; vol. 4; No. 1; pp. 11-17 (1988).
Michie et al.; "Tumour necrosis factor and bacterial sepsis"; Br. J. Surg.; vol. 76; pp. 670-671 (Jul. 1989).
Needleman and Wunsch; "A general method applicable to the search for similarities in the amino acid sequence of two proteins"; J. Mol. Biol.; vol. 48; pp. 443-453 (1970).
Old; Tumor Necrosis Factor (TNF); Science; vol. 230; pp. 630-632 (1986).
Paulus; "Preparation and biomedical applications for bispecific antibodies"; Behring Inst. Mitt.; No. 78; pp. 118-132 (1985).
Revhaug et al.; "Inhibition of cyclo-oxygenase attenuates the metabolic response to endotoxin in humans"; Arch. Surg.; vol. 123; pp. 162-170 (Feb. 1988).
Roovers and Van Der Linden; "In vitro characterization of a monovalent and bivalent form of a fully human anti-Ep-CAM phage antibody"; Cancer Immunol. Immunother; vol. 50; pp. 51-59 (2001).
Rose et al.; "Hydrophobicity of amino acid residues in globular proteins"; Science; vol. 229; pp. 834-838 (1985).
Simpson and Casey; "Role of tumor necrosis factor in sepsis and acute lung injury"; Septic Shock; Critical Care Clinics; vol. 5; No. 1; pp. 27-47 (Jan. 1989).
Smith and Baglioni; "The active form of tumor necrosis factor is a timer"; Communication; The Journal of Biological Chemistry; vol. 262; No. 15; pp. 6951-6954 (May 25, 1987).
Tisdale; "Cancer cachexia"; Langenbecks Arch. Surg.; vol. 389; pp. 299-305 (2004).
Waage et al.; "Association between tumour necrosis factorin serum and fatal outcome in patients with meningococcal disease"; The Lancet; vol. 1; pp. 355-357 (Feb. 14, 1987).

Ward et al; "Binding activities of a repertoire of single immunoglobulin variable domains secreted form *Escherichia coli*"; Letters to Nature; vol. 341; pp. 544-546 (Oct. 12, 1989).
Baynes et al; "Role of arginine in the stabilization of proteins against aggregation"; Biochemistry; vol. 44; No. 12; pp. 4919-4925 (Mar. 29, 2005).
Kristoffer et al; "Thermodynamically stable aggregation-resistant antibody domains through directed evolution"; Journal of Molecular Biology; vol. 376; No. 4; pp. 926-931 (Feb. 29, 2008).
Borras et al.; "Generic approach for the generation of stable humanized single-chain Fv fragments from rabbit monoclonal antibodies"; The Journal of Biological Chemistry; vol. 285; No. 12; pp. 9054-9066 (Mar. 19, 2010).
Ewert et al.; "Stability improvement of antibodies for extracellular and intracellular applications: CDR grafting to stable frameworks and structure-based frameworks and structure-based framework engineering"; Methods; vol. 34; No. 2; pp. 184-199 (Oct. 2004).
Honegger et al.; "Yet another numbering scheme for immunoglobulin variable domains: An automatic modeling and analysis tool"; Journal of Molecular Biology; vol. 309; No. 3; pp. 657-670 (Jun. 8, 2001).
Worn et al.; "Stability engineering of antibody single-chain Fv fragments"; Journal of Molecular Biology; vol. 305; No. 5; pp. 989-1010 (Feb. 2, 2001).
Search Report and Written Opinion corresponding to PCT application serial No. PCT/CH2011/000256 dated Feb. 9, 2012.
Pakula et al.; "Genetic Analysis of Protein Stability and Function"; Annu. Rev. Genet.; 1989; vol. 23; pp. 289-310 (www.annualreviews.org).
Rajagopalan et al.; "Comparing the Discriminative Validity of Two Generic and One Disease-Specific Health-Related Quality of Life Measures in a Sample of Patients with Dry Eye"; Value in Health; Vo. 8; No. 2; 2005; pp. 168-174.
Gall, et al., "Effect of linker sequences between the antibody variable domains on the formation, stability and biological activity of a bispecific tandem diabody:", Protein Engineering, Design & Selections, 2004, vol. 17, No. 4, pp. 357-366.
Tan, et al., "Contributions of a Highly Conserved VH/VL Hydrogen Bonding Interaction to scFv Folding Stability and Refolding Efficiency" Biophys. J., 1998, vol. 75, pp. 1473-1482.
Borras, Leonardo, Prosecution History, U.S. Appl. No. 14/134,779, filed Dec. 19, 2013, 772 pages.
Miller et al., "Stability engineering of scFvs for the development of bispecific and multivalent antibodies", Protein Engineering, Design & Selection, 2010, vol. 23, No. 7, pp. 549-557.
Suarez et al., "PROTDES: CHARMM toolbox for computational protein design", Syst. Synth. Biol., 2008, vol. 2, pp. 105-113.
Narayanan et al., "Energy-based analysis and prediction of the orientation between light- and heavy-chain antibody variable domains", Journal of Molecular Biology, 2009, vol. 388, pp. 941-953.

* cited by examiner

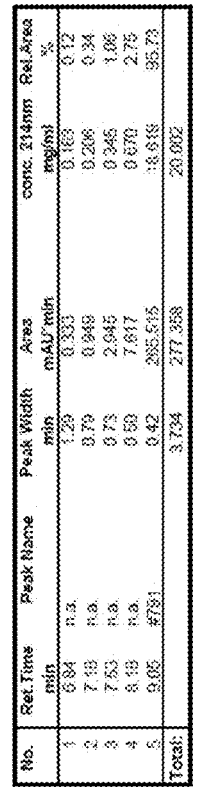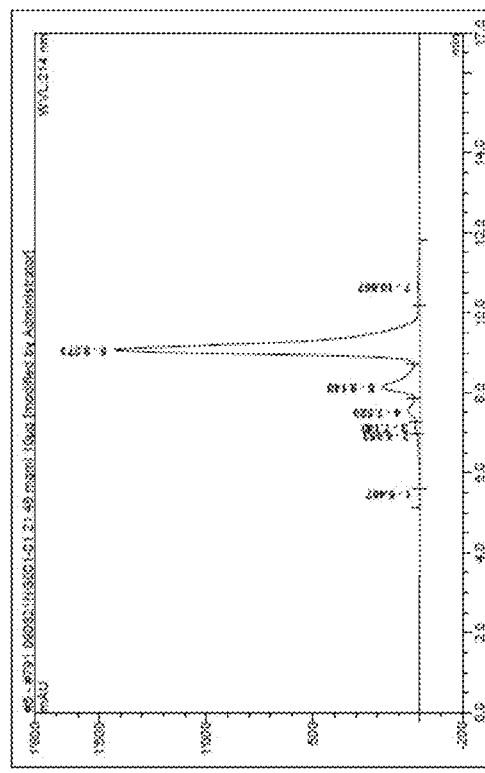
FIG. 7B
FIG. 7A

SEQUENCE LISTING

<160> NUMBER OF SEQ ID NOS: 18

<210> SEQ ID NO 1
<211> LENGTH: 231
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (24)..(73)
<223> OTHER INFORMATION: X can be any naturally occurring amino acid.
      at least one and up to 50 amino acids can be present
<220> FEATURE:
<221> NAME/KEY: MISC_FEATURE
<222> LOCATION: (89)..(138)
<223> OTHER INFORMATION: X can be any naturally occurring amino acid.
      at least one and up to 50 amino acids can be present
<220> FEATURE:
<221> NAME/KEY: MISC_FEATURE
<222> LOCATION: (171)..(220)
<223> OTHER INFORMATION: X can be any naturally occurring amino acid.
      at least one and up to 50 amino acids can be present

<400> SEQUENCE: 1

Glu Ile Val Met Thr Gln Ser Pro Ser Thr Leu Ser Ala Ser Val Gly
1               5                   10                  15

Asp Arg Val Ile Ile Thr Cys Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Trp Tyr Gln Gln Lys Pro Gly
65                  70                  75                  80

Arg Ala Pro Lys Leu Leu Ile Tyr Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Gly Val Pro Ser Arg Phe
    130                 135                 140

Ser Gly Ser Gly Ser Gly Ala Glu Phe Thr Leu Thr Ile Ser Ser Leu
145                 150                 155                 160

Gln Pro Asp Asp Phe Ala Thr Tyr Tyr Cys Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Phe Gly Gln Gly
    210                 215                 220

Thr Lys Leu Thr Val Leu Gly
225                 230

<210> SEQ ID NO 2
<211> LENGTH: 112
<212> TYPE: PRT
<213> ORGANISM: Artificial
<220> FEATURE:
<223> OTHER INFORMATION: Synthetic Peptide

```
<400> SEQUENCE: 2

Glu Ile Val Met Thr Gln Ser Pro Ser Thr Leu Ser Ala Ser Val Gly
1               5                   10                  15

Asp Arg Val Ile Ile Thr Cys Gln Ser Ser Gln Ser Val Tyr Gly Asn
            20                  25                  30

Ile Trp Met Ala Trp Tyr Gln Gln Lys Pro Gly Arg Ala Pro Lys Leu
        35                  40                  45

Leu Ile Tyr Gln Ala Ser Lys Leu Ala Ser Gly Val Pro Ser Arg Phe
    50                  55                  60

Ser Gly Ser Gly Ser Gly Ala Glu Phe Thr Leu Thr Ile Ser Ser Leu
65                  70                  75                  80

Gln Pro Asp Asp Phe Ala Thr Tyr Tyr Cys Gln Gly Asn Phe Asn Thr
                85                  90                  95

Gly Asp Arg Tyr Ala Phe Gly Gln Gly Thr Lys Leu Thr Val Leu Gly
            100                 105                 110

<210> SEQ ID NO 3
<211> LENGTH: 232
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (26)..(75)
<223> OTHER INFORMATION: X can be any naturally occurring amino acid.
      at least one and up to 50 amino acids can be present
<220> FEATURE:
<221> NAME/KEY: MISC_FEATURE
<222> LOCATION: (90)..(139)
<223> OTHER INFORMATION: X can be any naturally occurring amino acid.
      at least one and up to 50 amino acids can be present
<220> FEATURE:
<221> NAME/KEY: MISC_FEATURE
<222> LOCATION: (172)..(221)
<223> OTHER INFORMATION: X can be any naturally occurring amino acid.
      at least one and up to 50 amino acids can be present

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Thr Ala Ser Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Trp Val Arg Gln Ala
65                  70                  75                  80

Pro Gly Lys Gly Leu Glu Trp Val Gly Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Arg Phe Thr Ile Ser
    130                 135                 140

Arg Asp Thr Ser Lys Asn Thr Val Tyr Leu Gln Met Asn Ser Leu Arg
145                 150                 155                 160
```

```
Ala Glu Asp Thr Ala Val Tyr Tyr Cys Ala Arg Xaa Xaa Xaa Xaa
            165                 170                 175

Xaa Xaa Xaa Xaa Xaa Xaa Xaa Xaa Xaa Xaa Xaa Xaa Xaa Xaa Xaa
        180                 185                 190

Xaa Xaa Xaa Xaa Xaa Xaa Xaa Xaa Xaa Xaa Xaa Xaa Xaa Xaa Xaa
    195                 200                 205

Xaa Xaa Xaa Xaa Xaa Xaa Xaa Xaa Xaa Xaa Xaa Xaa Trp Gly Gln
    210                 215                 220

Gly Thr Leu Val Thr Val Ser Ser
225                 230

<210> SEQ ID NO 4
<211> LENGTH: 232
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (26)..(75)
<223> OTHER INFORMATION: X can be any naturally occurring amino acid.
      at least one and up to 50 amino acids can be present
<220> FEATURE:
<221> NAME/KEY: MISC_FEATURE
<222> LOCATION: (90)..(139)
<223> OTHER INFORMATION: X can be any naturally occurring amino acid.
      at least one and up to 50 amino acids can be present
<220> FEATURE:
<221> NAME/KEY: MISC_FEATURE
<222> LOCATION: (172)..(221)
<223> OTHER INFORMATION: X can be any naturally occurring amino acid.
      at least one and up to 50 amino acids can be present

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Thr Val Ser Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Trp Val Arg Gln Ala
65                  70                  75                  80

Pro Gly Lys Gly Leu Glu Trp Val Gly Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
        100                 105                 110

Xaa Xaa Xaa Xaa Xaa Xaa Xaa Xaa Xaa Xaa Xaa Xaa Xaa Xaa Xaa
    115                 120                 125

Xaa Xaa Xaa Xaa Xaa Xaa Xaa Xaa Xaa Xaa Arg Phe Thr Ile Ser
    130                 135                 140

Lys Asp Thr Ser Lys Asn Thr Val Tyr Leu Gln Met Asn Ser Leu Arg
145                 150                 155                 160

Ala Glu Asp Thr Ala Val Tyr Tyr Cys Ala Arg Xaa Xaa Xaa Xaa
            165                 170                 175

Xaa Xaa Xaa Xaa Xaa Xaa Xaa Xaa Xaa Xaa Xaa Xaa Xaa Xaa Xaa
        180                 185                 190

Xaa Xaa Xaa Xaa Xaa Xaa Xaa Xaa Xaa Xaa Xaa Xaa Xaa Xaa Xaa
    195                 200                 205
```

Xaa Xaa Xaa Xaa Xaa Xaa Xaa Xaa Xaa Xaa Xaa Trp Gly Gln
    210                 215                 220

Gly Thr Leu Val Thr Val Ser Ser
225                 230

<210> SEQ ID NO 5
<211> LENGTH: 121
<212> TYPE: PRT
<213> ORGANISM: Artificial
<220> FEATURE:
<223> OTHER INFORMATION: Synthetic Peptide

<400> SEQUENCE: 5

Glu Val Gln Leu Val Glu Ser Gly Gly Gly Ser Val Gln Pro Gly Gly
1               5                   10                  15

Ser Leu Arg Leu Ser Cys Thr Ala Ser Gly Phe Thr Ile Ser Arg Ser
            20                  25                  30

Tyr Trp Ile Cys Trp Val Arg Gln Ala Pro Gly Lys Gly Leu Glu Trp
        35                  40                  45

Val Gly Cys Ile Tyr Gly Asp Asn Asp Ile Thr Pro Leu Tyr Ala Asn
    50                  55                  60

Trp Ala Lys Gly Arg Phe Thr Ile Ser Arg Asp Thr Ser Lys Asn Thr
65                  70                  75                  80

Val Tyr Leu Gln Met Asn Ser Leu Arg Ala Glu Asp Thr Ala Thr Tyr
                85                  90                  95

Tyr Cys Ala Arg Leu Gly Tyr Ala Asp Tyr Ala Tyr Asp Leu Trp Gly
            100                 105                 110

Gln Gly Thr Thr Val Thr Val Ser Ser
        115                 120

<210> SEQ ID NO 6
<211> LENGTH: 5
<212> TYPE: PRT
<213> ORGANISM: Artificial
<220> FEATURE:
<223> OTHER INFORMATION: Synthetic Peptide

<400> SEQUENCE: 6

Gly Gly Gly Gly Ser
1               5

<210> SEQ ID NO 7
<211> LENGTH: 20
<212> TYPE: PRT
<213> ORGANISM: Artificial
<220> FEATURE:
<223> OTHER INFORMATION: Synthetic Peptide

<400> SEQUENCE: 7

Gly Gly Gly Gly Ser Gly Gly Gly Ser Gly Gly Gly Gly Ser Gly
1               5                   10                  15

Gly Gly Gly Ser
            20

<210> SEQ ID NO 8
<211> LENGTH: 483
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (24)..(73)

```
<223> OTHER INFORMATION: X can be any naturally occurring amino acid.
      at least one and up to 50 amino acids can be present
<220> FEATURE:
<221> NAME/KEY: MISC_FEATURE
<222> LOCATION: (89)..(138)
<223> OTHER INFORMATION: X can be any naturally occurring amino acid.
      at least one and up to 50 amino acids can be present
<220> FEATURE:
<221> NAME/KEY: MISC_FEATURE
<222> LOCATION: (171)..(220)
<223> OTHER INFORMATION: X can be any naturally occurring amino acid.
      at least one and up to 50 amino acids can be present
<220> FEATURE:
<221> NAME/KEY: MISC_FEATURE
<222> LOCATION: (277)..(326)
<223> OTHER INFORMATION: X can be any naturally occurring amino acid.
      at least one and up to 50 amino acids can be present
<220> FEATURE:
<221> NAME/KEY: MISC_FEATURE
<222> LOCATION: (341)..(390)
<223> OTHER INFORMATION: X can be any naturally occurring amino acid.
      at least one and up to 50 amino acids can be present
<220> FEATURE:
<221> NAME/KEY: MISC_FEATURE
<222> LOCATION: (423)..(483)
<223> OTHER INFORMATION: X can be any naturally occurring amino acid.
      at least one and up to 50 amino acids can be present

<400> SEQUENCE: 8

Glu Ile Val Met Thr Gln Ser Pro Ser Thr Leu Ser Ala Ser Val Gly
1               5                   10                  15

Asp Arg Val Ile Ile Thr Cys Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Trp Tyr Gln Gln Lys Pro Gly
65                  70                  75                  80

Arg Ala Pro Lys Leu Leu Ile Tyr Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Gly Val Pro Ser Arg Phe
    130                 135                 140

Ser Gly Ser Gly Ser Gly Thr Glu Phe Thr Leu Thr Ile Ser Ser Leu
145                 150                 155                 160

Gln Pro Asp Asp Phe Ala Thr Tyr Tyr Cys Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Phe Gly Gln Gly
    210                 215                 220

Thr Lys Leu Thr Val Leu Gly Gly Gly Gly Ser Gly Gly Gly Gly
225                 230                 235                 240

Ser Gly Gly Gly Gly Ser Gly Gly Gly Ser Glu Val Gln Leu Val
                245                 250                 255

Glu Ser Gly Gly Gly Leu Val Gln Pro Gly Gly Ser Leu Arg Leu Ser
```

```
                260                 265                 270
Cys Thr Ala Ser Xaa Xaa Xaa Xaa Xaa Xaa Xaa Xaa Xaa Xaa
            275                 280                 285

Xaa Xaa Xaa Xaa Xaa Xaa Xaa Xaa Xaa Xaa Xaa Xaa Xaa Xaa
        290                 295                 300

Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Trp Val Arg Gln Ala Pro Gly Lys Gly Leu
                325                 330                 335

Glu Trp Val Gly Xaa Xaa Xaa Xaa Xaa Xaa Xaa Xaa Xaa Xaa
            340                 345                 350

Xaa Xaa Xaa Xaa Xaa Xaa Xaa Xaa Xaa Xaa Xaa Xaa Xaa Xaa
        355                 360                 365

Xaa Xaa Xaa Xaa Xaa Xaa Xaa Xaa Xaa Xaa Xaa Xaa Xaa Xaa
    370                 375                 380

Xaa Xaa Xaa Xaa Xaa Xaa Arg Phe Thr Ile Ser Arg Asp Thr Ser Lys
385                 390                 395                 400

Asn Thr Val Tyr Leu Gln Met Asn Ser Leu Arg Ala Glu Asp Thr Ala
                405                 410                 415

Val Tyr Tyr Cys Ala Arg Xaa Xaa Xaa Xaa Xaa Xaa Xaa Xaa
            420                 425                 430

Xaa Xaa Xaa Xaa Xaa Xaa Xaa Xaa Xaa Xaa Xaa Xaa Xaa Xaa
        435                 440                 445

Xaa Xaa Xaa Xaa Xaa Xaa Xaa Xaa Xaa Xaa Xaa Xaa Xaa Xaa
    450                 455                 460

Xaa Xaa Xaa Xaa Xaa Xaa Xaa Xaa Trp Gly Gln Gly Thr Leu Val Thr
465                 470                 475                 480

Val Ser Ser

<210> SEQ ID NO 9
<211> LENGTH: 483
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (24)..(73)
<223> OTHER INFORMATION: X can be any naturally occurring amino acid.
      at least one and up to 50 amino acids can be present
<220> FEATURE:
<221> NAME/KEY: MISC_FEATURE
<222> LOCATION: (89)..(138)
<223> OTHER INFORMATION: X can be any naturally occurring amino acid.
      at least one and up to 50 amino acids can be present
<220> FEATURE:
<221> NAME/KEY: MISC_FEATURE
<222> LOCATION: (171)..(220)
<223> OTHER INFORMATION: X can be any naturally occurring amino acid.
      at least one and up to 50 amino acids can be present
<220> FEATURE:
<221> NAME/KEY: MISC_FEATURE
<222> LOCATION: (277)..(326)
<223> OTHER INFORMATION: X can be any naturally occurring amino acid.
      at least one and up to 50 amino acids can be present
<220> FEATURE:
<221> NAME/KEY: MISC_FEATURE
<222> LOCATION: (341)..(390)
<223> OTHER INFORMATION: X can be any naturally occurring amino acid.
      at least one and up to 50 amino acids can be present
<220> FEATURE:
<221> NAME/KEY: MISC_FEATURE
<222> LOCATION: (423)..(483)
<223> OTHER INFORMATION: X can be any naturally occurring amino acid.
``` at least one and up to 50 amino acids can be present

<400> SEQUENCE: 9

Glu Ile Val Met Thr Gln Ser Pro Ser Thr Leu Ser Ala Ser Val Gly
1               5                   10                  15

Asp Arg Val Ile Ile Thr Cys Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Trp Tyr Gln Gln Arg Pro Gly
65                  70                  75                  80

Lys Ala Pro Lys Leu Leu Ile Tyr Xaa Xaa Xaa Xaa Xaa Xaa Xaa
                85                  90                  95

Xaa Xaa Xaa Xaa Xaa Xaa Xaa Xaa Xaa Xaa Xaa Xaa
        100                 105                 110

Xaa Xaa Xaa Xaa Xaa Xaa Xaa Xaa Xaa Xaa Xaa Xaa
    115                 120                 125

Xaa Xaa Xaa Xaa Xaa Xaa Xaa Xaa Xaa Gly Val Pro Ser Arg Phe
130                 135                 140

Ser Gly Ser Gly Ser Gly Thr Glu Phe Thr Leu Thr Ile Ser Ser Leu
145                 150                 155                 160

Gln Pro Asp Asp Phe Ala Thr Tyr Tyr Cys Xaa Xaa Xaa Xaa Xaa
            165                 170                 175

Xaa Xaa Xaa Xaa Xaa Xaa Xaa Xaa Xaa Xaa Xaa Xaa Xaa
        180                 185                 190

Xaa Xaa Xaa Xaa Xaa Xaa Xaa Xaa Xaa Xaa Xaa Xaa Xaa
    195                 200                 205

Xaa Xaa Xaa Xaa Xaa Xaa Xaa Xaa Xaa Xaa Phe Gly Gln Gly
210                 215                 220

Thr Lys Leu Thr Val Leu Gly Gly Gly Gly Ser Gly Gly Gly
225                 230                 235                 240

Ser Gly Gly Gly Gly Ser Gly Gly Gly Ser Glu Val Gln Leu Val
            245                 250                 255

Glu Ser Gly Gly Gly Leu Val Gln Pro Gly Gly Ser Leu Arg Leu Ser
            260                 265                 270

Cys Thr Val Ser Xaa Xaa Xaa Xaa Xaa Xaa Xaa Xaa Xaa
        275                 280                 285

Xaa Xaa Xaa Xaa Xaa Xaa Xaa Xaa Xaa Xaa Xaa Xaa
    290                 295                 300

Xaa Xaa Xaa Xaa Xaa Xaa Xaa Xaa Xaa Xaa Xaa Xaa
305                 310                 315                 320

Xaa Xaa Xaa Xaa Xaa Xaa Trp Val Arg Gln Ala Pro Gly Lys Gly Leu
        325                 330                 335

Glu Trp Val Gly Xaa Xaa Xaa Xaa Xaa Xaa Xaa Xaa Xaa Xaa
            340                 345                 350

Xaa Xaa Xaa Xaa Xaa Xaa Xaa Xaa Xaa Xaa Xaa Xaa
        355                 360                 365

Xaa Xaa Xaa Xaa Xaa Xaa Xaa Xaa Xaa Xaa Xaa Xaa
    370                 375                 380

Xaa Xaa Xaa Xaa Xaa Xaa Arg Phe Thr Ile Ser Lys Asp Thr Ser Lys
385                 390                 395                 400

```
Asn Thr Val Tyr Leu Gln Met Asn Ser Leu Arg Ala Glu Asp Thr Ala
                405                 410                 415

Val Tyr Tyr Cys Ala Arg Xaa Xaa Xaa Xaa Xaa Xaa Xaa Xaa Xaa Xaa
        420                 425                 430

Xaa Xaa Xaa Xaa Xaa Xaa Xaa Xaa Xaa Xaa Xaa Xaa Xaa Xaa Xaa Xaa
        435                 440                 445

Xaa Xaa Xaa Xaa Xaa Xaa Xaa Xaa Xaa Xaa Xaa Xaa Xaa Xaa Xaa Xaa
    450                 455                 460

Xaa Xaa Xaa Xaa Xaa Xaa Xaa Trp Gly Gln Gly Thr Leu Val Thr
465                 470                 475                 480

Val Ser Ser

<210> SEQ ID NO 10
<211> LENGTH: 253
<212> TYPE: PRT
<213> ORGANISM: Artificial
<220> FEATURE:
<223> OTHER INFORMATION: Synthetic Peptide

<400> SEQUENCE: 10

Glu Ile Val Met Thr Gln Ser Pro Ser Thr Leu Ser Ala Ser Val Gly
1               5                   10                  15

Asp Arg Val Ile Ile Thr Cys Gln Ser Ser Gln Ser Val Tyr Gly Asn
            20                  25                  30

Ile Trp Met Ala Trp Tyr Gln Gln Lys Pro Gly Arg Ala Pro Lys Leu
        35                  40                  45

Leu Ile Tyr Gln Ala Ser Lys Leu Ala Ser Gly Val Pro Ser Arg Phe
    50                  55                  60

Ser Gly Ser Gly Ser Gly Ala Glu Phe Thr Leu Thr Ile Ser Ser Leu
65                  70                  75                  80

Gln Pro Asp Asp Phe Ala Thr Tyr Tyr Cys Gln Gly Asn Phe Asn Thr
                85                  90                  95

Gly Asp Arg Tyr Ala Phe Gly Gln Gly Thr Lys Leu Thr Val Leu Gly
            100                 105                 110

Gly Gly Gly Gly Ser Gly Gly Gly Ser Gly Gly Gly Gly Ser Gly
        115                 120                 125

Gly Gly Gly Ser Glu Val Gln Leu Val Glu Ser Gly Gly Gly Ser Val
    130                 135                 140

Gln Pro Gly Gly Ser Leu Arg Leu Ser Cys Thr Ala Ser Gly Phe Thr
145                 150                 155                 160

Ile Ser Arg Ser Tyr Trp Ile Cys Trp Val Arg Gln Ala Pro Gly Lys
                165                 170                 175

Gly Leu Glu Trp Val Gly Cys Ile Tyr Gly Asp Asn Asp Ile Thr Pro
            180                 185                 190

Leu Tyr Ala Asn Trp Ala Lys Gly Arg Phe Thr Ile Ser Arg Asp Thr
        195                 200                 205

Ser Lys Asn Thr Val Tyr Leu Gln Met Asn Ser Leu Arg Ala Glu Asp
    210                 215                 220

Thr Ala Thr Tyr Tyr Cys Ala Arg Leu Gly Tyr Ala Asp Tyr Ala Tyr
225                 230                 235                 240

Asp Leu Trp Gly Gln Gly Thr Thr Val Thr Val Ser Ser
                245                 250

<210> SEQ ID NO 11
<211> LENGTH: 231
<212> TYPE: PRT
```

<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (24)..(73)
<223> OTHER INFORMATION: X can be any naturally occurring amino acid.
      at least one and up to 50 amino acids can be present
<220> FEATURE:
<221> NAME/KEY: MISC_FEATURE
<222> LOCATION: (89)..(138)
<223> OTHER INFORMATION: X can be any naturally occurring amino acid.
      at least one and up to 50 amino acids can be present
<220> FEATURE:
<221> NAME/KEY: MISC_FEATURE
<222> LOCATION: (171)..(220)
<223> OTHER INFORMATION: X can be any naturally occurring amino acid.
      at least one and up to 50 amino acids can be present

<400> SEQUENCE: 11

Glu Ile Val Met Thr Gln Ser Pro Ser Thr Leu Ser Ala Ser Val Gly
1               5                   10                  15

Asp Arg Val Ile Ile Thr Cys Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Trp Tyr Gln Gln Lys Pro Gly
65                  70                  75                  80

Lys Ala Pro Lys Leu Leu Ile Tyr Xaa Xaa Xaa Xaa Xaa Xaa Xaa
            85                  90                  95

Xaa Xaa Xaa Xaa Xaa Xaa Xaa Xaa Xaa Xaa Xaa Xaa Xaa Xaa Xaa
        100                 105                 110

Xaa Xaa Xaa Xaa Xaa Xaa Xaa Xaa Xaa Xaa Xaa Xaa Xaa Xaa Xaa
    115                 120                 125

Xaa Xaa Xaa Xaa Xaa Xaa Xaa Xaa Xaa Gly Val Pro Ser Arg Phe
        130                 135                 140

Ser Gly Ser Gly Ser Gly Ala Glu Phe Thr Leu Thr Ile Ser Ser Leu
145                 150                 155                 160

Gln Pro Asp Asp Phe Ala Thr Tyr Tyr Cys Xaa Xaa Xaa Xaa Xaa Xaa
            165                 170                 175

Xaa Xaa Xaa Xaa Xaa Xaa Xaa Xaa Xaa Xaa Xaa Xaa Xaa Xaa Xaa
        180                 185                 190

Xaa Xaa Xaa Xaa Xaa Xaa Xaa Xaa Xaa Xaa Xaa Xaa Xaa Xaa Xaa
    195                 200                 205

Xaa Xaa Xaa Xaa Xaa Xaa Xaa Xaa Xaa Xaa Xaa Xaa Phe Gly Gln Gly
        210                 215                 220

Thr Lys Leu Thr Val Leu Gly
225                 230

<210> SEQ ID NO 12
<211> LENGTH: 231
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (24)..(73)
<223> OTHER INFORMATION: X can be any naturally occurring amino acid.
      at least one and up to 50 amino acids can be present
<220> FEATURE:

-continued

```
<221> NAME/KEY: MISC_FEATURE
<222> LOCATION: (89)..(138)
<223> OTHER INFORMATION: X can be any naturally occurring amino acid.
      at least one and up to 50 amino acids can be present
<220> FEATURE:
<221> NAME/KEY: MISC_FEATURE
<222> LOCATION: (171)..(220)
<223> OTHER INFORMATION: X can be any naturally occurring amino acid.
      at least one and up to 50 amino acids can be present

<400> SEQUENCE: 12

Glu Ile Val Met Thr Gln Ser Pro Ser Thr Leu Ser Ala Ser Val Gly
1               5                   10                  15

Asp Arg Val Ile Ile Thr Cys Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Trp Tyr Gln Gln Lys Pro Gly
65                  70                  75                  80

Lys Ala Pro Lys Leu Leu Ile Tyr Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa
        100                 105                 110

Xaa Xaa Xaa Xaa Xaa Xaa Xaa Xaa Xaa Xaa Xaa Xaa Xaa Xaa
    115                 120                 125

Xaa Xaa Xaa Xaa Xaa Xaa Xaa Xaa Xaa Gly Val Pro Ser Arg Phe
130                 135                 140

Ser Gly Ser Gly Ser Gly Thr Glu Phe Thr Leu Thr Ile Ser Ser Leu
145                 150                 155                 160

Gln Pro Asp Asp Phe Ala Thr Tyr Tyr Cys Xaa Xaa Xaa Xaa Xaa
                165                 170                 175

Xaa Xaa Xaa Xaa Xaa Xaa Xaa Xaa Xaa Xaa Xaa Xaa Xaa Xaa
        180                 185                 190

Xaa Xaa Xaa Xaa Xaa Xaa Xaa Xaa Xaa Xaa Xaa Xaa Xaa Xaa
    195                 200                 205

Xaa Xaa Xaa Xaa Xaa Xaa Xaa Xaa Xaa Xaa Xaa Phe Gly Gln Gly
210                 215                 220

Thr Lys Leu Thr Val Leu Gly
225                 230

<210> SEQ ID NO 13
<211> LENGTH: 231
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (24)..(73)
<223> OTHER INFORMATION: X can be any naturally occurring amino acid.
      at least one and up to 50 amino acids can be present
<220> FEATURE:
<221> NAME/KEY: MISC_FEATURE
<222> LOCATION: (89)..(138)
<223> OTHER INFORMATION: X can be any naturally occurring amino acid.
      at least one and up to 50 amino acids can be present
<220> FEATURE:
<221> NAME/KEY: MISC_FEATURE
<222> LOCATION: (171)..(220)
<223> OTHER INFORMATION: X can be any naturally occurring amino acid.
      at least one and up to 50 amino acids can be present
```

<400> SEQUENCE: 13

Glu Ile Val Met Thr Gln Ser Pro Ser Thr Leu Ser Ala Ser Val Gly
1               5                   10                  15

Asp Arg Val Ile Ile Thr Cys Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Trp Tyr Gln Gln Arg Pro Gly
65                  70                  75                  80

Lys Ala Pro Lys Leu Leu Ile Tyr Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Gly Val Pro Ser Arg Phe
    130                 135                 140

Ser Gly Ser Gly Ser Gly Ala Glu Phe Thr Leu Thr Ile Ser Ser Leu
145                 150                 155                 160

Gln Pro Asp Asp Phe Ala Thr Tyr Tyr Cys Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Phe Gly Gln Gly
    210                 215                 220

Thr Lys Leu Thr Val Leu Gly
225                 230

<210> SEQ ID NO 14
<211> LENGTH: 111
<212> TYPE: PRT
<213> ORGANISM: Artificial
<220> FEATURE:
<223> OTHER INFORMATION: Synthetic Peptide

<400> SEQUENCE: 14

Glu Ile Val Met Thr Gln Ser Pro Ser Thr Leu Ser Ala Ser Val Gly
1               5                   10                  15

Asp Arg Val Ile Ile Thr Cys Gln Ser Ser Gln Ser Val Tyr Gly Asn
            20                  25                  30

Ile Trp Met Ala Trp Tyr Gln Gln Arg Pro Gly Lys Ala Pro Lys Leu
        35                  40                  45

Leu Ile Tyr Gln Ala Ser Lys Leu Ala Ser Gly Val Pro Ser Arg Phe
    50                  55                  60

Ser Gly Ser Gly Ser Gly Ala Glu Phe Thr Leu Thr Ile Ser Ser Leu
65                  70                  75                  80

Gln Pro Asp Asp Phe Ala Thr Tyr Tyr Cys Gln Gly Asn Phe Asn Thr
                85                  90                  95

Gly Asp Arg Tyr Ala Phe Gly Gln Gly Thr Lys Leu Thr Val Leu
            100                 105                 110

```
<210> SEQ ID NO 15
<211> LENGTH: 483
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (24)..(73)
<223> OTHER INFORMATION: X can be any naturally occurring amino acid.
      at least one and up to 50 amino acids can be present
<220> FEATURE:
<221> NAME/KEY: MISC_FEATURE
<222> LOCATION: (89)..(138)
<223> OTHER INFORMATION: X can be any naturally occurring amino acid.
      at least one and up to 50 amino acids can be present
<220> FEATURE:
<221> NAME/KEY: MISC_FEATURE
<222> LOCATION: (171)..(220)
<223> OTHER INFORMATION: X can be any naturally occurring amino acid.
      at least one and up to 50 amino acids can be present
<220> FEATURE:
<221> NAME/KEY: MISC_FEATURE
<222> LOCATION: (277)..(326)
<223> OTHER INFORMATION: X can be any naturally occurring amino acid.
      at least one and up to 50 amino acids can be present
<220> FEATURE:
<221> NAME/KEY: MISC_FEATURE
<222> LOCATION: (341)..(390)
<223> OTHER INFORMATION: X can be any naturally occurring amino acid.
      at least one and up to 50 amino acids can be present
<220> FEATURE:
<221> NAME/KEY: MISC_FEATURE
<222> LOCATION: (423)..(483)
<223> OTHER INFORMATION: X can be any naturally occurring amino acid.
      at least one and up to 50 amino acids can be present

<400> SEQUENCE: 15

Glu Ile Val Met Thr Gln Ser Pro Ser Thr Leu Ser Ala Ser Val Gly
1               5                   10                  15

Asp Arg Val Ile Ile Thr Cys Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Trp Tyr Gln Gln Arg Pro Gly
65                  70                  75                  80

Lys Ala Pro Lys Leu Leu Ile Tyr Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Gly Val Pro Ser Arg Phe
    130                 135                 140

Ser Gly Ser Gly Ser Gly Thr Glu Phe Thr Leu Thr Ile Ser Ser Leu
145                 150                 155                 160

Gln Pro Asp Asp Phe Ala Thr Tyr Tyr Cys Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa Xaa
        195                 200                 205
```

```
Xaa Xaa Xaa Xaa Xaa Xaa Xaa Xaa Xaa Xaa Phe Gly Gln Gly
    210                 215                 220

Thr Lys Leu Thr Val Leu Gly Gly Gly Gly Ser Gly Gly Gly Gly
225                 230                 235                 240

Ser Gly Gly Gly Ser Gly Gly Gly Gly Ser Glu Val Gln Leu Val
                245                 250                 255

Glu Ser Gly Gly Gly Leu Val Gln Pro Gly Gly Ser Leu Arg Leu Ser
            260                 265                 270

Cys Thr Ala Ser Xaa Xaa Xaa Xaa Xaa Xaa Xaa Xaa Xaa Xaa Xaa
        275                 280                 285

Xaa Xaa Xaa Xaa Xaa Xaa Xaa Xaa Xaa Xaa Xaa Xaa Xaa Xaa Xaa
    290                 295                 300

Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Trp Val Arg Gln Ala Pro Gly Lys Gly Leu
                325                 330                 335

Glu Trp Val Gly Xaa Xaa Xaa Xaa Xaa Xaa Xaa Xaa Xaa Xaa
            340                 345                 350

Xaa Xaa Xaa Xaa Xaa Xaa Xaa Xaa Xaa Xaa Xaa Xaa Xaa Xaa Xaa
    355                 360                 365

Xaa Xaa Xaa Xaa Xaa Xaa Xaa Xaa Xaa Xaa Xaa Xaa Xaa Xaa Xaa
370                 375                 380

Xaa Xaa Xaa Xaa Xaa Xaa Arg Phe Thr Ile Ser Arg Asp Thr Ser Lys
385                 390                 395                 400

Asn Thr Val Tyr Leu Gln Met Asn Ser Leu Arg Ala Glu Asp Thr Ala
                405                 410                 415

Val Tyr Tyr Cys Ala Arg Xaa Xaa Xaa Xaa Xaa Xaa Xaa Xaa Xaa
            420                 425                 430

Xaa Xaa Xaa Xaa Xaa Xaa Xaa Xaa Xaa Xaa Xaa Xaa Xaa Xaa
    435                 440                 445

Xaa Xaa Xaa Xaa Xaa Xaa Xaa Xaa Xaa Xaa Xaa Xaa Xaa
        450                 455                 460

Xaa Xaa Xaa Xaa Xaa Xaa Xaa Xaa Trp Gly Gln Gly Thr Leu Val Thr
465                 470                 475                 480

Val Ser Ser

<210> SEQ ID NO 16
<211> LENGTH: 483
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (24)..(73)
<223> OTHER INFORMATION: X can be any naturally occurring amino acid.
      at least one and up to 50 amino acids can be present
<220> FEATURE:
<221> NAME/KEY: MISC_FEATURE
<222> LOCATION: (89)..(138)
<223> OTHER INFORMATION: X can be any naturally occurring amino acid.
      at least one and up to 50 amino acids can be present
<220> FEATURE:
<221> NAME/KEY: MISC_FEATURE
<222> LOCATION: (171)..(220)
<223> OTHER INFORMATION: X can be any naturally occurring amino acid.
      at least one and up to 50 amino acids can be present
<220> FEATURE:
<221> NAME/KEY: MISC_FEATURE
<222> LOCATION: (277)..(326)
<223> OTHER INFORMATION: X can be any naturally occurring amino acid.
``` at least one and up to 50 amino acids can be present
<220> FEATURE:
<221> NAME/KEY: MISC_FEATURE
<222> LOCATION: (341)..(390)
<223> OTHER INFORMATION: X can be any naturally occurring amino acid.
      at least one and up to 50 amino acids can be present
<220> FEATURE:
<221> NAME/KEY: MISC_FEATURE
<222> LOCATION: (423)..(483)
<223> OTHER INFORMATION: X can be any naturally occurring amino acid.
      at least one and up to 50 amino acids can be present

<400> SEQUENCE: 16

Glu Ile Val Met Thr Gln Ser Pro Ser Thr Leu Ser Ala Ser Val Gly
1               5                   10                  15

Asp Arg Val Ile Ile Thr Cys Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Trp Tyr Gln Gln Arg Pro Gly
65                  70                  75                  80

Lys Ala Pro Lys Leu Leu Ile Tyr Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
        100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Gly Val Pro Ser Arg Phe
    130                 135                 140

Ser Gly Ser Gly Ser Gly Thr Glu Phe Thr Leu Thr Ile Ser Ser Leu
145                 150                 155                 160

Gln Pro Asp Asp Phe Ala Thr Tyr Tyr Cys Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa
        180                 185                 190

Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Phe Gly Gln Gly
    210                 215                 220

Thr Lys Leu Thr Val Leu Gly Gly Gly Gly Ser Gly Gly Gly
225                 230                 235                 240

Ser Gly Gly Gly Gly Ser Gly Gly Gly Ser Glu Val Gln Leu Val
            245                 250                 255

Glu Ser Gly Gly Gly Leu Val Gln Pro Gly Gly Ser Leu Arg Leu Ser
            260                 265                 270

Cys Thr Val Ser Xaa Xaa Xaa Xaa Xaa Xaa Xaa Xaa Xaa Xaa
            275                 280                 285

Xaa Xaa Xaa Xaa Xaa Xaa Xaa Xaa Xaa Xaa Xaa Xaa
    290                 295                 300

Xaa Xaa Xaa Xaa Xaa Xaa Xaa Xaa Xaa Xaa Xaa Xaa
305                 310                 315                 320

Xaa Xaa Xaa Xaa Xaa Xaa Trp Val Arg Gln Ala Pro Gly Lys Gly Leu
            325                 330                 335

Glu Trp Val Gly Xaa Xaa Xaa Xaa Xaa Xaa Xaa Xaa Xaa Xaa
            340                 345                 350

```
Xaa Xaa Xaa Xaa Xaa Xaa Xaa Xaa Xaa Xaa Xaa Xaa Xaa Xaa
        355                 360                 365

Xaa Xaa Xaa Xaa Xaa Xaa Xaa Xaa Xaa Xaa Xaa Xaa
        370                 375                 380

Xaa Xaa Xaa Xaa Xaa Xaa Arg Phe Thr Ile Ser Lys Asp Thr Ser Lys
385                 390                 395                 400

Asn Thr Val Tyr Leu Gln Met Asn Ser Leu Arg Ala Glu Asp Thr Ala
                    405                 410                 415

Val Tyr Tyr Cys Ala Arg Xaa Xaa Xaa Xaa Xaa Xaa Xaa Xaa Xaa
                420                 425                 430

Xaa Xaa Xaa Xaa Xaa Xaa Xaa Xaa Xaa Xaa Xaa Xaa Xaa Xaa Xaa Xaa
        435                 440                 445

Xaa Xaa Xaa Xaa Xaa Xaa Xaa Xaa Xaa Xaa Xaa Xaa Xaa Xaa Xaa Xaa
        450                 455                 460

Xaa Xaa Xaa Xaa Xaa Xaa Xaa Trp Gly Gln Gly Thr Leu Val Thr
465                 470                 475                 480

Val Ser Ser

<210> SEQ ID NO 17
<211> LENGTH: 253
<212> TYPE: PRT
<213> ORGANISM: Artificial
<220> FEATURE:
<223> OTHER INFORMATION: Synthetic Peptide

<400> SEQUENCE: 17

Glu Ile Val Met Thr Gln Ser Pro Ser Thr Leu Ser Ala Ser Val Gly
1               5                   10                  15

Asp Arg Val Ile Ile Thr Cys Gln Ser Ser Gln Ser Val Tyr Gly Asn
            20                  25                  30

Ile Trp Met Ala Trp Tyr Gln Gln Arg Pro Gly Lys Ala Pro Lys Leu
        35                  40                  45

Leu Ile Tyr Gln Ala Ser Lys Leu Ala Ser Gly Val Pro Ser Arg Phe
    50                  55                  60

Ser Gly Ser Gly Ser Gly Ala Glu Phe Thr Leu Thr Ile Ser Ser Leu
65                  70                  75                  80

Gln Pro Asp Asp Phe Ala Thr Tyr Tyr Cys Gln Gly Asn Phe Asn Thr
                    85                  90                  95

Gly Asp Arg Tyr Ala Phe Gly Gly Gly Thr Lys Leu Thr Val Leu Gly
                100                 105                 110

Gly Gly Gly Gly Ser Gly Gly Gly Gly Ser Gly Gly Gly Gly Ser Gly
            115                 120                 125

Gly Gly Gly Ser Glu Val Gln Leu Val Glu Ser Gly Gly Gly Ser Val
        130                 135                 140

Gln Pro Gly Gly Ser Leu Arg Leu Ser Cys Thr Ala Ser Gly Phe Thr
145                 150                 155                 160

Ile Ser Arg Ser Tyr Trp Ile Cys Trp Val Arg Gln Ala Pro Gly Lys
                165                 170                 175

Gly Leu Glu Trp Val Gly Cys Ile Tyr Gly Asp Asn Asp Ile Thr Pro
                180                 185                 190
```

```
Leu Tyr Ala Asn Trp Ala Lys Gly Arg Phe Thr Ile Ser Arg Asp Thr
            195                 200                 205

Ser Lys Asn Thr Val Tyr Leu Gln Met Asn Ser Leu Arg Ala Glu Asp
        210                 215                 220

Thr Ala Thr Tyr Tyr Cys Ala Arg Leu Gly Tyr Ala Asp Tyr Ala Tyr
225                 230                 235                 240

Asp Leu Trp Gly Gln Gly Thr Val Thr Val Ser Ser
                245                 250

<210> SEQ ID NO 18
<211> LENGTH: 253
<212> TYPE: PRT
<213> ORGANISM: Artificial
<220> FEATURE:
<223> OTHER INFORMATION: Synthetic Peptide

<400> SEQUENCE: 18

Glu Ile Val Met Thr Gln Ser Pro Ser Thr Leu Ser Ala Ser Val Gly
1               5                   10                  15

Asp Arg Val Ile Ile Thr Cys Gln Ser Ser Gln Ser Val Tyr Gly Asn
            20                  25                  30

Ile Trp Met Ala Trp Tyr Gln Gln Lys Pro Gly Lys Ala Pro Lys Leu
        35                  40                  45

Leu Ile Tyr Gln Ala Ser Lys Leu Ala Ser Gly Val Pro Ser Arg Phe
    50                  55                  60

Ser Gly Ser Gly Ser Gly Ala Glu Phe Thr Leu Thr Ile Ser Ser Leu
65                  70                  75                  80

Gln Pro Asp Asp Phe Ala Thr Tyr Tyr Cys Gly Asn Phe Asn Thr
                85                  90                  95

Gly Asp Arg Tyr Ala Phe Gly Gln Gly Thr Lys Leu Thr Val Leu Gly
            100                 105                 110

Gly Gly Gly Gly Ser Gly Gly Gly Ser Gly Gly Gly Gly Ser Gly
            115                 120                 125

Gly Gly Gly Ser Glu Val Gln Leu Val Glu Ser Gly Gly Gly Ser Val
        130                 135                 140

Gln Pro Gly Gly Ser Leu Arg Leu Ser Cys Thr Ala Ser Gly Phe Thr
145                 150                 155                 160

Ile Ser Arg Ser Tyr Trp Ile Cys Trp Val Arg Gln Ala Pro Gly Lys
                165                 170                 175

Gly Leu Glu Trp Val Gly Cys Ile Tyr Gly Asp Asn Asp Ile Thr Pro
            180                 185                 190

Leu Tyr Ala Asn Trp Ala Lys Gly Arg Phe Thr Ile Ser Arg Asp Thr
        195                 200                 205

Ser Lys Asn Thr Val Tyr Leu Gln Met Asn Ser Leu Arg Ala Glu Asp
    210                 215                 220

Thr Ala Thr Tyr Tyr Cys Ala Arg Leu Gly Tyr Ala Asp Tyr Ala Tyr
225                 230                 235                 240

Asp Leu Trp Gly Gln Gly Thr Val Thr Val Ser Ser
                245                 250
```

STABLE AND SOLUBLE ANTIBODIES

CROSS-REFERENCE TO RELATED APPLICATIONS

The present application is a divisional application of U.S. patent application Ser. No. 13/278,500 filed Oct. 21, 2011, which claims benefit to U.S. Provisional Patent Application Nos. 61/405,798 filed Oct. 22, 2010, and 61/484,749 filed May 11, 2011 the entire contents of which are incorporated herein by reference.

FIELD OF THE INVENTION

The invention relates to methods of reducing aggregation propensity of antibodies, and antibodies that are modified to reduce aggregration propensity. The invention also relates to antibodies that bind tumor necrosis factor alpha (TNFα). In particular, the invention relates to stable and soluble antibodies comprising an aggregation-reducing modification, including scFv antibodies and Fab fragments, which comprise specific light chain and heavy chain sequences that are optimized for stability, solubility, and low immunogenicity. In addition, the invention relates to methods for the diagnosis and/or treatment of TNF-mediated disorders.

BACKGROUND OF THE INVENTION

Tumour necrosis factor alpha (TNFα, also known as cachectin), is a naturally occurring mammalian cytokine produced by numerous cell types, including monocytes and macrophages in response to endotoxin or other stimuli. TNFα is a major mediator of inflammatory, immunological, and pathophysiological reactions (Grell, M., et al. (1995) Cell, 83: 793-802).

Soluble TNFα is formed by the cleavage of a precursor transmembrane protein (Kriegler, et al. (1988) Cell 53: 45-53), and the secreted 17 kDa polypeptides assemble to soluble homotrimer complexes (Smith, et al. (1987), J. Biol. Chem. 262: 6951-6954; for reviews of TNFA, see Butler, et al. (1986), Nature 320:584; Old (1986), Science 230: 630). These complexes then bind to receptors found on a variety of cells. Binding produces an array of pro-inflammatory effects, including (i) release of other pro-inflammatory cytokines such as interleukin (IL)-6, IL-8, and IL-1, (ii) release of matrix metalloproteinases and (iii) up regulation of the expression of endothelial adhesion molecules, further amplifying the inflammatory and immune cascade by attracting leukocytes into extravascular tissues.

A large number of disorders are associated with elevated levels of TNFα, many of them of significant medical importance. TNFα has been shown to be up-regulated in a number of human diseases, including chronic diseases such as rheumatoid arthritis (RA), inflammatory bowel disorders including Crohn's disease and ulcerative colitis, sepsis, congestive heart failure, asthma bronchiale and multiple sclerosis. Mice transgenic for human TNFα produce high levels of TNFα constitutively and develop a spontaneous, destructive polyarthritis resembling RA (Keffer et al. 1991, EMBO J., 10, 4025-4031). TNFα is therefore referred to as a pro-inflammatory cytokine.

TNFα is now well established as key in the pathogenesis of RA, which is a chronic, progressive and debilitating disease characterised by polyarticular joint inflammation and destruction, with systemic symptoms of fever and malaise and fatigue. RA also leads to chronic synovial inflammation, with frequent progression to articular cartilage and bone destruction. Increased levels of TNFα are found in both the synovial fluid and peripheral blood of patients suffering from RA. When TNFα blocking agents are administered to patients suffering from RA, they reduce inflammation, improve symptoms and retard joint damage (McKown et al. (1999), Arthritis Rheum. 42:1204-1208).

Physiologically, TNFα is also associated with protection from particular infections (Cerami. et al. (1988), Immunol. Today 9:28). TNFα is released by macrophages that have been activated by lipopolysaccharides of Gram-negative bacteria. As such, TNFα appears to be an endogenous mediator of central importance involved in the development and pathogenesis of endotoxic shock associated with bacterial sepsis (Michie, et al. (1989), Br. J. Surg. 76:670-671.; Debets. et al. (1989), Second Vienna Shock Forum, p. 463-466; Simpson, et al. (1989) Crit. Care Clin. 5: 27-47; Waage et al. (1987). Lancet 1: 355-357; Hammerle. et al. (1989) Second Vienna Shock Forum p. 715-718; Debets. et al. (1989), Crit. Care Med. 17:489-497; Calandra. et al. (1990), J. Infect. Dis. 161:982-987; Revhaug et al. (1988), Arch. Surg. 123:162-170).

As with other organ systems, TNFα has also been shown to play a key role in the central nervous system, in particular in inflammatory and autoimmune disorders of the nervous system, including multiple sclerosis, Guillain-Barre syndrome and myasthenia gravis, and in degenerative disorders of the nervous system, including Alzheimer's disease, Parkinson's disease and Huntington's disease. TNFα is also involved in disorders of related systems of the retina and of muscle, including optic neuritis, macular degeneration, diabetic retinopathy, dermatomyositis, amyotrophic lateral sclerosis, and muscular dystrophy, as well as in injuries to the nervous system, including traumatic brain injury, acute spinal cord injury, and stroke.

Hepatitis is another TNFα-related inflammatory disorder which among other triggers can be caused by viral infections, including Epstein-Barr, cytomegalovirus, and hepatitis A-E viruses. Hepatitis causes acute liver inflammation in the portal and lobular region, followed by fibrosis and tumor progression. TNFα can also mediate cachexia in cancer, which causes most cancer morbidity and mortality (Tisdale M. J. (2004), Langenbecks Arch Surg. 389:299-305).

The key role played by TNFα in inflammation, cellular immune responses and the pathology of many diseases has led to the search for antagonists of TNFα. One class of TNFα antagonists designed for the treatment of TNFα-mediated diseases are antibodies or antibody fragments that specifically bind TNFα and thereby block its function. The use of anti-TNFα antibodies has shown that a blockade of TNFα can reverse effects attributed to TNFα including decreases in IL-1, GM-CSF, IL-6, IL-8, adhesion molecules and tissue destruction (Feldmann et al. (1997), Adv. Immunol. 1997:283-350). Among the specific inhibitors of TNFα that have recently become commercially available include a monoclonal, chimeric mouse-human antibody directed against TNFα (infliximab, REMICADE; Centocor Corporation/Johnson & Johnson) has demonstrated clinical efficacy in the treatment of RA and Crohn's disease. Despite these advances, there remains a need for new and effective forms of antibodies or other antibodies for the treatment for TNFα-associated disorders such as RA. In particular, there is an urgent need for antibodies with optimal functional properties for the effective and continuous treatment of arthritis and other TNFα-mediated disorders.

SUMMARY OF THE INVENTION

The invention provides antibodies comprising at least one aggregation-reducing mutation and methods for producing such antibodies.

In one aspect, the invention provides a method of reducing the propensity for aggregation of an antibody, the method comprising introducing one or more aggregation-reducing modifications at a residue position participating in the interface between the variable light chain and the variable heavy chain of an antibody, wherein the substitution reduces the free energy between the variable light chain and variable heavy chain by at least 0.5 kcal/mol, thereby reducing the aggregation propensity of the modified antibody compared with that of a parental antibody that lacks the aggregaton-reducing modification(s).

In one aspect, a method of the invention comprises introducing one or more amino acid substitutions in the interface of a variable light chain (VL) and a variable heavy chain (VH) of the antibody, wherein the one or more substitutions are at residue positions selected to reduce the free energy between the VL and VH by at least 10%, thereby reducing the aggregation propensity of the antibody compared with a parental antibody. In a particular aspect, the sequence of the variable light chain of the antibody has at least 65% identity to the sequence of SEQ ID NO: 1. In other aspects, the variable heavy chain sequence has at least 85% identity to the sequence of SEQ ID NO: 3 or the sequence of SEQ ID NO: 4.

In certain aspects, a method of the invention comprises modifying the residue at AHo position 50 and/or the residue at AHo position 47 in the variable light chain of an antibody, thereby reducing the aggregation propensity of the antibody compared with a parental antibody. In other aspects, the method of the invention further comprises modifying residues at AHo position 12, 103, and 144 of the variable heavy chain.

The invention also provides antibodies having reduced propensity for aggregration comprising one or more aggregation-reducing modifications. In certain aspects, an antibody of the invention is a Fab, Fab', a F(ab')2, single-chain Fv (scFv), an Fv fragment, or a linear antibody. In other aspects, the invention provides a bispecific or bivalent molecule comprising an antibody of the invention.

In other aspects, the aggregation-reducing modification is at AHo position 50 of the variable light chain. In a particular aspect, the aggregation-reducing modification comprises an arginine (R) at AHo position 50 of the variable light chain. In yet another aspect, the aggregation-reducing modification comprises a substitution of lysine (K) by arginine (R) at AHo position 50 of the variable light chain.

In still other aspects, the aggregation-reducing modification is at AHo position 47 of the variable light chain. In a particular aspect, the aggregation-reducing modification comprises an arginine (R) at AHo position 47 of the variable light chain. In yet another aspect, the aggregation-reducing modification comprises a substitution of lysine (K) by arginine (R) at AHo position 47 of the variable light chain.

The invention also provides stable and soluble antibodies specific for TNFα, which comprise specific light chain and heavy chain sequences that are optimized for stability, solubility, in vitro and in vivo binding of TNFα, and low immunogenicity. Said antibodies are designed for the diagnosis and/or treatment of TNFα-mediated disorders. The nucleic acids, vectors and host cells for expression of the recombinant antibodies, variable light chains, and variable heavy chains of the invention, methods for isolating them and the use of said antibodies in medicine are also disclosed.

The invention also provides methods of treating a TNFα-mediated disorder comprising administering to a subject in need thereof the pharmaceutical composition comprising an anti-TNFα antibody of the invention. In certain aspects, the TNFalpha-mediated disorder is an ocular disorder selected from the group consisting of uveitis, Bechet's disease, retinitis, dry eye, glaucoma, Sjörgen syndrome, diabetic neuropathy, scleritis, age related macular degeneration and keratitis.

Specific preferred embodiments of the invention will become evident from the following more detailed description of certain preferred embodiments and the claims.

BRIEF DESCRIPTION OF THE DRAWINGS

FIG. 7A shows stability of 34rFW1.4 under accelerated conditions determined by SE-HPLC analysis after 2 weeks incubation at 40° C. and using 20 mg/ml concentration.

FIG. 7B shows stability of 34rFW1.4_VLK50R under accelerated conditions determined by SE-HPLC analysis after 2 weeks incubation at 40° C. and using 20 mg/ml concentration.

DETAILED DESCRIPTION OF THE INVENTION

Figure 1:
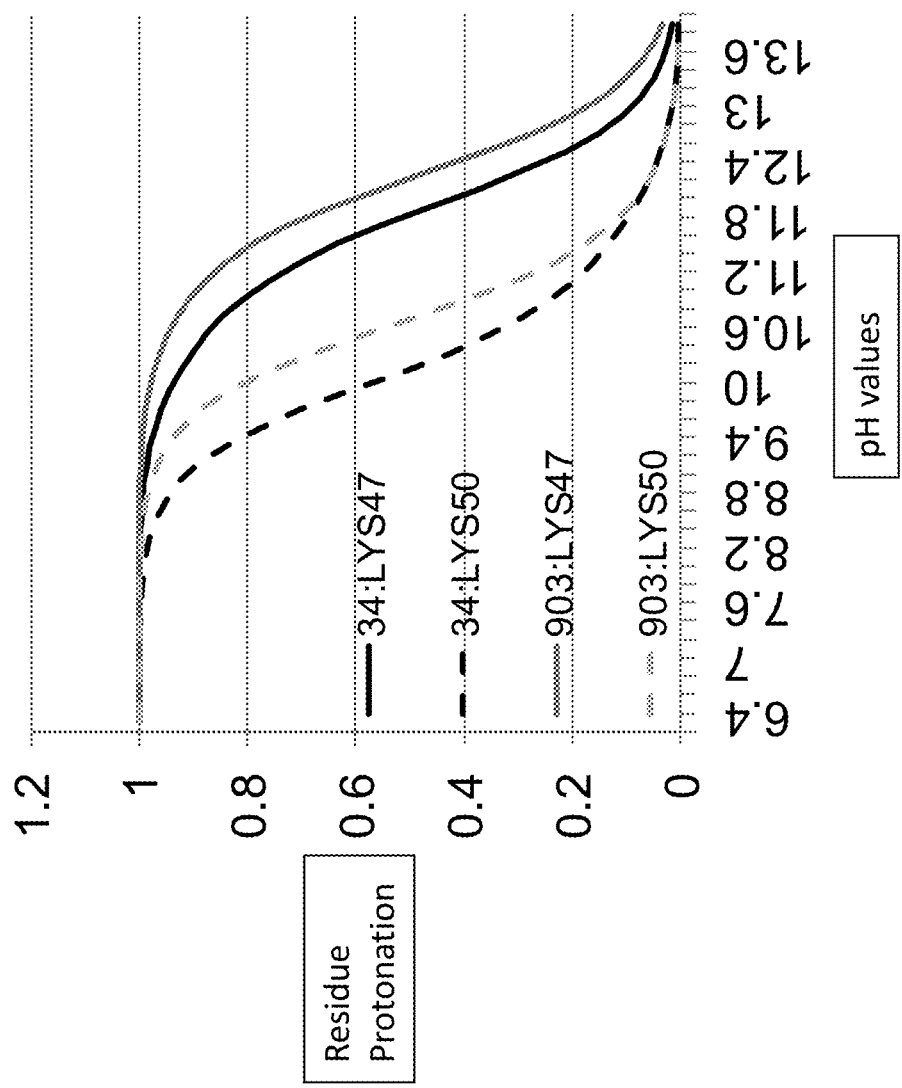
FIG. 1 shows titration curves of residue positions VL47 (solid lines) and VL50 (dashed lines) in two different scFv molecules, 34rFW1.4 (black) and 578rFW1.4 (gray).
Figure 2A:
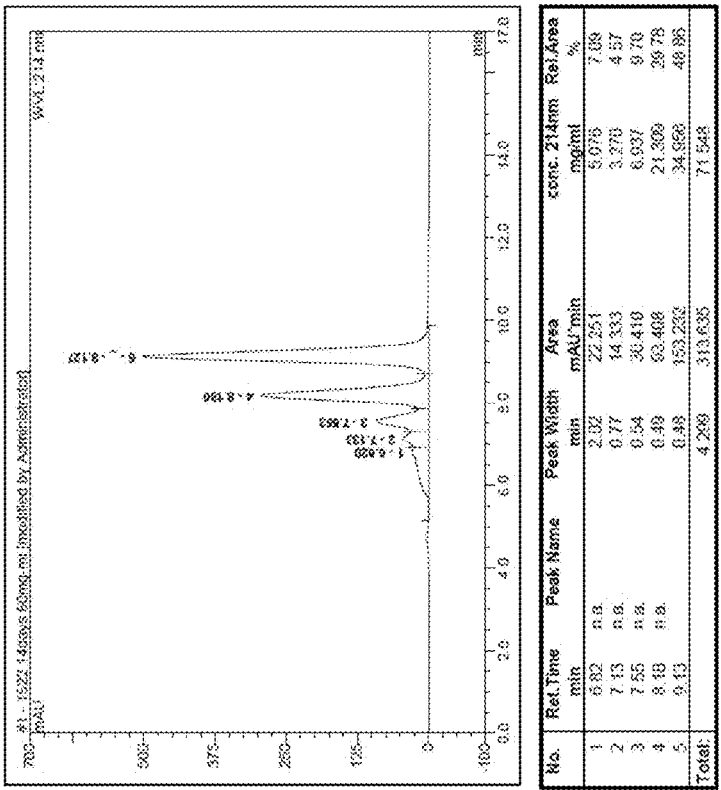
FIG. 2A shows stability of 34rFW1.4 under accelerated conditions determined by SE-HPLC analysis after 2 weeks incubation at 40° C. and using 60 mg/ml concentration.
Figure 2B:
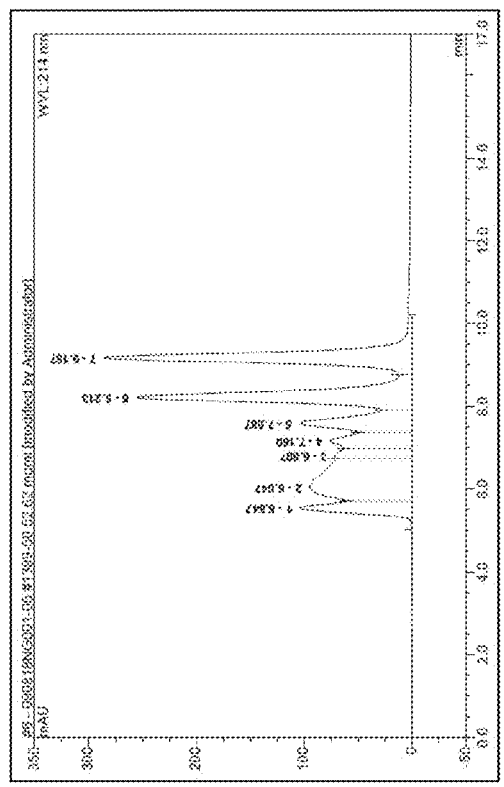
FIG. 2B shows stability of 34rFW1.4_VLK50R_DHP under accelerated conditions determined by SE-HPLC analysis after 2 weeks incubation at 40° C. and using 60 mg/ml concentration.
Figure 3A:
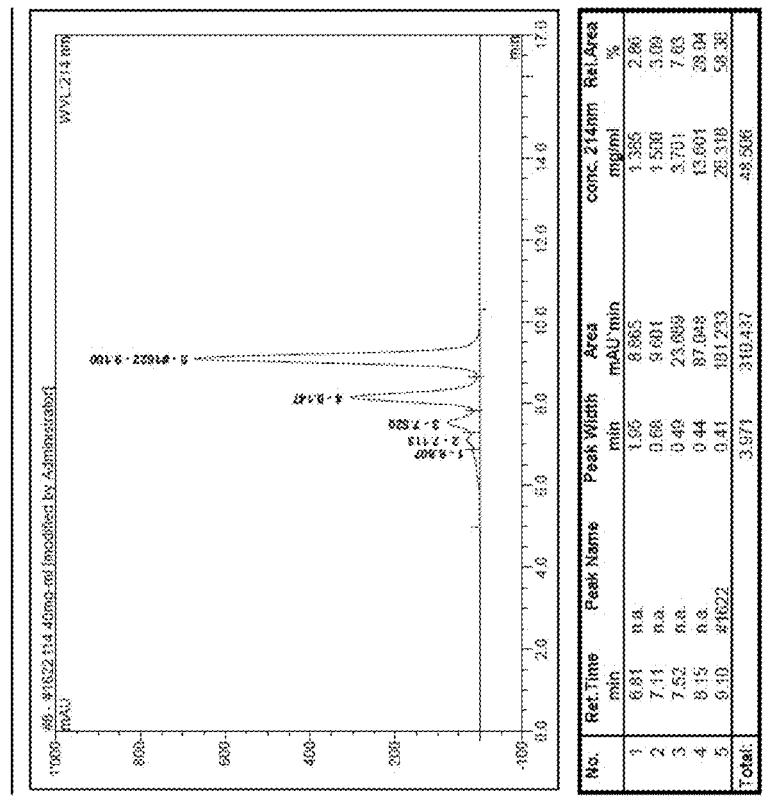
FIG. 3A shows stability of 34rFW1.4 under accelerated conditions determined by SE-HPLC analysis after 2 weeks incubation at 40° C. and using 40 mg/ml concentration.
Figure 3B:
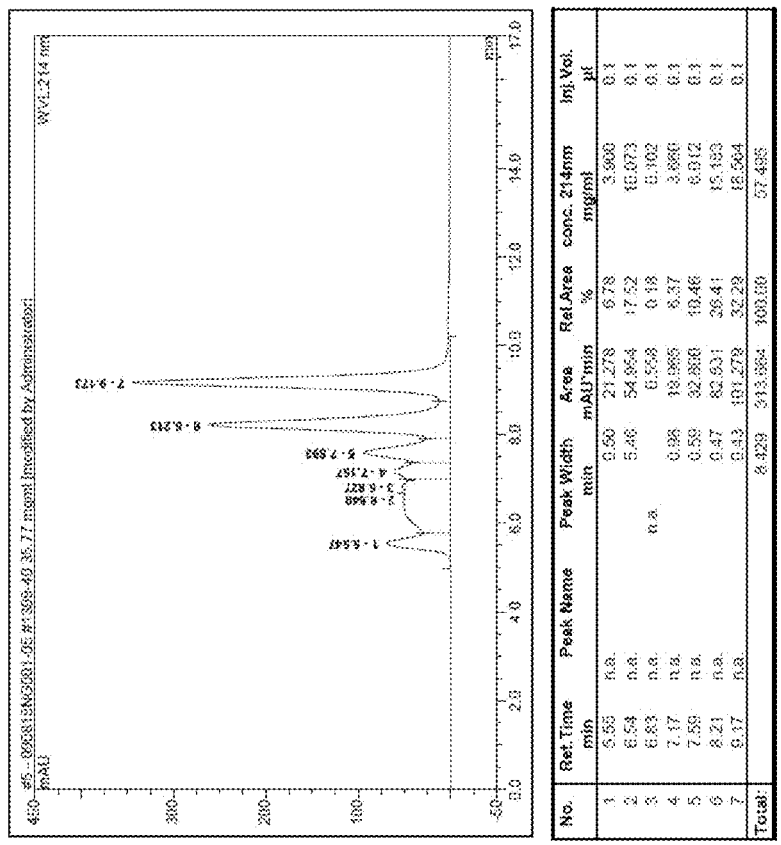
FIG. 3B shows stability of 34rFW1.4_VLK50R_DHP under accelerated conditions determined by SE-HPLC analysis after 2 weeks incubation at 40° C. and using 40 mg/ml concentration.
Figure 4B:
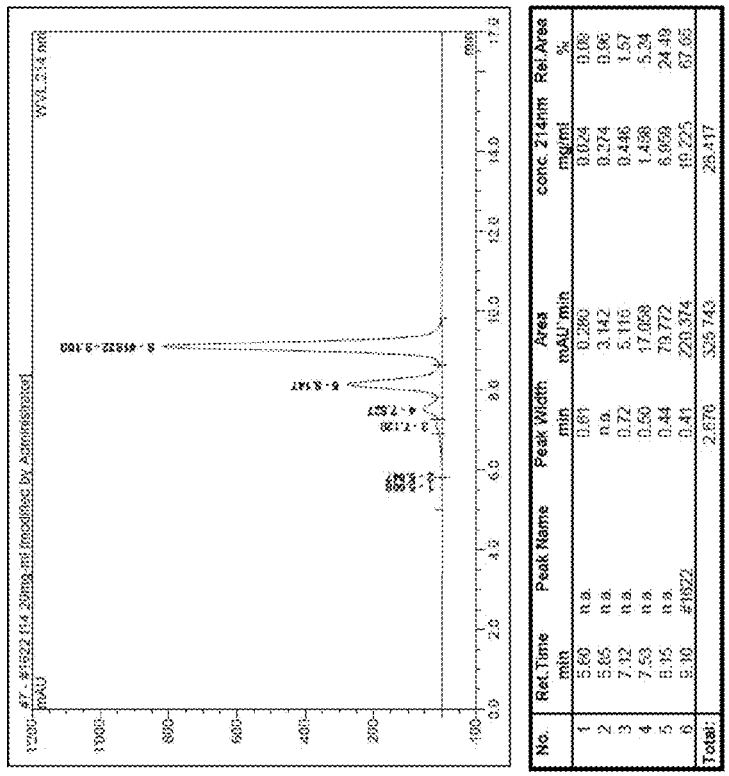
FIG. 4B shows stability of 34rFW1.4_VLK50R_DHP under accelerated conditions determined by SE-HPLC analysis after 2 weeks incubation at 40° C. and using 20 mg/ml concentration.
Figure 4A:
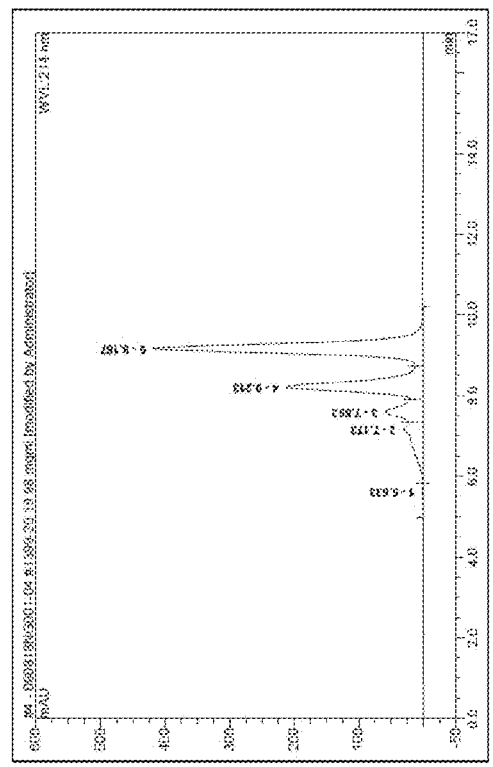
FIG. 4A shows stability of 34rFW1.4 under accelerated conditions determined by SE-HPLC analysis after 2 weeks incubation at 40° C. and using 20 mg/ml concentration.

It is a general object of the invention to provide stable and soluble antibodies having reduced propensity for aggregating in solution. In a preferred embodiment said antibody is a scFv antibody or Fab fragment. The antibodies of the invention preferably comprise a light and heavy chain as disclosed herein.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

In order that the present invention may be more readily understood, certain terms will be defined as follows. Additional definitions are set forth throughout the detailed description. The following definitions and explanations are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, $3^{rd}$ Edition or a dictionary known to those of skill in the art, such as the Oxford Dictionary of Biochemistry and Molecular Biology (Ed. Anthony Smith, Oxford University Press, Oxford, 2004).

The term "antibody" as used herein includes whole antibodies and any antigen binding fragment (i.e., "antigen-binding portion," "antigen binding polypeptide," or "immunobinder") or single chain thereof. An "antibody" includes a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding portion" of an antibody (or simply "antibody portion") refers to one or more fragments of an antibody that retain the ability to specifically bind to an antigen (e.g., TNF). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, CL and CH1 domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a single domain or dAb fragment (Ward et al., (1989) *Nature* 341: 544-546), which consists of a $V_H$ domain; and (vi) an isolated complementarity determining region (CDR) or (vii) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins. Antibodies can be of different isotype, for example, an IgG (e.g., an IgG1, IgG2, IgG3, or IgG4 subtype), IgA1, IgA2, IgD, IgE, or IgM antibody.

The term "frameworks" refers to the art recognized portions of an antibody variable region that exist between the more divergent CDR regions. Such framework regions are typically referred to as frameworks 1 through 4 (FR1, FR2, FR3, and FR4) and provide a scaffold for holding, in three-dimensional space, the three CDRs found in a heavy or light chain antibody variable region, such that the CDRs can form an antigen-binding surface. Such frameworks can also be referred to as scaffolds as they provide support for the presentation of the more divergent CDRs. Other CDRs and frameworks of the immunoglobulin superfamily, such as ankyrin repeats and fibronectin, can be used as antigen binding molecules (see also, for example, U.S. Pat. Nos. 6,300,064, 6,815,540 and U.S. Pub. No. 20040132028).

The term "epitope" or "antigenic determinant" refers to a site on an antigen to which an immunoglobulin or antibody specifically binds (e.g., TNF). An epitope typically includes at least 3, 4, 5, 6, 7, 8, 9, 10, 11, 12, 13, 14 or 15 amino acids in a unique spatial conformation. See, e.g., *Epitope Mapping Protocols in Methods in Molecular Biology*, Vol. 66, G. E. Morris, Ed. (1996).

The terms "specific binding," "selective binding," "selectively binds," and "specifically binds," refer to antibody binding to an epitope on a predetermined antigen. Typically, the antibody binds with an affinity ($K_D$) of approximately less than $10^{-7}$ M, such as approximately less than $10^{-8}$ M, $10^{-9}$ M or $10^{-10}$ M or even lower, as determined using surface plasmon resonance (SPR) technology in a BIACORE instrument.

The term "$K_D$," refers to the dissociation equilibrium constant of a particular antibody-antigen interaction. In certain embodiments, some antibodies of the invention bind to TNF with a dissociation equilibrium constant ($K_D$) of less than approximately $10^{-7}$ M, such as less than approximately $10^{-8}$ M, $10^{-9}$ M or $10^{-10}$ M or even lower, for example, as determined using surface plasmon resonance (SPR) technology in a BIACORE instrument.

As used herein, "identity" refers to the sequence matching between two polypeptides, molecules or between two nucleic acids. When a position in both of the two compared sequences is occupied by the same base or amino acid monomer subunit (for instance, if a position in each of the two DNA molecules is occupied by adenine, or a position in each of two polypeptides is occupied by a lysine), then the respective molecules are identical at that position. The "percentage identity" between two sequences is a function of the number of matching positions shared by the two sequences divided by the number of positions compared ×100. For instance, if 6 of 10 of the positions in two sequences are matched, then the two sequences have 60% identity. By way of example, the DNA sequences CTGACT and CAGGTT share 50% identity (3 of the 6 total positions are matched). Generally, a comparison is made when two sequences are aligned to give maximum identity. Such alignment can be provided using, for instance, the method of Needleman et al. (1970) *J. Mol. Biol.* 48: 443-453, implemented conveniently by computer programs such as the Align program (DNAstar, Inc.). The percent identity between two amino acid sequences can also be determined using the algorithm of E. Meyers and W. Miller (*Comput. Appl. Biosci.*, 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* 48:444-453 (1970)) algorithm which has been incorporated into the GAP program in the GCG software package (Accelrys Inc., San Diego, Calif.), using either a Blossum 62 matrix or a PAM250 matrix, and a gap weight of 16, 14, 12, 10, 8, 6, or 4 and a length weight of 1, 2, 3, 4, 5, or 6.

"Similar" sequences are those which, when aligned, share identical and similar amino acid residues, where similar residues are conservative substitutions for corresponding amino acid residues in an aligned reference sequence. In this regard, a "conservative substitution" of a residue in a reference sequence is a substitution by a residue that is physically or functionally similar to the corresponding reference residue, e.g., that has a similar size, shape, electric charge, chemical properties, including the ability to form covalent or hydrogen bonds, or the like. Thus, a "conservative substitution modified" sequence is one that differs from a reference sequence or a wild-type sequence in that one or more conservative substitutions are present. The "percentage similarity" between two sequences is a function of the number of positions that contain matching residues or conservative substitutions shared by the two sequences divided by the number of positions compared ×100. For instance, if 6 of 10 of the positions in two sequences are matched and 2 of 10 positions contain conservative substitutions, then the two sequences have 80% positive similarity.

As used herein, the term "conservative sequence modifications" is intended to refer to amino acid modifications that do not negatively affect or alter the binding characteristics of the antibody containing the amino acid sequence. Such conservative sequence modifications include nucleotide and amino acid substitutions, additions and deletions. For example, modifications can be introduced by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in a particular antibody is preferably replaced with another amino acid residue from the same side chain family. Methods of identifying nucleotide and amino acid conservative substitutions which do not eliminate antigen binding are well-known in the art (see, e.g., Brummell et al., *Biochem.* 32:1180-1187 (1993); Kobayashi et al. *Protein Eng.* 12(10): 879-884 (1999); and Burks et al. *Proc. Natl. Acad. Sci. USA* 94:412-417 (1997)).

"Amino acid consensus sequence" as used herein refers to an amino acid sequence that can be generated using a matrix of at least two, and preferably more, aligned amino acid sequences, and allowing for gaps in the alignment, such that it is possible to determine the most frequent amino acid residue at each position. The consensus sequence is that sequence which comprises the amino acids which are most frequently represented at each position. In the event that two or more amino acids are equally represented at a single position, the consensus sequence includes both or all of those amino acids.

The amino acid sequence of a protein can be analyzed at various levels. For example, conservation or variability can be exhibited at the single residue level, multiple residue level, multiple residue with gaps etc. Residues can exhibit conservation of the identical residue or can be conserved at the class level. Examples of amino acid classes include polar but uncharged R groups (Serine, Threonine, Asparagine and Glutamine); positively charged R groups (Lysine, Arginine, and Histidine); negatively charged R groups (Glutamic acid and Aspartic acid); hydrophobic R groups (Alanine, Isoleucine, Leucine, Methionine, Phenylalanine, Tryptophan, Valine and Tyrosine); and special amino acids (Cysteine, Glycine and Proline). Other classes are known to one of skill in the art and may be defined using structural determinations or other data to assess substitutability. In that sense, a substitutable amino acid can refer to any amino acid which can be substituted and maintain functional conservation at that position.

It will be recognized, however, that amino acids of the same class may vary in degree by their biophysical properties. For example, it will be recognized that certain hydrophobic R groups (e.g., Alanine, Serine, or Threonine) are more hydrophilic (i.e., of higher hydrophilicity or lower hydrophobicity) than other hydrophobic R groups (e.g., Valine or Leucine). Relative hydrophilicity or hydrophobicity can be determined using art-recognized methods (see, e.g., Rose et al., *Science*, 229: 834-838 (1985) and Cornette et al., *J. Mol. Biol.*, 195: 659-685 (1987)).

As used herein, when one amino acid sequence (e.g., a first $V_H$ or $V_L$ sequence) is aligned with one or more additional amino acid sequences (e.g., one or more VH or VL sequences in a database), an amino acid position in one sequence (e.g., the first $V_H$ or $V_L$ sequence) can be compared to a "corresponding position" in the one or more additional amino acid sequences. As used herein, the "corresponding position" represents the equivalent position in the sequence(s) being compared when the sequences are optimally aligned, i.e., when the sequences are aligned to achieve the highest percent identity or percent similarity.

The term "nucleic acid molecule," refers to DNA molecules and RNA molecules. A nucleic acid molecule may be single-stranded or double-stranded, but preferably is double-stranded DNA. A nucleic acid is "operably linked" when it is placed into a functional relationship with another nucleic acid sequence. For instance, a promoter or enhancer is operably linked to a coding sequence if it affects the transcription of the sequence. In certain embodiments, the invention provides isolated nucleic acid molecules that encode an antibody of the invention, a variable light chain of the invention, and/or a variable heavy chain of the invention. In certain embodiments, a nucleic acid molecule of the invention encodes: a polypeptide comprising a light chain variable region having at least 97% identity to SEQ ID NO: 2 or SEQ ID NO: 14; a polypeptide comprising a heavy chain variable region having at least 95% identity to SEQ ID NO: 5; or an antibody having at least 96% identity to SEQ ID NO: 10 or SEQ ID NO: 17.

The term "vector," refers to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome.

The term "host cell" refers to a cell into which an expression vector has been introduced. Host cells can include bacterial, microbial, plant or animal cells. Bacteria, which are susceptible to transformation, include members of the enterobacteriaceae, such as strains of *Escherichia coli* or *Salmonella*; Bacillaceae, such as *Bacillus subtilis; Pneumococcus; Streptococcus*, and *Haemophilus influenzae*. Suitable microbes include *Saccharomyces cerevisiae* and *Pichia pastoris*. Suitable animal host cell lines include CHO (Chinese Hamster Ovary lines) and NS0 cells.

The terms "treat," "treating," and "treatment," refer to therapeutic or preventative measures described herein. The methods of "treatment" employ administration to a subject, in need of such treatment, an antibody of the present invention, for example, a subject having a TNFα-mediated disorder or a subject who ultimately may acquire such a disorder, in order to prevent, cure, delay, reduce the severity of, or ameliorate one or more symptoms of the disorder or recurring disorder, or in order to prolong the survival of a subject beyond that expected in the absence of such treatment.

The term "TNF-mediated disorder" refers generally to disease states and/or symptoms associated with TNF, including any disorder, the onset, progression or the persistence of the symptoms of which requires the participation of TNF. Examples of TNF-mediated disorders include, but are not limited to, age-related macular degeneration, neovascular glaucoma, diabetic retinopathy, retinopathy of prematurity, retrolental fibroplasia, breast carcinomas, lung carcinomas, gastric carcinomas, esophageal carcinomas, colorectal carcinomas, liver carcinomas, ovarian carcinomas, the comas, arrhenoblastomas, cervical carcinomas, endometrial carcinoma, endometrial hyperplasia, endometriosis, fibrosarcomas, choriocarcinoma, head and neck cancer, nasopharyngeal carcinoma, laryngeal carcinomas, hepatoblastoma, Kaposi's sarcoma, melanoma, skin carcinomas, hemangioma, cavernous hemangioma, hemangioblastoma, pancreas carcinomas, retinoblastoma, astrocytoma, glioblastoma, Schwannoma, oligodendroglioma, medulloblastoma, neuroblastomas, rhabdomyosarcoma, osteogenic sarcoma, leiomyosarcomas, urinary tract carcinomas, thyroid carcinomas, Wilm's tumor, renal cell carcinoma, prostate carcinoma, abnormal vascular proliferation associated with phakomatoses, edema (such as that associated with brain tumors), Meigs' syndrome, rheumatoid arthritis, psoriasis and atherosclerosis. TNF-mediated disorders also include dry eye and TNFα-related inflammatory conditions, such as ocular inflammation, allergic conjunctivitis, dermatitis, rhinitis, and asthma, for example, and include those cellular changes resulting from the activity of TNFα that leads directly or indirectly to the TNFα-related inflammatory condition. In addition, TNF-mediated disorders also include ocular angiogenesis, Bechet's disease, retinitis, glaucoma, Sjörgen syndrome, diabetic neuropathy, scleritis, keratitis and uveitis.

The term "effective dose" or "effective dosage" refers to an amount sufficient to achieve or at least partially achieve the desired effect. The term "therapeutically effective dose" is defined as an amount sufficient to cure or at least partially arrest the disease and its complications in a patient already suffering from the disease. Amounts effective for this use will depend upon the severity of the disorder being treated and the general state of the patient's own immune system.

The term "subject" refers to any human or non-human animal. For example, the methods and compositions of the present invention can be used to treat a subject with a TNF-mediated disorder.

The numbering systems as used herein to identify amino acid residue positions in antibody heavy and light chain variable regions corresponds to the one as defined by A. Honegger, J. Mol. Biol. 309 (2001) 657-670 (the AHo system). Conversion tables between the AHo system and the most commonly used system as defined by Kabat et al. (Kabat, E. A., et al. (1991) Sequences of Proteins of Immunological Interest, Fifth Edition, U.S. Department of Health and Human Services, NIH Publication No. 91-3242) are provided in A. Honegger, J. Mol. Biol. 309 (2001) 657-670.

As used herein, the term "aggregation" refers to the process of intermolecular interactions/associations between monomeric molecules in liquid solution leading to the formation of oligomeric species. Aggregation can be evaluated under stress conditions using accelerated stability studies in a concentrated solution. Accelerated stability studies are designed to increase the rate of degradation, aggregation or chemical modifications of a compound by using extreme storage conditions. Accelerated stability studies, also known as stress studies, are typically performed at 40° C. and room temperature. These stability studies provide valuable information concerning the effect of exposure to environmental conditions outside of the normal label storage conditions, also known as stress conditions. High protein concentration solutions are widely used in the pharmaceutical industry. The solution behavior of proteins at high concentrations can be markedly different from that predicted based on dilute solution analysis due to thermodynamic non-ideality in these solutions. The non-ideality observed in these systems is related to the protein-protein interactions (PPI). Different types of forces play a key role in determining the overall nature and extent of these PPI and their relative contributions are affected by solute and solvent properties. The role of PPI is driven by these intermolecular forces to govern solution characteristics, including physical stability and protein self-association and aggregation. Concentrated solutions are those solutions where PPI affects the proteins in solution by increasing the oligomerization rate. A concentrated solution can have, for example, a protein concentration of at least 10 mg/ml.

Soluble products of this process may be detected with analytical methods, such as SE-HPLC. The term "aggregation-reducing modification" as used herein refers to a modification, such as an amino acid substitution, that reduces an antibody's propensity to aggregate in a liquid solution compared with a parental antibody as described herein. A "parental" antibody is an antibody comprising essentially the same sequence as the corresponding antibody that has aggregration-reducing modifications. For example, the parental antibody may have the same CDRs as the modified antibody, and may have the exact same sequence as the modified antibody except for residues at AHo position 47 and/or 50 in the variable light chain sequence, and may further differ at AHo positions 12, 103, and 144 in the variable heavy chain sequence. Other differences may also be present, so long as the parental antibody does not contain the aggregation-reducing modifications present in the antibody modified according to a method of the invention.

The term "interface" as used herein refers to the interaction between the two variable domains (heavy and light variable domains) of an antibody. The interface includes the amino acid residues that participate directly or indirectly in the interaction between the variable domains. Such interaction includes, but is not limited to, all kinds of non-bonded interactions, for example van der Waals forces, hydrogen bonding, electrostatic terms, and hydrophobic interactions between the two domains.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

Various aspects of the invention are described in further detail in the following subsections. It is understood that the various embodiments, preferences and ranges may be combined at will. Further, depending of the specific embodiment, selected definitions, embodiments or ranges may not apply.

In one aspect, the present invention provides antibodies that bind TNFα and thus are suitable to block the function of TNFα in vivo.

In certain embodiments, antibodies of the invention are optimized with an aggregation-reducing modification(s) relative to a parental antibody, such that an antibody of the invention has a reduced propensity to aggregate compared with a parental/unmodified antibody. Such modification(s) include amino acid substitutions of particular residues that participate in the variable light chain (VL) and variable heavy chain (VH) interface. In some embodiments, the aggregation-reducing modification comprises at least one amino acid substitution that reduces the free energy of the VL-VH interface compared with the free energy of the VL-VH interface of the parental antibody in an in silico modeling approach, as described herein. Such modifications include amino acid substitutions of particular residues that contribute to the free energy of the VL-VH interface.

In certain embodiments, an aggregation-reducing modification of the invention comprises a substitution at AHo position 50 in the VL chain. In one embodiment, the substitution is an arginine (R) at AHo position 50. In another embodiment, the arginine (R) at AHo position 50 replaces a lysine (K).

In other embodiments, an aggregation-reducing modification of the invention comprises a substitution at AHo position 47 in the VL chain. In one embodiment, the substitution is an arginine (R) at AHo position 47. In another embodiment, the arginine (R) at AHo position 47 replaces a lysine (K).

The AHo numbering system is described in detail in Honegger, A. and Plückthun, A. (2001) J Mol. Biol. 309: 657-670). AHo position 50 in the variable light chain corresponds to Kabat position 42. AHo position 47 in the variable light chain corresponds to Kabat position 39. The Kabat numbering system is described further in Kabat et al. (Kabat, E. A., et al. (1991) Sequences of Proteins of Immunological Interest, Fifth Edition, U.S. Department of Health and Human Services, NIH Publication No. 91-3242).). Conversion tables between the AHo system and the most commonly used system as defined by Kabat et al are provided in A. Honegger, J. Mol. Biol. 309 (2001) 657-670.

The following conversion tables are provided for two different numbering systems used to identify amino acid residue positions in antibody heavy and light chain variable regions. The Kabat numbering system is described further in Kabat et al. (Kabat, E. A., et al. (1991) Sequences of Proteins of Immunological Interest, Fifth Edition, U.S. Department of Health and Human Services, NIH Publication No. 91-3242). The AHo numbering system is described further in Honegger, A. and Pluckthun, A. (2001) *J. Mol. Biol.* 309:657-670).

Heavy Chain Variable Region Numbering

TABLE 1

Conversion table for the residue positions in the Heavy Chain Variable Domain

| Kabat | AHo | Kabat | AHo | Kabat | AHo |
|---|---|---|---|---|---|
| 1 | 1 | 44 | 51 | 87 | 101 |
| 2 | 2 | 45 | 52 | 88 | 102 |
| 3 | 3 | 46 | 53 | 89 | 103 |
| 4 | 4 | 47 | 54 | 90 | 104 |
| 5 | 5 | 48 | 55 | 91 | 105 |
| 6 | 6 | 49 | 56 | 92 | 106 |
| 7 | 7 | 50 | 57 | 93 | 107 |
| * | 8 | 51 | 58 | 94 | 108 |
| 8 | 9 | 52 | 59 | 95 | 109 |
| 9 | 10 | 52a | 60 | 96 | 110 |
| 10 | 11 | 52b | 61 | 97 | 111 |
| 11 | 12 | 52c | 62 | 98 | 112 |
| 12 | 13 | * | 63 | 99 | 113 |
| 13 | 14 | 53 | 64 | 100 | 114 |
| 14 | 15 | 54 | 65 | 100a | 115 |

TABLE 1-continued

Conversion table for the residue positions in the Heavy Chain Variable Domain

| Kabat | AHo | Kabat | AHo | Kabat | AHo |
|---|---|---|---|---|---|
| 15 | 16 | 55 | 66 | 100b | 116 |
| 16 | 17 | 56 | 67 | 100c | 117 |
| 17 | 18 | 57 | 68 | 100d | 118 |
| 18 | 19 | 58 | 69 | 100e | 119 |
| 19 | 20 | 59 | 70 | 100f | 120 |
| 20 | 21 | 60 | 71 | 100g | 121 |
| 21 | 22 | 61 | 72 | 100h | 122 |
| 22 | 23 | 62 | 73 | 100i | 123 |
| 23 | 24 | 63 | 74 | * | 124 |
| 24 | 25 | 64 | 75 | * | 125 |
| 25 | 26 | 65 | 76 | * | 126 |
| 26 | 27 | 66 | 77 | * | 127 |
| * | 28 | 67 | 78 | * | 128 |
| 27 | 29 | 68 | 79 | * | 129 |
| 28 | 30 | 69 | 80 | * | 130 |
| 29 | 31 | 70 | 81 | * | 131 |
| 30 | 32 | 71 | 82 | * | 132 |
| 31 | 33 | 72 | 83 | * | 133 |
| 32 | 34 | 73 | 84 | * | 134 |
| 33 | 35 | 74 | 85 | * | 135 |
| 34 | 36 | 75 | 86 | * | 136 |
| 35 | 37 | 76 | 87 | 101 | 137 |
| 35a | 38 | 77 | 88 | 102 | 138 |
| 35b | 39 | 78 | 89 | 103 | 139 |
| * | 40 | 79 | 90 | 104 | 140 |
| * | 41 | 80 | 91 | 105 | 141 |
| * | 42 | 81 | 92 | 106 | 142 |
| 36 | 43 | 82 | 93 | 107 | 143 |
| 37 | 44 | 82a | 94 | 108 | 144 |
| 38 | 45 | 82b | 95 | 109 | 145 |
| 39 | 46 | 82b | 96 | 110 | 146 |
| 40 | 47 | 83 | 97 | 111 | 147 |
| 41 | 48 | 84 | 98 | 112 | 148 |
| 42 | 49 | 85 | 99 | 113 | 149 |
| 43 | 50 | 86 | 100 | | |

Column 1, Residue position in Kabat's numbering system.
Column 2, Corresponding number in AHo's numbering system for the position indicated in column 1.
Column 3, Residue position in Kabat's numbering system.
Column 4, Corresponding number in AHo's numbering system for the position indicated in column 3.
Column 5, Residue position in Kabat's numbering system.
Column 6, Corresponding number in AHo's numbering system for the position indicated in column 5

Light Chain Variable Region Numbering

TABLE 2

Conversion table for the residue positions in the Light Chain Variable Domain

| Kabat | AHo | Kabat | AHo | Kabat | AHo |
|---|---|---|---|---|---|
| 1 | 1 | 43 | 51 | 83 | 101 |
| 2 | 2 | 44 | 52 | 84 | 102 |
| 3 | 3 | 45 | 53 | 85 | 103 |
| 4 | 4 | 46 | 54 | 86 | 104 |
| 5 | 5 | 47 | 55 | 87 | 105 |
| 6 | 6 | 48 | 56 | 88 | 106 |
| 7 | 7 | 49 | 57 | 89 | 107 |
| 8 | 8 | 50 | 58 | 90 | 108 |
| 9 | 9 | * | 59 | 91 | 109 |
| 10 | 10 | * | 60 | 92 | 110 |
| 11 | 11 | * | 61 | 93 | 111 |
| 12 | 12 | * | 62 | 94 | 112 |
| 13 | 13 | * | 63 | 95 | 113 |
| 14 | 14 | * | 64 | 95a | 114 |
| 15 | 15 | * | 65 | 95b | 115 |
| 16 | 16 | * | 66 | 95c | 116 |
| 17 | 17 | 51 | 67 | 95d | 117 |
| 18 | 18 | 52 | 68 | 95e | 118 |
| 19 | 19 | 53 | 69 | 95f | 119 |
| 20 | 20 | 54 | 70 | * | 120 |
| 21 | 21 | 55 | 71 | * | 121 |
| 22 | 22 | 56 | 72 | * | 122 |
| 23 | 23 | 57 | 73 | * | 123 |
| 24 | 24 | 58 | 74 | * | 124 |
| 25 | 25 | 59 | 75 | * | 125 |
| 26 | 26 | 60 | 76 | * | 126 |
| 27 | 27 | 61 | 77 | * | 127 |
| * | 28 | 62 | 78 | * | 128 |
| 27a | 29 | 63 | 79 | * | 129 |
| 27b | 30 | 64 | 80 | * | 130 |
| 27c | 31 | 65 | 81 | * | 131 |
| 27d | 32 | 66 | 82 | * | 132 |
| 27e | 33 | 67 | 83 | * | 133 |
| 27f | 34 | 68 | 84 | * | 134 |
| * | 35 | * | 85 | * | 135 |
| 28 | 36 | * | 86 | * | 136 |
| 29 | 37 | 69 | 87 | 96 | 137 |
| 30 | 38 | 70 | 88 | 97 | 138 |
| 31 | 39 | 71 | 89 | 98 | 139 |
| 32 | 40 | 72 | 90 | 99 | 140 |
| 33 | 41 | 73 | 91 | 100 | 141 |
| 34 | 42 | 74 | 92 | 101 | 142 |
| 35 | 43 | 75 | 93 | 102 | 143 |
| 36 | 44 | 76 | 94 | 103 | 144 |
| 37 | 45 | 77 | 95 | 104 | 145 |
| 38 | 46 | 78 | 96 | 105 | 146 |
| 39 | 47 | 79 | 97 | 106 | 147 |
| 40 | 48 | 80 | 98 | 107 | 148 |
| 41 | 49 | 81 | 99 | 108 | 149 |
| 42 | 50 | 82 | 100 | | |

Column 1, Residue position in Kabat's numbering system.
Column 2, Corresponding number in AHo's numbering system for the position indicated in column 1.
Column 3, Residue position in Kabat's numbering system.
Column 4, Corresponding number in AHo's numbering system for the position indicated in column 3.
Column 5, Residue position in Kabat's numbering system.
Column 6, Corresponding number in AHo's numbering system for the position indicated in column 5

The antibodies of the invention can comprise additional modifications as desired. For example, an antibody of the invention can comprise amino acid substitutions to reduce its immunogenicity in vivo according to the methods described, for example, in U.S. patent application Ser. No. 12/973,968 and/or substitutions for enhancing the solubility of the antibody, as described in WO 09/155,725. Thus, in one embodiment, an antibody of the invention comprises Serine (S) at heavy chain position 12 (AHo numbering); Serine (S) or Threonine (T) at heavy chain position 103 (AHo numbering) and/or Serine (S) or Threonine (T) at heavy chain position 144 (AHo numbering). Additionally, the antibody can comprise Serine (S) or Threonine (T) at heavy chain positions 97, 98 and/or 99 (AHo numbering). Preferably, the antibody comprises Serine (S) at heavy chain position 12 (AHo numbering), Threonine (T) at heavy chain position 103 (AHo numbering) and Threonine (T) at heavy chain position 144 (AHo numbering).

In one embodiment, an antibody of the invention comprises the variable light chain:

SEQ ID NO: 1
EIVMTQSPSTLSASVGDRVIITC$(X)_{n\ =\ 1\text{-}50}$ WYQQKPGRAPKL

LIY$(X)_{n\ =\ 1\text{-}50}$ GVPSRFSGSGSGAEFTLTISSLQPDDFATYYC $(X)_{n\ =\ 1\text{-}50}$ FGQGTKLTVLG In a preferred embodiment, an antibody of the invention comprises the variable light chain (the CDRs are underlined):

SEQ ID NO: 2:
EIVMTQSPSTLSASVGDRVIITCQSSQSVYGNIWMAWYQQKPGRAPKLLI

YQASKLASGVPSRFSGSGSGAEFTLTISSLQPDDFATYYCQGNFNTGDRY

AFGQGTKLTVLG

In another embodiment, an antibody of the invention comprises the variable heavy chain:

SEQ ID NO. 3: variable heavy chain framework
EVQLVESGGGLVQPGGSLRLSCTAS(X)$_{n\ =\ 1-50}$ WVRQAPGKGLE WVG(X)$_{n\ =\ 1-50}$ RFTISRDTSKNTVYLQMNSLRAEDTAVYYCAR (X)$_{n\ =\ 1-50}$ WGQGTLVTVSS In still another embodiment, an antibody of the invention comprises the variable heavy chain framework SEQ ID NO: 4: variable heavy chain framework
EVQLVESGGGLVQPGGSLRLSCTVS(X)$_{n\ =\ 1-50}$ WVRQAPGKGLE WVG(X)$_{n\ =\ 1-50}$ RFTISKDTSKNTVYLQMNSLRAEDTAVYYCAR (X)$_{n\ =\ 1-50}$ WGQGTLVTVSS In a preferred embodiment, the antibody of the invention comprises the variable heavy chain (the CDRs are underlined):

SEQ ID NO: 5:
EVQLVESGGGSVQPGGSLRLSCTASGFTISRSYWICWVRQAPGKGLEWVG

CIYGDNDITPLYANWAKGRFTISRDTSKNTVYLQMNSLRAEDTATYYCAR

LGYADYAYDLWGQGTTVTVSS

As used herein, X residues are CDR insertion sites. X may be any naturally occurring amino acid; at least three and up to 50 amino acids can be present.

In one embodiment, the variable light chain framework of an antibody of the invention comprises SEQ ID NO: 1 and the variable heavy chain framework comprises SEQ ID NO: 3 or SEQ ID NO: 4.

In another embodiment, the variable light chain framework of an antibody of the invention comprises a sequence having at least 65% identity, more preferably at least 80%, 85%, 90%, 95%, 96%, 97%, 98%, more preferably 99% identity, to SEQ ID NO: 1. Most preferably said sequence has an arginine (R) at AHo position 50. In another embodiment, said sequence has an arginine (R) at AHo position 47.

In another embodiment, the variable heavy chain framework of an antibody of the invention comprises a sequence having at least 80% identity, more preferably at least 85%, 90%, 91%, 92%, 93%, 94%, 95%, 96%, 97%, 98%, more preferably 99% identity, to SEQ ID No. 3. Preferably, said antibody comprises Serine (S) at heavy chain position 12 (AHo numbering), Threonine (T) at heavy chain position 103 (AHo numbering) and Threonine (T) at heavy chain position 144 (AHo numbering).

In another embodiment, the variable light chain framework of an antibody of the invention comprises a sequence having at least 97%, 98%, more preferably 99% identity, to SEQ ID NO: 2 or SEQ ID NO: 14.

In another embodiment, the variable heavy chain framework of an antibody of the invention comprises a sequence having at least 95%, 96%, 97%, 98%, more preferably 99% identity, to SEQ ID NO: 5.

In another embodiment, an antibody of the invention comprises a sequence having at least 96%, 97%, 98%, more preferably 99% identity, to SEQ ID NO: 10 or SEQ ID NO: 17.

In another embodiment, the variable light chain framework of an antibody of the invention comprises SEQ ID NO: 2 or SEQ ID NO: 14, and the variable heavy chain framework comprises SEQ ID NO: 5.

In one embodiment, antibodies and antibody fragments of the present invention are single-chain antibodies (scFv) or Fab fragments. In the case of scFv antibodies, a VL domain can be linked to a VH domain in either orientation by a flexible linker. A suitable state of the art linker consists of repeated GGGGS (SEQ ID NO: 6) amino acid sequences or variants thereof. In a preferred embodiment of the present invention a (GGGGS)$_4$ (SEQ ID NO: 7) linker or its derivative is used, but variants of 1-3 repeats are also possible (Holliger et al. (1993), Proc. Natl. Acad. Sci. USA 90:6444-6448). Other linkers that can be used for the present invention are described by Alfthan et al. (1995), Protein Eng. 8:725-731, Choi et al. (2001), Eur. J. Immunol. 31:94-106, Hu et al. (1996), Cancer Res. 56:3055-3061, Kipriyanov et al. (1999), J. Mol. Biol. 293:41-56 and Roovers et al. (2001), Cancer Immunol. Immunother. 50:51-59. The arrangement can be either VL-linker-VH or VH-linker-VL, with the former orientation being the preferred one. In the case of Fab fragments, selected light chain variable domains VL are fused to the constant region of a human Ig kappa chain, while the suitable heavy chain variable domains VH are fused to the first (N-terminal) constant domain CH1 of a human IgG. At the C-terminus, an inter-chain disulfide bridge is formed between the two constant domains.

Thus, in one embodiment, an antibody of the invention comprises the sequence:

SEQ ID NO: 8
EIVMTQSPSTLSASVGDRVIITC(X)$_{n\ =\ 1-50}$WYQQKPGRAPKLLIY (X)$_{n\ =\ 1-50}$GVPSRFSGSGSGTEFTLTISSLQPDDFATYYC (X)$_{n\ =\ 1-50}$FGQGTKLTVLGGGGSGGGGSGGGGSGGGGSEVQLVES

GGGLVQPGGSLRLSCTAS(X)$_{n\ =\ 1-50}$WVRQAPGKGLEWVG (X)$_{n\ =\ 1-50}$RFTISRDTSKNTVYLQMNSLRAEDTAVYYCAR (X)$_{n\ =\ 1-50}$WGQGTLVTVSS

In another embodiment, an antibody of the invention comprises the sequence:

SEQ ID NO: 9
EIVMTQSPSTLSASVGDRVIITC(X)$_{n\ =\ 1-50}$WYQQRPGKAPKLLIY (X)$_{n\ =\ 1-50}$GVPSRFSGSGSGTEFTLTISSLQPDDFATYYC (X)$_{n\ =\ 1-50}$FGQGTKLTVLGGGGSGGGGSGGGGSGGGGSEVQLVES

GGGLVQPGGSLRLSCTVS(X)$_{n\ =\ 1-50}$WVRQAPGKGLEWVG (X)$_{n\ =\ 1-50}$RFTISKDTSKNTVYLQMNSLRAEDTAVYYCAR (X)$_{n\ =\ 1-50}$WGQGTLVTVSS

In a preferred embodiment, an antibody of the invention comprises the sequence:

SEQ ID NO: 10
(34rFW1.4_VL_K50R_DHP):
EIVMTQSPSTLSASVGDRVIITCQSSQSVYGNIWMAWYQQKPGRAPKLLI

YQASKLASGVPSRFSGSGSGAEFTLTISSLQPDDFATYYCQGNFNTGDRY

AFGQGTKLTVLGGGGSGGGGSGGGGSGGGGSEVQLVESGGGSVQPGGSL

RLSCTASGFTISRSYWICWVRQAPGKGLEWVGCIYGDNDITPLYANWAKG

RFTISRDTSKNTVYLQMNSLRAEDTATYYCARLGYADYAYDLWGQGTTVT

VSS

In one embodiment, an antibody of the invention comprises the variable light chain:

SEQ ID NO. 11: variable light chain framework of FW1.4 (KI27)
EIVMTQSPSTLSASVGDRVIITC (X)n = 1-50 WYQQKPGKAPKLLI Y (X)n = 1-50 GVPSRFSGSGSGAEFTLTISSLQPDDFATYYC (X)n = 1-50 FGQGTKLTVLG In another embodiment, an antibody of the invention comprises the variable light chain:

SEQ ID NO. 12: substituted variable light chain framework of FW1.4
EIVMTQSPSTLSASVGDRVIITC(X)n = 1-50 WYQQKPGKAPKLLIY (X)n = 1-50 GVPSRFSGSGSGTEFTLTISSLQPDDFATYYC (X)n = 1-50 FGQGTKLTVLG In still another preferred embodiment, an antibody of the invention comprises the sequence:

SEQ ID NO: 13
EIVMTQSPSTLSASVGDRVIITC(X)$_{n\,=\,1\text{-}50}$WYQQRPGKAPKLLIY (X)$_{n\,=\,1\text{-}50}$GVPSRFSGSGSGAEFTLTISSLQPDDFATYYC (X)$_{n\,=\,1\text{-}50}$ FGQGTKLTVLG In another embodiment, an antibody of the invention comprises the variable light chain (the CDRs are underlined):

SEQ ID NO: 14:
EIVMTQSPSTLSASVGDRVIITCQSSQSVYGNIWMAWYQQRPGKAPKLLI

YQASKLASGVPSRFSGSGSGAEFTLTISSLQPDDFATYYCQGNFNTGDRY

AFGQGTKLTVL

Thus, in one embodiment, an antibody of the invention comprises the sequence:

SEQ ID NO: 15:
EIVMTQSPSTLSASVGDRVIITC(X)$_{n\,=\,1\text{-}50}$WYQQRPGKAPKLLIY (X)$_{n\,=\,1\text{-}50}$GVPSRFSGSGSGTEFTLTISSLQPDDFATYYC (X)$_{n\,=\,1\text{-}50}$FGQGTKLTVLGGGGSGGGGSGGGGSGGGGSEVQLVESG GGLVQPGGSLRLSCTAS(X)$_{n\,=\,1\text{-}50}$WVRQAPGKGLEWVG (X)$_{n\,=\,1\text{-}50}$RFTISRDTSKNIVYLQMNSLRAEDTAVYYCAR (X)$_{n\,=\,1\text{-}50}$WGQGTLVTVSS In another embodiment, an antibody of the invention comprises the sequence:

SEQ ID NO: 16:
EIVMTQSPSTLSASVGDRVIITC(X)$_{n\,=\,1\text{-}50}$WYQQRPGKAPKLLIY (X)$_{n\,=\,1\text{-}50}$GVPSRFSGSGSGTEFTLTISSLQPDDFATYYC (X)$_{n\,=\,1\text{-}50}$FGQGTKLTVLGGGGSGGGGSGGGGSGGGGSEVQLVESG GGLVQPGGSLRLSCTVS(X)$_{n\,=\,1\text{-}50}$WVRQAPGKGLEWVG (X)$_{n\,=\,1\text{-}50}$RFTISKDTSKNIVYLQMNSLRAEDTAVYYCAR (X)$_{n\,=\,1\text{-}50}$WGQGTLVTVSS In one embodiment, an antibody of the invention comprises the sequence:

SEQ ID NO: 17
(34rFW1.4_VL_K47R_DHP):
EIVMTQSPSTLSASVGDRVIITCQSSQSVYGNIWMAWYQQRPGKAPKLLI

YQASKLASGVPSRFSGSGSGAEFTLTISSLQPDDFATYYCQGNFNTGDRY

AFGQGTKLTVLGGGGSGGGGSGGGGSGGGGSEVQLVESGGGSVQPGGSL

RLSCTASGFTISRSYWICWVRQAPGKGLEWVGCIYGDNDITPLYANWAKG

RFTISRDTSKNTVYLQMNSLRAEDTATYYCARLGYADYAYDLWGQGTTVT

VSS

In yet another embodiment, an antibody of the invention comprises the sequence:

SEQ ID NO: 18
(34rFW1.4)
EIVMTQSPSTLSASVGDRVIITCQSSQSVYGNIWMAWYQQKPGKAPKLLI

YQASKLASGVPSRFSGSGSGAEFTLTISSLQPDDFATYYCQGNFNTGDRY

AFGQGTKLTVLGGGGSGGGGSGGGGSGGGGSEVQLVESGGGSVQPGGSL

RLSCTASGFTISRSYWICWVRQAPGKGLEWVGCIYGDNDITPLYANWAKG

RFTISRDTSKNTVYLQMNSLRAEDTATYYCARLGYADYAYDLWGQGTTVT

VSS

In one embodiment, the VL of a parental antibody is or comprises SEQ ID NO: 11 or SEQ ID NO: 12 or a sequence having at least 65% identity, more preferably, 80%, 85%, 90%, 95%, 96%, 97%, 98%, more preferably 99% to SEQ ID NO: 11 or SEQ ID NO: 12. In another preferred embodiment, the VH of the parental antibody is or comprises SEQ ID NO: 3 or SEQ ID NO: 4 a sequence having at least 80% identity, more preferably, 85%, 90%, 95%, 96%, 97%, 98%, more preferably 99% to SEQ ID NO: 3 or SEQ ID NO: 4.

An antibody of the invention that comprises an aggregation-reducing modification preferably comprises one or more CDRs from a rabbit antibody. As known in the art, rabbit CDRs are different from human or rodent CDRs: they can contain cysteine residues that become disulphide linked to the framework or form interCDR S—S bridges. Moreover, rabbit CDRs often do not belong to any previously known canonical structure.

The present invention also features bivalent and bispecific molecules comprising an anti-TNFα antibody, or a fragment thereof, of the invention. An antibody of the invention, or antigen-binding portions thereof, can be derivatized or linked to another functional molecule, e.g., another peptide or protein (e.g., another antibody or ligand for a receptor) to generate a bispecific molecule that binds to at least two different binding sites or target molecules. The antibody of the invention may be derivatized or linked to more than one other functional molecule to generate multispecific molecules that bind to more than two different binding sites and/or target molecules; such multispecific molecules are also intended to be encompassed by the term "bispecific molecule" as used herein. Non-limiting examples of bispecific molecules include a diabody, a single-chain diabody, and a tandem antibody, as known to those of skill in the art.

To create a bispecific molecule of the invention, an antibody of the invention can be functionally linked (e.g., by chemical coupling, genetic fusion, noncovalent association or otherwise) to one or more other binding molecules, such as another antibody, antibody fragment, tumor specific or pathogen specific antigens, peptide or binding mimetic, such that a bispecific molecule results. Accordingly, the present invention includes bispecific molecules comprising at least one first binding molecule having specificity for TNFα and a second binding molecule having specificity for one or more additional target epitope.

In one embodiment, the bispecific molecules of the invention comprise a binding specificity at least one antibody, or an antibody fragment thereof, including, e.g., an Fab, Fab', F(ab')$_2$, Fv, or a single chain Fv. The antibody may also be a light chain or heavy chain dimer, or any minimal fragment thereof such as a Fv or a single chain construct as described in Ladner et al. U.S. Pat. No. 4,946,778, the contents of which are expressly incorporated by reference.

While human monoclonal antibodies are preferred, other antibodies which can be employed in the bispecific molecules of the invention are murine, chimeric and humanized monoclonal antibodies.

The bispecific molecules of the present invention can be prepared by conjugating the constituent binding specificities using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohaxane-1-carboxylate (sulfo-SMCC) (see e.g., Karpovsky et al. (1984) *J. Exp. Med.* 160:1686; Liu, M A et al. (1985) *Proc. Natl. Acad. Sci. USA* 82:8648). Other methods include those described in Paulus (1985) Behring Ins. Mitt. No. 78, 118-132; Brennan et al. (1985) *Science* 229:81-83), and Glennie et al. (1987) *J. Immunol.* 139: 2367-2375). Preferred conjugating agents are SATA and sulfo-SMCC, both available from Pierce Chemical Co. (Rockford, Ill.).

When the binding specificities are antibodies, they can be conjugated via sulfhydryl bonding, for example, via the C-terminus hinge regions of the two heavy chains or other sites, whether naturally occurring or introduced artificially. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab')$_2$ or ligand×Fab fusion protein. A bispecific molecule of the invention can be a single chain molecule comprising one single chain antibody and a binding determinant, or a single chain bispecific molecule comprising two binding determinants. Bispecific molecules may comprise at least two single chain molecules. Further, a bispecfic molecule may be a scFv that specifically binds to first target, wherein the VH and VL of said scFv are linked with a flexible linker comprising a domain providing specific binding to a second target. Suitable linkers are described, for example, in International Patent Application WO 2010/006454. Methods for preparing bispecific molecules are described for example in U.S. Pat. Nos. 5,260,203; 5,455,030; 4,881,175; 5,132,405; 5,091,513; 5,476,786; 5,013,653; 5,258,498; and 5,482,858.

Binding of the bispecific molecules to their specific targets can be confirmed by, for example, enzyme-linked immunosorbent assay (ELISA), radioimmunoassay (RIA), FACS analysis, bioassay (e.g., growth inhibition), or by immunoblot assay. Each of these assays generally detects the presence of protein-antibody complexes of particular interest by employing a labeled reagent (e.g., an antibody) specific for the complex of interest. For example, the TNF-antibody complexes can be detected using e.g., an enzyme-linked antibody or antibody fragment which recognizes and specifically binds to the antibody-TNF complexes. Alternatively, the complexes can be detected using any of a variety of other immunoassays. For example, the antibody can be radioactively labeled and used in a radioimmunoassay (RIA) (see, for example, Weintraub, B., *Principles of Radioimmunoassays*, Seventh Training Course on Radioligand Assay Techniques, The Endocrine Society, March, 1986, which is incorporated by reference herein). The radioactive isotope can be detected by such means as the use of a γ counter or a scintillation counter or by autoradiography.

In another aspect, the invention provides a method for producing the antibodies described herein. The methods for producing antibodies having reduced propensity for aggregating in solution as provided herein are based on the surprising observation that through modulation of the antibody domain interaction between the light chain and heavy chain, aggregation propensity of antibodies can be reduced, and that aggregation-reducing mutations can be reliably predicted by determining the free energy of the VL/VH interface defined as the difference between the energy of the antibody (such as an scFv) and the individual variable domains. As shown herein, aggregation-reducing substitutions that modulate antibody domain interaction by lowering the free energy between the variable domains can be made without affecting stability or binding activity of the antibody.

In one embodiment, a method of the invention comprises the steps of:
  (i) providing an antibody comprising a variable light chain (VL) and a variable heavy chain (VH);
  (ii) identifying one or more residue position participating in the interface between the variable light chain (VL) and the variable heavy chain (VH) of the antibody; and
  (iii) modifying the antibody by introducing a substitution at the identified residue position(s) such that the substitution(s) reduces the free energy between the VL and the VH domains by at least 0.5 kcal/mol, preferably at least 1.0 kcal/mol, and most preferably at least 2.0 kcal/mol (i.e., the free energy between the VL and VH domains with the substitution is at least 0.5 kcal/mol less than the free energy between the corresponding VL and VH domains that do not comprise the amino acid substitution), thereby reducing the aggregation propensity of the modified antibody compared with that of a parental antibody.

As outlined above, the antibody can be, for example, a Fab, Fab', a F(ab)'2, single-chain Fv (scFv), an Fv fragment, a diabody, a single-chain diabody, a tandem antibody, or a linear antibody; in a preferred embodiment, the antibody is a single-chain Fv (scFv).

In a preferred embodiment, the identification of the one or more residue positions participating in the interface between the variable light chain and the variable heavy chain of the antibody (i.e. step (ii)) involves the determination of the free energy between the VL-VH interface. This can be performed by using commonly known bioinformatic programs. One example of a suitable bioinformatic program is CHARMM (Chemistry at HARvard Macromolecular Mechanics).

For the purpose of determining the free energy between the VL-VH interface, typically, a full atomistic molecular presentation of the protein is provided. The free energy of the interface is the energy difference between the entire antibody comprising both variable domains VL and VH and the sum of the energies of the individual domains in the context of an implicit solvent method. This involves three single energy calculations, (1) on the antibody G(a); (2) on the VL G(b); and (3) on the VH G(c). Accordingly, the free energy of the interface is $$G \text{ interface}=G(a)-G(b)-G(c)$$

In one embodiment, the implicit solvent method is GBMV or PBSA as known in the art.

The free energy determination may further comprise the step of simulating the charge distribution of the protein. Said charge distribution can be simulated based on electrostatic or van der Waals forces.

To determine a suitable modification, one or more amino acid residues participating in the interface can be chosen for substitution. For example, a molecular model of the protein comprising the one or more substitutions (e.g., changing one or more residues to alanine) at the selected positions is generated and the free energy of the interface of the substituted molecular presentation is determined. If the free energy of the interface of the substituted molecular model is lower than the free energy of the interface of the initial molecular model, the amino acid residue is selected for substitution. Within the context of CHARMm, mutations can be constructed, for example, with the Build Mutants protocol. The one or more substitutions in the molecular model can be at positions that are known or suspected to be involved in the VL/VH interface.

In one embodiment, an additional step of energy minimization of the molecular model comprising the one or more substitutions at the selected position(s) in the area around the mutation(s) is performed. Said area can be set to 10 Angstroms.

In one embodiment, a residue position identified for substitution is occupied by a charged amino acid.

An antibody produced by a method of the invention can comprise any suitable variable light chain or heavy chain as known in the art, and preferably comprises at least one CDR from a rabbit antibody. Certain preferred variable light and heavy chains are described herein. For example, an antibody of the invention can comprise: a VL antibody framework having at least 65% identity, more preferably 80%, 85%, 90%, 95%, 96%, 97%, 98%, more preferably 99% to SEQ ID NO: 11 or SEQ ID NO: 12, further comprising arginine (R) at AHo position 47 and/or at AHo position 50 of the variable light chain; and a VH antibody framework having at least 80% identity, more preferably, 85%, 90%, 95%, 96%, 97%, 98%, more preferably 99% to SEQ ID NO: 3.

The modification of the one or more residue positions is preferably done according to the teachings of PCT/CH2008/000285, which is incorporated herein by reference in its entirety. Briefly, for a given antibody subtype, certain amino acids are present at specific residue positions of the antibody framework. For example, a) for a human VH3 family heavy chain variable region, the preferred amino acids are:
   (i) glutamine (Q) at amino acid position 1 using AHo or Kabat numbering system;
   (ii) glutamine (Q) at amino acid position 6 using AHo or Kabat numbering system;
   (iii) threonine (T) or alanine (A) at amino acid position 7 using AHo or Kabat numbering system;
   (iv) alanine (A), valine (V), or phenylalanine (F) at amino acid position 89 using AHo numbering system (amino acid position 78 using Kabat numbering system); and/or
   (v) arginine (R), glutamine (Q), isoleucine (I), leucine (L), methionine (M) or phenylalanine (F) at amino acid position 103 using AHo numbering system (amino acid position 89 using Kabat numbering);

b) for a human VH1 a family heavy chain variable region, the preferred amino acids are:
   (i) glutamic acid (E) at amino acid position 1 using AHo or Kabat numbering system;
   (ii) glutamic acid (E) at amino acid position 6 using AHo or Kabat numbering system;
   (iii) leucine (L) at amino acid position 12 using AHo numbering system (amino acid position 11 using Kabat numbering system);
   (iv) methionine (M) at amino acid position 13 using AHo numbering system (amino acid position 12 using Kabat numbering system):
   (v) glutamic acid (E) or glutamine (Q) at amino acid position 14 using AHo numbering system (amino acid position 13 using Kabat numbering system);
   (vi) leucine (L) at amino acid position 19 using AHo numbering system (amino acid position 18 using Kabat numbering system);
   (vii) isoleucine (I) at amino acid position 21 using AHo numbering system (amino acid position 20 using Kabat numbering system);
   (viii) phenylalanine (F), serine (S), histidine (H) or aspartic acid (D) at amino acid position 90 using AHo numbering system (amino acid position 79 using Kabat numbering system);
   (ix) aspartic acid (D) or glutamine (Q) at amino acid position 92 using AHo numbering system (amino acid position 81 using Kabat numbering system);
   (x) glycine (G), asparagine (N) or threonine (T) at amino acid position 95 using AHo numbering system (amino acid position 82b using Kabat numbering system); and/or
   (xi) threonine (T), alanine (A), proline (P) or phenylalanine (F) at amino acid position 98 using AHo numbering (amino acid position 84 using Kabat numbering);

c) for a human VH1b family heavy chain variable region, preferred amino acids are:
   (i) glutamic acid (E) at amino acid position 1 using AHo or Kabat numbering system;

(ii) threonine (T), proline (P), valine (V) or aspartic acid (D) at amino acid position 10 using AHo numbering system (amino acid position 9 using Kabat numbering system);
(iii) leucine (L) at amino acid position 12 using AHo numbering system (amino acid position 11 using Kabat numbering system);
(iv) valine (V), arginine (R), glutamine (Q) or methionine (M) at amino acid position 13 using AHo numbering system (amino acid position 12 using Kabat numbering system):
(v) glutamic acid (E), arginine (R) or methionine (M) at amino acid position 14 using AHo numbering system (amino acid position 13 using Kabat numbering system);
(vi) arginine (R), threonine (T), or asparagine (N) at amino acid position 20 using AHo numbering system (amino acid position 19 using Kabat numbering system);
(vii) isoleucine (I), phenylalanine (F), or leucine (L) at amino acid position 21 using AHo numbering system (amino acid position 20 using Kabat numbering system);
(viii) lysine (K) at amino acid position 45 using AHo numbering system (amino acid position 38 using Kabat numbering system);
(ix) threonine (T), proline (P), valine (V) or arginine (R) at amino acid position 47 using AHo numbering system (amino acid position 40 using Kabat numbering system);
(x) lysine (K), histidine (H) or glutamic acid (E) at amino acid position 50 using AHo numbering system (amino acid position 43 using Kabat numbering system);
(xi) isoleucine (I) at amino acid position 55 using AHo numbering (amino acid position 48 using Kabat numbering);
(xii) lysine (K) at amino acid position 77 using AHo numbering (amino acid position 66 using Kabat numbering);
(xiii) alanine (A), leucine (L) or isoleucine (I) at amino acid position 78 using AHo numbering system (amino acid position 67 using Kabat numbering system);
(xiv) glutamic acid (E), threonine (T) or alanine (A) at amino acid position 82 using AHo numbering system (amino acid position 71 using Kabat numbering system);
(xv) threonine (T), serine (S) or leucine (L) at amino acid position 86 using AHo numbering system (amino acid position 75 using Kabat numbering system);
(xvi) aspartic acid (D), asparagine (N) or glycine (G) at amino acid position 87 using AHo numbering system (amino acid position 76 using Kabat numbering system); and/or
(xvii) asparagine (N) or serine (S) at amino acid position 107 using AHo numbering system (amino acid position 93 using Kabat numbering system);
d) for a human Vkappa1 family light chain variable region, preferred amino acids are:
(i) glutamic acid (E) or isoleucine (I) at amino acid position 1 using AHo or Kabat numbering system;
(ii) valine (V) or isoleucine (I) at amino acid position 3 using AHo or Kabat numbering system;
(iii) valine (V), leucine (L) or isoleucine (I) at amino acid position 4 using AHo or Kabat numbering system;
(iv) glutamine (Q) at amino acid position 24 using AHo or Kabat numbering system;
(v) arginine (R) or isoleucine (I) at amino acid position 47 using AHo numbering system (amino acid position 39 using Kabat numbering system);
(vi) arginine (R), glutamic acid (E) threonine (T), methionine (M) or glutamine (Q) at amino acid position 50 using AHo numbering system (amino acid position 42 using Kabat numbering system);
(vii) histidine (H), serine (S) or phenylalanine (F) at amino acid position 57 using AHo numbering system (amino acid position 49 using Kabat numbering system);
(viii) phenylalanine (F) at amino acid position 91 using AHo numbering system (amino acid position 73 using Kabat numbering system); and/or
(ix) valine (V), serine (S), glycine (G) or isoleucine (I) at amino acid position 103 using AHo numbering system (amino acid position 85 using Kabat numbering system);
e) for a human Vkappa3 family light chain variable region, the preferred amino acids are:
(i) threonine (T) at amino acid position 2 using AHo or Kabat numbering system;
(ii) threonine (T) at amino acid position 3 using AHo or Kabat numbering system;
(iii) isoleucine (I) at amino acid position 10 using AHo or Kabat numbering system;
(iv) tyrosine (Y) at amino acid position 12 using AHo or Kabat numbering system;
(v) serine (S) at amino acid position 18 using AHo or Kabat numbering system;
(vi) alanine (A) at amino acid position 20 using AHo or Kabat numbering system;
(vii) methionine (M) at amino acid position 56 using AHo numbering system (amino acid position 48 using Kabat numbering system);
(viii) valine (V) or threonine (T) at amino acid position 74 using AHo numbering system (amino acid position 58 using Kabat numbering system);
(ix) asparagine (N) at amino acid position 94 using AHo numbering system (amino acid position 76 using Kabat numbering system);
(x) tyrosine (Y) or serine (S) at amino acid position 101 using AHo numbering system (amino acid position 83 using Kabat numbering system); and/or
(xi) leucine (L) or alanine (A) at amino acid position 103 using AHo numbering (amino acid position 85 using Kabat numbering);
f) for a human Vlambda1 family light chain variable region, preferred amino acids are:
(i) leucine (L), serine (S) or glutamic acid (E) at amino acid position 1 using AHo or Kabat numbering system;
(ii) alanine (A), proline (P), isoleucine (I) or tyrosine (Y) at amino acid position 2 using AHo or Kabat numbering system;
(iii) valine (V) or methionine (M) at amino acid position 4 using AHo or Kabat numbering system;
(iv) glutamic acid (E) at amino acid position 7 using AHo or Kabat numbering system;
(v) alanine (A) at amino acid position 11 using AHo or Kabat numbering system;
(vi) threonine (T) or serine (S) at amino acid position 14 using AHo or Kabat numbering system;
(vii) histidine (H) at amino acid position 46 using AHo numbering system (amino acid position 38 using Kabat numbering system);

(viii) threonine (T), serine (S), asparagine (N), glutamine (Q) or proline (P) at amino acid position 53 using AHo numbering system (amino acid position 45 using Kabat numbering system);

(ix) arginine (R) or glutamine (Q) at amino acid position 82 using AHo numbering system (amino acid position 66 using Kabat numbering system);

(x) glycine (G), threonine (T) or aspartic acid (D) at amino acid position 92 using AHo numbering system (amino acid position 74 using Kabat numbering system); and/or (xi) valine (V), threonine (T), histidine (H) or glutamic acid (E) at amino acid position 103 using AHo numbering (amino acid position 85 using Kabat numbering).

Accordingly, substitutions made in the present method preferably follow the teachings of PCT/CH2008/000285. The subtype determination is known to the person skilled in the art.

In one embodiment, a method of the invention comprises modification of an antibody at AHo position 47 and/or 50 of the variable light chain, in particular of a Vkappa1 variable light chain. Preferably, the antibody is modified to comprise arginine (R) at AHo position 47 and/or at AHo position 50 of the variable light chain. In some embodiments, lysine (K) is substituted by arginine (R) at AHo position 47 and/or AHo position 50 of the variable light chain. As the antibodies of the invention can comprise additional modifications as desired, the methods of the invention can comprise the further step of modifying the antibody such as to comprise Serine (S) at heavy chain position 12 (AHo numbering); Serine (S) or Threonine (T) at heavy chain position 103 (AHo numbering) and/or Serine (S) or Threonine (T) at heavy chain position 144 (AHo numbering). Additionally, the antibody can be modified to comprise Serine (S) or Threonine (T) at heavy chain positions 97, 98 and/or 99 (AHo numbering). Preferably, the method comprises the step of modifying the antibody to comprise Serine (S) at heavy chain position 12 (AHo numbering), Threonine (T) at heavy chain position 103 (AHo numbering) and Threonine (T) at heavy chain position 144 (AHo numbering).

The invention further provides a method of generating a humanized antibody with a low propensity for aggregating in solution, the method comprising selecting a variable light chain framework that comprises arginine (R) at AHo position 47 and/or at AHo position 50. The method may further comprise selecting a variable heavy chain framework that comprises a serine (S) at heavy chain position 12 (AHo numbering); serine (S) or threonine (T) at heavy chain position 103 (AHo numbering) and/or serine (S) or threonine (T) at heavy chain position 144 (AHo numbering). In one embodiment, a framework identified based on a chosen selection criteria may be further modified with an aggregation-reducing modification of the invention. For example, if a variable light chain framework is identified that has an arginine (R) at position 50, the residue at AHo position may be substituted with a different amino acid, such as arginine (R), or if a variable heavy chain is identified that has a serine (S) at AHo position 12, the residues at AHo positions 103 and 144 may be substituted with threonines.

As used herein, a "humanized" antibody is an antibody that comprises non-human CDRs and human or human-derived variable heavy and/or human or human-derived variable light chain framework sequences. Humanization of antibodies is well known in the art. In one embodiment, the humanized antibody comprises at least one, and preferably six, CDRs from an antibody produced in a rabbit or selected from a CDR library.

The variable antibody frameworks can be selected, for example, from a database (such as the Kabat database, Genbank, VBASE, VBASE2, The Kabat Database of Sequences of Proteins of Immunological Interest, the Universal Protein Resource, and Abysis Database, based on identity and/or similarity with the variable framework sequences of the antibody from which the CDRs originated, or based on otherwise preferred framework sequence(s).

Various computer programs are available for searching suitable human framework sequences that meet the selected requirement(s). For example, "KabatMan" is a computer-searchable version of the Kabat antibody sequence data from the *Sequences of Immunological Interest* book. The KabatMan program is described in the paper: Martin (1996) Accessing the Kabat Antibody Sequence Database by Computer *PROTEINS: Structure, Function and Genetics,* 25, 130-133. The Abysis database integrates sequence data from Kabat, IMGT and the PDB with structural data from the PDB. It provides a comprehensive point-and-click interface which allows one to search the sequence data on various criteria and display results in different formats. For data from the PDB, sequence searches can be combined with structural constraints.

In another aspect, the invention provides an antibody generated by the method disclosed herein. In a preferred embodiment, said antibody comprises a VL antibody framework having at least 80% identity, more preferably 85%, 90%, 95%, 96%, 97%, 98%, more preferably 99% to SEQ ID NO: 12 or SEQ ID NO: 13; preferably, the antibody comprises arginine (R) at AHo position 47 and/or at AHo position 50 of the variable light chain.

Additionally or alternatively, the VH antibody framework is or comprises SEQ ID NO: 3 or a sequence having at least 80% identity, more preferably, 85%, 90%, 95%, 96%, 97%, 98%, more preferably 99% to SEQ ID NO: 3.

In certain embodiments, the invention further provides:

(1) A method for reducing the aggregation propensity of an antibody being a heterodimeric complex that comprises heavy and light variable domains, the method comprising the steps of:

(a) providing a full atomistic molecular presentation of the antibody;

(b) determining the free energy of the interface between both domains;

(c) choosing one or more amino acid residues participating in the interface for substitution by providing a molecular model of the antibody comprising the one or more substitutions at the selected positions and determining the free energy of the interface of the substituted molecular presentation;

(d) selecting an amino acid residue for substitution if the free energy of the interface of the substituted molecular model is lower than the free energy of the interface of the initial molecular model;

(2) A method of (1), wherein the free energy of the interface is determined by calculating the energy difference between the complex and the sum of the energies of the individual domains in the context of an implicit solvent method;

(3) The method of (2), wherein the solvent is GBMV or PBSA;

(4) The method of anyone of the preceding (1)-(3), further comprising the step of
(i) simulating the charge distribution of the protein, wherein said step is performed within step a and b;
(5) The method of (4), wherein the charge distribution is simulated based on electrostatic or van der Waals forces;
(6) The method of anyone of the preceding (1)-(5), wherein step (c) comprises the additional step of energy minimization in the area around the mutation;
(7) The method of anyone of the preceding (1)-(7), wherein the antibody is a single chain variable fragment (scFv).

Antibodies of the invention may be generated using routine techniques in the field of recombinant genetics. Knowing the sequences of the polypeptides, the cDNAs encoding them can be generated by gene synthesis by methods well known in the art. These cDNAs can be cloned into suitable vector plasmids.

Standard cloning and mutagenesis techniques well known to the person skilled in the art can be used to attach linkers, shuffle domains or construct fusions for the production of Fab fragments. Basic protocols disclosing the general methods of this invention are described in *Molecular Cloning, A Laboratory Manual* (Sambrook & Russell, 3$^{rd}$ ed. 2001) and in *Current Protocols in Molecular Biology* (Ausubel et al., 1999).

The DNA sequence harboring a gene encoding a scFv polypeptide, or in the case of Fab fragments, encoding either two separate genes or a bi-cistronic operon comprising the two genes for the VL-Cκ and the VH-CH1 fusions are cloned in a suitable expression vector, preferably one with an inducible promoter. Care must be taken that in front of each gene an appropriate ribosome binding site is present that ensures translation. It is to be understood that the antibodies of the present invention comprise the disclosed sequences rather than they consist of them. For example, cloning strategies may require that a construct is made from which an antibody with one or a few additional residues at the N-terminal end are present. Specifically, the methionine derived from the start codon may be present in the final protein in cases where it has not been cleaved posttranslationally. Most of the constructs for scFv antibodies give rise to an additional alanine at the N-terminal end. In a preferred embodiment of the present invention, an expression vector for periplasmic expression in *E. coli* is chosen (Krebber, 1997). Said vector comprises a promoter in front of a cleavable signal sequence. The coding sequence for the antibody peptide is then fused in frame to the cleavable signal sequence. This allows the targeting of the expressed polypeptide to the bacterial periplasm where the signal sequence is cleaved. The antibody is then folded. In the case of the Fab fragments, both the VL-Cκ and the VH-CH1 fusions peptides must be linked to an export signal. The covalent S—S bond is formed at the C-terminal cysteines after the peptides have reached the periplasm. If cytoplasmic expression of antibodies is preferred, said antibodies usually can be obtained at high yields from inclusion bodies, which can be easily separated from other cellular fragments and protein. In this case the inclusion bodies are solubilized in a denaturing agent such as e.g. guaridine hydrochloride (Gnd-HCl) and then refolded by renaturation procedures well known to those skilled in the art.

Plasmids expressing the scFv or Fab polypeptides are introduced into a suitable host, preferably a bacterial, yeast or mammalian cell, most preferably a suitable *E. coli* strain as for example JM83 for periplasmic expression or BL21 for expression in inclusion bodies. The polypeptide can be harvested either from the periplasm or form inclusion bodies and purified using standard techniques such as ion exchange chromatography, reversed phase chromatography, affinity chromatography and/or gel filtration known to the person skilled in the art.

Antibodies of the invention can be characterized with respect to yield, solubility and stability in vitro. For example, binding capacities towards TNF, preferably towards human TNFα, can be tested in vitro by ELISA or surface plasmon resonance (BIACore), using recombinant human TNF as described in WO9729131, the latter method also allowing to determine the $k_{off}$ rate constant, which should preferably be less than $10^{-3}$ s$^{-1}$. $K_d$ values of ≤10 nM are preferred.

In one embodiment, the present invention provides antibodies that bind TNFα and thus are suitable to block the function of TNFα in vivo. In a particular embodiment, the anti-TNFα antibody comprises the sequence of SEQ ID NO: 10 or SEQ ID NO: 17.

For therapeutic applications, anti-TNF antibodies of the invention are administered to a mammal, preferably a human, in a pharmaceutically acceptable dosage form such as those discussed above, including those that may be administered to a human intravenously as a bolus or by continuous infusion over a period of time, by intramuscular, intraperitoneal, intra-cerebrospinal, subcutaneous, intra-articular, intrasynovial, intrathecal, oral, topical, intraocular, intranasal, otic, sublingual, transdermal, or inhalation routes, for example. The antibodies also are suitably administered by intra tumoral, peritumoral, intralesional, or perilesional routes, to exert local as well as systemic therapeutic effects.

For the prevention or treatment of disease, the appropriate dosage of antibody will depend on the type of disease to be treated, as defined above, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

Anti-TNF antibodies of the invention are useful in the treatment of TNF-mediated diseases. Depending on the type and severity of the disease, about 1 μg/kg to about 50 mg/kg (e.g., 0.1-20 mg/kg) of antibody is an initial candidate dosage for administration to the patient, whether, for example, by one or more separate administrations, or by continuous infusion. A typical daily or weekly dosage might range from about 1 μg/kg to about 20 mg/kg or more, depending on the factors mentioned above. For repeated administrations over several days or longer, depending on the condition, the treatment is repeated until a desired suppression of disease symptoms occurs. However, other dosage regimens may be useful. The progress of this therapy is easily monitored by conventional techniques and assays, including, for example, radiographic tumor imaging.

According to another embodiment of the invention, the effectiveness of the antibody in preventing or treating disease may be improved by administering the antibody serially or in combination with another agent that is effective for those purposes, such as vascular endothelial growth factor (VEGF), an antibody capable of inhibiting or neutralizing the angiogenic activity of acidic or basic fibroblast growth factor (FGF) or hepatocyte growth factor (HGF), an antibody capable of inhibiting or neutralizing the coagulant activities of tissue factor, protein C, or protein S (see Esmon et al., PCT Patent Publication No. WO 91/01753, published 21 Feb. 1991), an antibody capable of binding to HER2 receptor (see Hudziak et al., PCT Patent Publication No. WO 89/06692, published 27 Jul. 1989), or one or more conventional therapeutic agents such as, for example, alkylating agents, folic acid antagonists, anti-metabolites of nucleic acid metabolism, antibiotics, pyrimidine analogs, 5-fluorouracil, cisplatin, purine nucleosides, amines, amino acids, triazol nucleosides, or corticosteroids. Such other agents may be present in the composition being administered or may be administered separately. Also, the antibody is suitably administered serially or in combination with radiological treatments, whether involving irradiation or administration of radioactive substances.

Antibodies of the invention may be used as affinity purification agents. In this process, the antibodies are immobilized on a solid phase such a Sephadex resin or filter paper, using methods well known in the art. The immobilized antibody is contacted with a sample containing a target protein (or fragment thereof) that the antibody binds, such as TNF in the case of anti-TNFα antibodies, to be purified, and thereafter the support is washed with a suitable solvent that will remove substantially all the material in the sample except the target protein, which is bound to the immobilized antibody. Finally, the support is washed with another suitable solvent, such as glycine buffer, pH 5.0, that will release the target protein from the antibody.

Antibodies may also be useful in diagnostic assays for a target protein, e.g., detecting its expression in specific cells, tissues, or serum. Such diagnostic methods may be useful in cancer diagnosis.

For diagnostic applications, the antibody typically will be labeled with a detectable moiety. Numerous labels are available which can be generally grouped into the following categories:

(a) Radioisotopes, such as $^{111}$In, $^{99}$Tc, $^{14}$C, $^{131}$I, $^{125}$I, $^{3}$H, $^{32}$P or $^{35}$S. The antibody can be labeled with the radioisotope using the techniques described in Current Protocols in Immunology, Volumes 1 and 2, Coligen et al., Ed. Wiley-Interscience, New York, N.Y., Pubs. (1991) for example and radioactivity can be measured using scintillation counting.

(b) Fluorescent labels such as rare earth chelates (europium chelates) or fluorescein and its derivatives, rhodamine and its derivatives, dansyl, Lissamine, phycoerythrin and Texas Red are available. The fluorescent labels can be conjugated to the antibody using the techniques disclosed in Current Protocols in Immunology, supra, for example. Fluorescence can be quantified using a fluorimeter.

(c) Various enzyme-substrate labels are available and U.S. Pat. No. 4,275,149 provides a review of some of these. The enzyme generally catalyzes a chemical alteration of the chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, .beta.-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for use in Enzyme Immunoassay, in Methods in Enzym. (ed J. Langone & H. Van Vunakis), Academic press, New York, 73:147-166 (1981).

Examples of enzyme-substrate combinations include, for example (i) Horseradish peroxidase (HRPO) with hydrogen peroxidase as a substrate, wherein the hydrogen peroxidase oxidizes a dye precursor (e.g., orthophenylene diamine (OPD) or 3,3',5,5'-tetramethyl benzidine hydrochloride (TMB));

(ii) alkaline phosphatase (AP) with para-Nitrophenyl phosphate as chromogenic substrate; and (iii) β-D-galactosidase (β-D-Gal) with a chromogenic substrate (e.g., P-nitrophenyl-β-D-galactosidase) or fluorogenic substrate 4-methylumbelliferyl-.beta.-D-galactosidase.

Numerous other enzyme-substrate combinations are available to those skilled in the art. For a general review of these, see U.S. Pat. Nos. 4,275,149 and 4,318,980. Sometimes, the label is indirectly conjugated with the antibody. The skilled artisan will be aware of various techniques for achieving this. For example, the antibody can be conjugated with biotin and any of the three broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody is conjugated with a small hapten (e.g., digoxin) and one of the different types of labels mentioned above is conjugated with an anti-hapten antibody (e.g., anti-digoxin antibody). Thus, indirect conjugation of the label with the antibody can be achieved.

In certain embodiments, an antibody need not be labeled, and the presence thereof can be detected using a labeled antibody which binds to a target antibody.

The antibodies of the present invention may be employed in any known assay method, such as competitive binding assays, direct and indirect sandwich assays, and immunoprecipitation assays. Zola, Monoclonal Antibodies: A Manual of Techniques, pp. 147-158(CRC Press, Inc. 1987).

Competitive binding assays rely on the ability of a labeled standard to compete with the test sample analyte for binding with a limited amount of antibody. For example, the amount of TNF protein in the test sample is inversely proportional to the amount of standard that becomes bound to the antibodies. To facilitate determining the amount of standard that becomes bound, the antibodies generally are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three-part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

For immunohistochemistry, the tissue sample, such as a tumor sample, may be fresh or frozen or may be embedded in paraffin and fixed with a preservative such as formalin, for example.

The antibodies may also be used for in vivo tumor diagnostic assays. Generally, the antibody is labeled with a radio nuclide (such as $^{111}$In, $^{99}$Tc, $^{14}$C, $^{131}$I, $^{125}$I, $^{3}$H, $^{32}$P or $^{35}$S) so that the tumor can be localized using immunoscintiography.

An antibody of the present invention can be provided in a kit, a packaged combination of reagents in predetermined amounts with instructions for performing the diagnostic assay. Where the antibody is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

The invention further provides pharmaceutical formulations comprising one or more antibodies of the invention for therapeutic purposes. In one embodiment, the invention provides anti-TNF antibodies for the treatment of TNF-mediated diseases.

The term "pharmaceutical formulation" refers to preparations which are in such form as to permit the biological activity of the antibody to be unequivocally effective, and which contain no additional components which are toxic to the subjects to which the formulation would be administered. "Pharmaceutically acceptable" excipients (vehicles, additives) are those which can reasonably be administered to a subject mammal to provide an effective dose of the active ingredient employed.

A "stable" formulation is one in which the antibody therein essentially retains its physical stability and/or chemical stability and/or biological activity upon storage. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993), for example. Stability can be measured at a selected temperature for a selected time period. Preferably, the formulation is stable at room temperature (about 30° C.) or at 40° C. for at least 1 month and/or stable at about 2-8° C. for at least 1 year for at least 2 years. Furthermore, the formulation is preferably stable following freezing (to, e.g., −70° C.) and thawing of the formulation.

An antibody "retains its physical stability" in a pharmaceutical formulation if it shows no signs of aggregation, precipitation and/or denaturation upon visual examination of color and/or clarity, or as measured by UV light scattering or by size exclusion chromatography.

An antibody "retains its chemical stability" in a pharmaceutical formulation, if the chemical stability at a given time is such that the protein is considered to still retain its biological activity as defined below. Chemical stability can be assessed by detecting and quantifying chemically altered forms of the protein. Chemical alteration may involve size modification (e.g. clipping) which can be evaluated using size exclusion chromatography, SDS-PAGE and/or matrix-assisted laser desorption ionization/time-of-flight mass spectrometry (MALDI/TOF MS), for example. Other types of chemical alteration include charge alteration (e.g. occurring as a result of deamidation) which can be evaluated by ion-exchange chromatography, for example.

An antibody "retains its biological activity" in a pharmaceutical formulation, if the biological activity of the antibody at a given time is within about 10% (within the errors of the assay) of the biological activity exhibited at the time the pharmaceutical formulation was prepared as determined in an antigen binding assay, for example. Other "biological activity" assays for antibodies are elaborated herein below.

By "isotonic" is meant that the formulation of interest has essentially the same osmotic pressure as human blood. Isotonic formulations will generally have an osmotic pressure from about 250 to 350 mOsm. Isotonicity can be measured using a vapor pressure or ice-freezing type osmometer, for example.

A "polyol" is a substance with multiple hydroxyl groups, and includes sugars (reducing and non-reducing sugars), sugar alcohols and sugar acids. Preferred polyols herein have a molecular weight which is less than about 600 kD (e.g. in the range from about 120 to about 400 kD). A "reducing sugar" is one which contains a hemiacetal group that can reduce metal ions or react covalently with lysine and other amino groups in proteins and a "non-reducing sugar" is one which does not have these properties of a reducing sugar. Examples of reducing sugars are fructose, mannose, maltose, lactose, arabinose, xylose, ribose, rhamnose, galactose and glucose. Non-reducing sugars include sucrose, trehalose, sorbose, melezitose and raffinose. Mannitol, xylitol, erythritol, threitol, sorbitol and glycerol are examples of sugar alcohols. As to sugar acids, these include L-gluconate and metallic salts thereof. Where it is desired that the formulation is freeze-thaw stable, the polyol is preferably one which does not crystallize at freezing temperatures (e.g. −20° C.) such that it destabilizes the antibody in the formulation. Non-reducing sugars include, but are not limited to, sucrose and trehalose.

As used herein, "buffer" refers to a buffered solution that resists changes in pH by the action of its acid-base conjugate components. The buffer of this invention has a pH in the range from about 4.5 to about 7.0; preferably from about 4.8 to about 6.5. Examples of buffers that will control the pH in this range include acetate (e.g. sodium acetate), succinate (such as sodium succinate), gluconate, histidine, citrate and other organic acid buffers. Where a freeze-thaw stable formulation is desired, the buffer is preferably not phosphate.

In a pharmacological sense, in the context of the present invention, a "therapeutically effective amount" of an antibody refers to an amount effective in the prevention or treatment of a disorder for the treatment of which the antibody is effective. A "disease/disorder" is any condition that would benefit from treatment with the antibody. This includes chronic and acute disorders or diseases including those pathological conditions which predispose the mammal to the disorder in question.

A "preservative" is a compound which can be included in the formulation to essentially reduce bacterial action therein, thus facilitating the production of a multi-use formulation, for example. Examples of potential preservatives include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols such as phenol, butyl and benzyl alcohol, alkyl parabens such as methyl or propyl paraben, catechol, resorcinol, cyclohexanol, 3-pentanol, and m-cresol. The most preferred preservative herein is benzyl alcohol.

The present invention also provides pharmaceutical compositions comprising one or more antibodies, together with at least one physiologically acceptable carrier or excipient. Pharmaceutical compositions may comprise, for example, one or more of water, buffers (e.g., neutral buffered saline or phosphate buffered saline), ethanol, mineral oil, vegetable oil, dimethylsulfoxide, carbohydrates (e.g., glucose, mannose, sucrose or dextrans), mannitol, proteins, adjuvants, polypeptides or amino acids such as glycine, antioxidants, chelating agents such as EDTA or glutathione and/or preservatives. As noted above, other active ingredients may (but need not) be included in the pharmaceutical compositions provided herein.

A carrier is a substance that may be associated with an antibody prior to administration to a patient, often for the purpose of controlling stability or bioavailability of the compound. Carriers for use within such formulations are generally biocompatible, and may also be biodegradable. Carriers include, for example, monovalent or multivalent molecules such as serum albumin (e.g., human or bovine), egg albumin, peptides, polylysine and polysaccharides such as aminodextran and polyamidoamines. Carriers also include solid support materials such as beads and microparticles comprising, for example, polylactate polyglycolate, poly(lactide-co-glycolide), polyacrylate, latex, starch, cellulose or dextran. A carrier may bear the compounds in a variety of ways, including covalent bonding (either directly or via a linker group), noncovalent interaction or admixture.

Pharmaceutical compositions may be formulated for any appropriate manner of administration, including, for example, ocular, intranasal, otic, sublingual, transdermal, topical, oral, nasal, rectal or parenteral administration. In certain embodiments, compositions in a form suitable for oral use are preferred. Such forms include, for example, pills, tablets, troches, lozenges, aqueous or oily suspensions, dispersible powders or granules, emulsion, hard or soft capsules, or syrups or elixirs. Within yet other embodiments, compositions provided herein may be formulated as a lyophilizate. The term parenteral as used herein includes subcutaneous, intradermal, intravascular (e.g., intravenous), intramuscular, spinal, intracranial, intrathecal and intraperitoneal injection, as well as any similar injection or infusion technique.

In certain embodiments, an antibody of the invention can be delivered directly to the eye by ocular tissue injection such as periocular, conjunctival, subtenon, intracameral, intravitreal, intraocular, subretinal, subconjunctival, retrobulbar, or intracanalicular injections; by direct application to the eye using a catheter or other placement device such as a retinal pellet, intraocular insert, suppository or an implant comprising a porous, non-porous, or gelatinous material; by topical ocular drops or ointments; or by a slow release device in the cul-de-sac or implanted adjacent to the sclera (transscleral) or in the sclera (intrascleral) or within the eye. Intracameral injection may be through the cornea into the anterior chamber to allow the agent to reach the trabecular meshwork. Intracanalicular injection may be into the venous collector channels draining Schlemm's canal or into Schlemm's canal.

For ophthalmic delivery, an antibody of the invention may be combined with ophthalmologically acceptable preservatives, co-solvents, surfactants, viscosity enhancers, penetration enhancers, buffers, sodium chloride, or water to form an aqueous, sterile ophthalmic suspension or solution. Topical ophthalmic products may be packaged, for example, in multidose form. Preservatives may thus be required to prevent microbial contamination during use. Suitable preservatives include: chlorobutanol, methyl paraben, propyl paraben, phenylethyl alcohol, edetate disodium, sorbic acid, polyquaternium-1, or other agents known to those skilled in the art. Such preservatives are typically employed at a level of from 0.001 to 1.0% w/v. Unit dose compositions of the present invention will be sterile, but typically unpreserved. Such compositions, therefore, generally will not contain preservatives.

In certain embodiments, compositions intended to be administered topically to the eye are formulated as eye drops or eye ointments, wherein the total amount of antibody will be about 0.001 to 1.0% (w/w). Preferably, the amount of TNFα antibody is about 0.01 to about 1.0% (w/w).

Compositions of the invention in certain circumstances will be administered as solutions for topical administration. Aqueous solutions are generally preferred, based on ease of formulation, as well as a patient's ability to easily administer such compositions by means of instilling one to two drops of the solutions in the affected eyes. However, the compositions may also be suspensions, viscous or semi-viscous gels, or other types of solid or semi-solid compositions.

Compositions intended for oral use may be prepared according to any method known to the art for the manufacture of pharmaceutical compositions and may contain one or more agents, such as sweetening agents, flavoring agents, coloring agent, and preserving agents in order to provide appealing and palatable preparations. Tablets contain the active ingredient in admixture with physiologically acceptable excipients that are suitable for the manufacture of tablets. Such excipients include, for example, inert diluents (e.g., calcium carbonate, sodium carbonate, lactose, calcium phosphate or sodium phosphate), granulating and disintegrating agents (e.g., corn starch or alginic acid), binding agents (e.g., starch, gelatin or acacia) and lubricating agents (e.g., magnesium stearate, stearic acid or talc). The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent (e.g., calcium carbonate, calcium phosphate or kaolin), or as soft gelatin capsules wherein the active ingredient is mixed with water or an oil medium (e.g., peanut oil, liquid paraffin or olive oil). Aqueous suspensions contain the antibody in admixture with excipients suitable for the manufacture of aqueous suspensions. Such excipients include suspending agents (e.g., sodium carboxymethylcellulose, methylcellulose, hydropropylmethylcellulose, sodium alginate, polyvinylpyrrolidone, gum tragacanth and gum acacia); and dispersing or wetting agents (e.g., naturally-occurring phosphatides such as lecithin, condensation products of an alkylene oxide with fatty acids such as polyoxyethylene stearate, condensation products of ethylene oxide with long chain aliphatic alcohols such as heptadeca-ethyleneoxycetanol, condensation products of ethylene oxide with partial esters derived from fatty acids and a hexitol such as polyoxyethylene sorbitol monooleate, or condensation products of ethylene oxide with partial esters derived from fatty acids and hexitol anhydrides such as polyethylene sorbitan monooleate). Aqueous suspensions may also comprise one or more preservatives, for example ethyl or n-propyl p-hydroxybenzoate, one or more coloring agents, one or more flavoring agents, and one or more sweetening agents, such as sucrose or saccharin. Syrups and elixirs may be formulated with sweetening agents, such as glycerol, propylene glycol, sorbitol, or sucrose. Such formulations may also comprise one or more demulcents, preservatives, flavoring agents, and/or coloring agents.

Oily suspensions may be formulated by suspending the active ingredients in a vegetable oil (e.g., arachis oil, olive oil, sesame oil, or coconut oil) or in a mineral oil such as liquid paraffin. The oily suspensions may contain a thickening agent such as beeswax, hard paraffin, or cetyl alcohol. Sweetening agents, such as those set forth above, and/or flavoring agents may be added to provide palatable oral preparations. Such suspensions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions may also be in the form of oil-in-water emulsions. The oily phase may be a vegetable oil (e.g., olive oil or arachis oil), a mineral oil (e.g., liquid paraffin), or a mixture thereof. Suitable emulsifying agents include naturally-occurring gums (e.g., gum acacia or gum tragacanth), naturally-occurring phosphatides (e.g., soy bean, lecithin, and esters or partial esters derived from fatty acids and hexitol), anhydrides (e.g., sorbitan monoleate), and condensation products of partial esters derived from fatty acids and hexitol with ethylene oxide (e.g., polyoxyethylene sorbitan monooleate). An emulsion may also comprise one or more sweetening and/or flavoring agents.

The pharmaceutical composition may be prepared as a sterile injectable aqueous or oleaginous suspension in which the modulator, depending on the vehicle and concentration used, is either suspended or dissolved in the vehicle. Such a composition may be formulated according to the known art using suitable dispersing, wetting agents and/or suspending agents such as those mentioned above. Among the acceptable vehicles and solvents that may be employed are water, 1,3-butanediol, Ringer's solution and isotonic sodium chloride solution. In addition, sterile, fixed oils may be employed as a solvent or suspending medium. For this purpose any bland fixed oil may be employed, including synthetic mono- or diglycerides. In addition, fatty acids such as oleic acid may be used in the preparation of injectable compositions, and adjuvants such as local anesthetics, preservatives and/or buffering agents can be dissolved in the vehicle.

Pharmaceutical compositions may be formulated as sustained release formulations (i.e., a formulation such as a capsule that affects a slow release of modulator following administration). Such formulations may generally be prepared using well known technology and administered by, for example, oral, rectal, or subcutaneous implantation, or by implantation at the desired target site. Carriers for use within such formulations are biocompatible, and may also be biodegradable; preferably the formulation provides a relatively constant level of modulator release. The amount of an antibody contained within a sustained release formulation depends upon, for example, the site of implantation, the rate and expected duration of release and the nature of the disease/disorder to be treated or prevented.

Anti-TNFα antibodies provided herein can be administered in an amount that achieves a concentration in a body fluid (e.g., blood, plasma, serum, CSF, synovial fluid, lymph, cellular interstitial fluid, tears or urine) that is sufficient to detectably bind to TNF and prevent or inhibit TNF-mediated diseases/disorders. A dose is considered to be effective if it results in a discernible patient benefit as described herein. Preferred systemic doses range from about 0.1 mg to about 140 mg per kilogram of body weight per day (about 0.5 mg to about 7 g per patient per day), with oral doses generally being about 5-20 fold higher than intravenous doses. The amount of antibody that may be combined with the carrier materials to produce a single dosage form will vary depending upon the host treated and the particular mode of administration. Dosage unit forms will generally contain between from about 1 mg to about 500 mg of an active ingredient.

In certain embodiments, pharmaceutical compositions may be packaged for treating conditions responsive to an antibody directed to TNF. Packaged pharmaceutical compositions may include a container holding an effective amount of at least one antibody as described herein and instructions (e.g., labeling) indicating that the contained composition is to be used for treating a disease/disorder responsive to one antibody following administration in the patient.

The antibodies of the present invention can also be chemically modified. Preferred modifying groups are polymers, for example an optionally substituted straight or branched chain polyalkene, polyalkenylene, or polyoxyalkylene polymer or a branched or unbranched polysaccharide. Such effector group may increase the half-life of the antibody in vivo. Particular examples of synthetic polymers include optionally substituted straight or branched chain poly(ethyleneglycol) (PEG), poly(propyleneglycol), poly(vinylalcohol) or derivatives thereof. Particular naturally occurring polymers include lactose, amylose, dextran, glycogen or derivatives thereof. The size of the polymer may be varied as desired, but will generally be in an average molecular weight range from 500 Da to 50000 Da. For local application where the antibody is designed to penetrate tissue, a preferred molecular weight of the polymer is around 5000 Da. The polymer molecule can be attached to the antibody, for example to the C-terminal end of a Fab fragment heavy chain via a covalently linked hinge peptide as described in WO0194585. Regarding the attachment of PEG moieties, reference is made to "Poly(ethyleneglycol) Chemistry, Biotechnological and Biomedical Applications", 1992, J. Milton Harris (ed), Plenum Press, New York and "Bioconjugation Protein Coupling Techniques for the Biomedical Sciences", 1998, M. Aslam and A. Dent, Grove Publishers, New York.

After preparation of the antibody of interest as described above, the pharmaceutical formulation comprising it is prepared. The antibody to be formulated has not been subjected to prior lyophilization and the formulation of interest herein is an aqueous formulation. Preferably the antibody in the formulation is an antibody fragment, such as an scFv. The therapeutically effective amount of antibody present in the formulation is determined by taking into account the desired dose volumes and mode(s) of administration, for example. From about 0.1 mg/ml to about 50 mg/ml, preferably from about 0.5 mg/ml to about 25 mg/ml and most preferably from about 2 mg/ml to about 10 mg/ml is an exemplary antibody concentration in the formulation.

An aqueous formulation is prepared comprising the antibody in a pH-buffered solution as described above. The buffer concentration can be from about 1 mM to about 50 mM, preferably from about 5 mM to about 30 mM, depending, for example, on the buffer and the desired isotonicity of the formulation.

A polyol, which acts as a tonicifier and may stabilize the antibody, is included in the formulation. In preferred embodiments, the formulation does not contain a tonicifying amount of a salt such as sodium chloride, as this may cause the antibody to precipitate and/or may result in oxidation at low pH. In preferred embodiments, the polyol is a non-reducing sugar, such as sucrose or trehalose. The polyol is added to the formulation in an amount which may vary with respect to the desired isotonicity of the formulation. Preferably the aqueous formulation is isotonic, in which case suitable concentrations of the polyol in the formulation are in the range from about 1% to about 15% w/v, preferably in the range from about 2% to about 10% why, for example. However, hypertonic or hypotonic formulations may also be suitable. The amount of polyol added may also alter with respect to the molecular weight of the polyol. For example, a lower amount of a monosaccharide (e.g. mannitol) may be added, compared to a disaccharide (such as trehalose).

A surfactant may also be added to the antibody formulation. Exemplary surfactants include nonionic surfactants such as polysorbates (e.g. polysorbates 20, 80 etc) or poloxamers (e.g. poloxamer 188). Typically, the amount of surfactant added is such that it reduces aggregation of the formulated antibody/antibody derivative and/or minimizes the formation of particulates in the formulation and/or reduces adsorption. For example, the surfactant may be present in the formulation in an amount from about 0.001% to about 0.5%, preferably from about 0.005% to about 0.2% and most preferably from about 0.01% to about 0.1%.

In one embodiment, a formulation contains the above-identified agents (i.e. antibody, buffer, polyol and surfactant) and is essentially free of one or more preservatives, such as benzyl alcohol, phenol, m-cresol, chlorobutanol and benzethonium Cl. In another embodiment, a preservative may be included in the formulation, particularly where the formulation is a multidose formulation. The concentration of preservative may be in the range from about 0.1% to about 2%, most preferably from about 0.5% to about 1%. One or more other pharmaceutically acceptable carriers, excipients or stabilizers such as those described in Remington's Pharmaceutical Sciences 21st edition, Osol, A. Ed. (2006) may be included in the formulation provided that they do not adversely affect the desired characteristics of the formulation. Acceptable carriers, excipients or stabilizers are nontoxic to recipients at the dosages and concentrations employed and include; additional buffering agents; co-solvents; antioxidants including ascorbic acid and methionine; chelating agents such as EDTA; metal complexes (e.g. Zn-protein complexes); biodegradable polymers such as polyesters; and/or salt-forming counterions such as sodium.

The formulations to be used for in vivo administration must be sterile. This is readily accomplished by filtration through sterile filtration membranes, prior to, or following, preparation of the formulation.

The formulation is administered to a mammal in need of treatment with the antibody, preferably a human, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes, or other routes as described herein. In certain embodiments, the formulation is administered to the mammal by intravenous administration. For such purposes, the formulation may be injected using a syringe or via an IV line, for example.

The appropriate dosage ("therapeutically effective amount") of the antibody will depend, for example, on the condition to be treated, the severity and course of the condition, whether the antibody is administered for preventive or therapeutic purposes, previous therapy, the patient's clinical history and response to the antibody, the type of antibody used, and the discretion of the attending physician. The antibody is suitably administered to the patient at one time or over a series of treatments and may be administered to the patient at any time from diagnosis onwards. The antibody may be administered as the sole treatment or in conjunction with other drugs or therapies useful in treating the condition in question.

As a general proposition, the therapeutically effective amount of the antibody administered will be in the range of about 0.1 to about 100 mg/kg of patient body weight whether by one or more administrations, with the typical range of antibody used being about 0.3 to about 20 mg/kg, more preferably about 0.3 to about 15 mg/kg, administered daily, for example. However, other dosage regimens may be useful. The progress of this therapy is easily monitored by conventional techniques.

In certain embodiments, pharmaceutical compositions comprising an anti-TNFα antibody of the invention are administered to a patient suffering from a TNF-mediated disorder.

In another embodiment of the invention, an article of manufacture is provided comprising a container which holds the aqueous pharmaceutical formulation of the present invention and optionally provides instructions for its use. Suitable containers include, for example, bottles, vials and syringes. The container may be formed from a variety of materials such as glass or plastic. An exemplary container is a 3-20 cc single use glass vial. Alternatively, for a multidose formulation, the container may be 3-100 cc glass vial. The container holds the formulation and the label on, or associated with, the container may indicate directions for use. The article of manufacture may further include other materials desirable from a commercial and user standpoint, including other buffers, diluents, filters, needles, syringes, and package inserts with instructions for use.

The contents of any patents, patent applications, and references cited throughout this specification are hereby incorporated by reference in their entireties.

Unless otherwise required by context, singular terms used herein shall include pluralities and plural terms shall include the singular.

EXAMPLES

The present disclosure is further illustrated by the following examples, which should not be construed as further limiting. The contents of all figures and all references, patents and published patent applications cited throughout this application are expressly incorporated herein by reference in their entireties.

Throughout the examples, the following materials and methods were used unless otherwise stated.

General Materials and Methods

In general, the practice of the present invention employs, unless otherwise indicated, conventional techniques of chemistry, molecular biology, recombinant DNA technology, immunology (especially, e.g., antibody technology), and standard techniques of polypeptide preparation. See, e.g., Sambrook, Fritsch and Maniatis, Molecular Cloning: Cold Spring Harbor Laboratory Press (1989); Antibody Engineering Protocols (Methods in Molecular Biology), 510, Paul, S., Humana Pr (1996); Antibody Engineering: A Practical Approach (Practical Approach Series, 169), McCafferty, Ed., Irl Pr (1996); Antibodies: A Laboratory Manual, Harlow et al., C.S.H.L. Press, Pub. (1999); and Current Protocols in Molecular Biology, eds. Ausubel et al., John Wiley & Sons (1992).

Thermostability Measurements

Attenuated total reflectance Fourier transform IR (FTIR-ATR) spectra were obtained for various single chains and follow up molecules using the FT-IR Bio-ATR cell in a Tensor Bruker. The molecules were concentrated up to 3 mg/ml and dialyzed overnight at 4° C. against PBS, pH 6.5 and the buffer flow through was collected as blank. The denaturation profiles were obtained by thermo challenging the molecules with a broad range of temperatures in 5° C. steps (25 to 95° C.). All spectra manipulations were performed using OPUS software. The main buffer and transient atmospheric ($CO_2$ and $H_2O$) background were substracted from the protein spectrum. The resulting protein spectrum was then baseline corrected and the protein amide I spectra was determined from the width of the widest resolvable peak in the expected region. Second derivative spectra were obtained for the amide I band spectra using a third degree polynomial function with a smoothing function. Changes in protein structure were estimated by amide I second derivative analysis using a linear calibration curve for the initial curve-fit calculations assuming 0% denaturation for the 3 lower measurements and 100% denaturation for the 3 higher measurements. The denaturation profiles were used to approximate midpoints of the thermal unfolding transitions (TM) for every variant applying the Boltzmann sigmoidal model.

Solubility Measurements

Relative solubility of various scFv molecules was measured after enhancing protein aggregation and precipitation in presence of ammonium sulfate. Ammonium sulfate was added to the protein in aqueous solutions to yield increments of 5% of saturation in the final mixture salt-protein. The precipitation in the dynamic range was determined empirically and the saturation intervals reduced in this range to 2.5% intervals saturation in the final mixture. After ammonium sulfate addition, samples were gently mixed and centrifuged 30 minutes at 6000 rpm. The remaining protein in supernatants was recovered for each ammonium sulfate percentage of saturation. Solubility curves were determined by measuring the protein concentration in the supernatant using NanoDrop 1000 Spectrophotometer. Measurements of remaining soluble protein in supernatants were normalized and used to estimate midpoints of relative solubility for every variant applying the Boltzmann sigmoidal model.

Short Term Stability Test

Protein was examined after two weeks incubation at 40° C. for soluble aggregates and degradation products. Proteins with a concentration of 10 mg/ml were dialyzed overnight at 4° C. against PBS with a broad range of pHs (3.5, 4.5, 5.5, 6.5, 7.0, 7.5 and 8.5). Control protein with the same concentration in standard buffer PBS (pH 6.5) was stored at −80° C. during the 2 weeks period. Determination of degradation bands by SDS-PAGE was done at t=0 and t=14d time points and soluble aggregates were assessed in the SEC-HPLC. Determination of remaining activity after 2 weeks at 40° C. was done using Biacore.

Example 1

Optimization of Anti-TNFα scFv Antibody, 34rFW1.4, to Reduce Aggregation

The 34rFW1.4 antibody shows a propensity for pH dependent aggregation in solution. The 578rFW1.4 antibody (see International Application WO2009155724), which shares the same framework structure as 34rFW1.4, does not show a propensity for aggregation. Homology models were generated to identify potential residues in the 34rFW1.4 that could be modified to reduce its aggregation propensity as follows.

Variable domain sequences were used to build homology models of the 34rFW1.4 antibody and the 578rFW1.4 antibody. To generate the models, BLAST algorithm-based searches were used to identify template structures for the light chain (VL) and heavy chain (VH) variable domain sequences for each antibody separately. BLOSUM80 (matrix for less divergent alignments) was used as the matrix for the alignments due to the high conservation of framework regions in antibodies. Individual templates for each chain (VL/VH) were selected that showed more than 70% identity to the query sequences.

The program MODELER of the Discovery Studio version 2.5.5 (DS 2.5.5) software (Accelrys, Inc., San Diego, Calif.) was used to generate 100 scFv models based on the identified variable domain templates. Alignment of the reference antibody sequences to be modelled with template structures were used as input data. 100 models containing all non-hydrogen atoms were generated. The best model structures were selected based on a PDF (Probability Density Function) physical energy score. Relative orientation of VH and VL domain was set to match the one from the variable domain template structure with the highest homology to both (VL and VH) sequences modelled. Alternate conformations in the model were removed, termini were added, and missing side-chain atoms were added. CHARMM forcefield was applied to the scFv models and submitted to 2000 cycles of energy minimization using a RMS Gradient of 0.01 and the Generalized Born with Molecular Volume (GBMV) as implicit solvent model.

Protein Ionization and residue pK calculations for each of the antibodies were conducted. The calculations were done using the protocol implementation included in Discovery Studio version 2.5.5 (DS 2.5.5), based on the theory developed by Bashford and Karplus, 1991. The results of protein ionization and residue pK calculations were compared for the two molecules in terms of $pK_{1/2}$ of the side chains and titration curves of each titratable residue, including Asp, Glu, Arg, Lys, His, Tyr, Cys, the N-terminal and C terminal residues of the antibodies.

CHARMM forcefield was applied to the scFv models and protonated at pH 7.4, titration curves and pKs of the individual residues were calculated from pH 2 to pH 14 range using pH steps of 0.2. Two conserved Lys residues at positions 47 and 50 in the light chain of the 578rFW1.4 antibody differed compared with the Lys at those positions in the 34rFW1.4 (see FIG. 1).

Introduction of Preferred Substitutions

The Discovery Studio software was used to conduct molecular dynamics simulations to predict mutations that improve the interaction affinity between VL and VH, thereby preventing the domains from falling apart and forming oligomers and or higher order aggregates. The stability of the VL/VH interface of the 34rFW1.4 antibody was estimated as energy terms as free energy G. A CHARMM protocol adaptation (also included in DS 2.5.5) was used to calculate the energy difference between the entire scFv heterodimer complex and the sum of the energies of each of the individual variable domains. The calculations were done in the context of an implicit solvent method using the Generalized Born with Molecular Volume integration (GBMV). The energies of both domains and the complex were calculated, and the output was determined as the difference in energy between the complex and the sum of the individual domains according to the following calculation: G interface=G(a)−G(b)−G(c), where G(a) is the energy of the antibody, G(b) is the energy of the VL, and G(c) is the energy of the VH.

Arginine (R) was selected as a possible residue substitution for the lysine (K) at positions 47 and 50, because the sidechain pKa value for R (12.5) is higher than pKa of K (10.5). Mutants K47R and K50R were generated by replacing K for R individually at the respective positions. 2000 cycles of energy minimization were performed for residues 10 Angstroms or closer to the area around the mutation to allow the new model molecules to adapt to the change. The implicit solvent model for these energy minimization rounds was GBMV. Predicted average delta G for the mutants was −94 kcal/mol. Therefore contribution of the mutations was estimated to be 4 kcal/mol compared to the parental anti-TNF scFv antibody.

Example 2

Stability Analysis of the Optimized 34rFW1.4 Antibody

K50R mutant and K47R mutant were generated in the 34rFW1.4 antibody (which is disclosed in co-pending International Application No. PCT/CH2009/000219, filed Jun. 25, 2009, the contents of which are hereby incorporated by reference in its entirety). Another mutant of 34rFW1.4 having additional substitutions to reduce its immunogenicity in vivo was prepared according to the methods described in U.S. patent application Ser. No. 12/973,968. In particular, the third mutant, designated 34rFW1.4_VLK50R_DHP, contained a serine (S) at heavy chain position 12 (AHo numbering), a threonine (T) at heavy chain position 103 (AHo numbering), and a threonine (T) at heavy chain position 144 (AHo numbering). Stability studies of the parent and mutant 34rFW1.4 antibodies were conducted under accelerated conditions as follows.

Figures 5A, 5B:
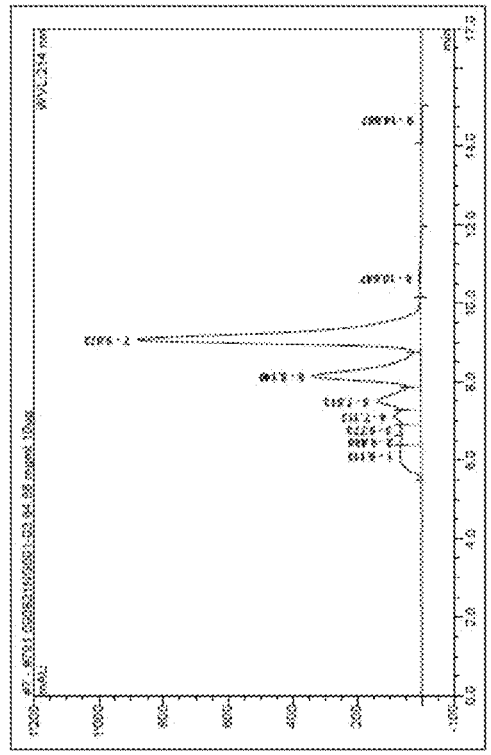
FIG. 5A shows stability of 34rFW1.4 under accelerated conditions determined by SE-HPLC analysis after 2 weeks incubation at 40° C. and using 60 mg/ml concentration.
FIG. 5B shows stability of 34rFW1.4_VL_K50R under accelerated conditions determined by SE-HPLC analysis after 2 weeks incubation at 40° C. and using 60 mg/ml concentration.
Figure 6B:
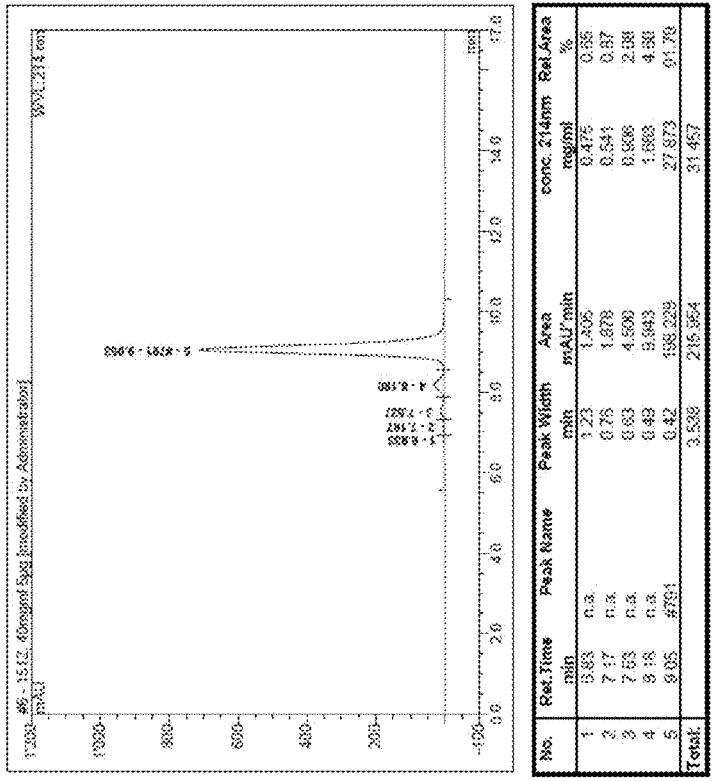
FIG. 6B shows stability of 34rFW1.4_VLK50R under accelerated conditions determined by SE-HPLC analysis after 2 weeks incubation at 40° C. and using 40 mg/ml concentration.
Figure 6A:
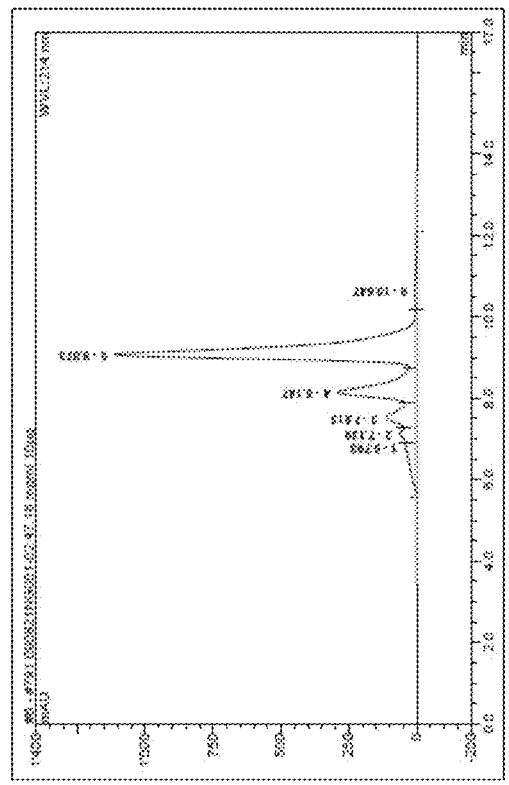
FIG. 6A shows stability of 34rFW1.4 under accelerated conditions determined by SE-HPLC analysis after 2 weeks incubation at 40° C. and using 40 mg/ml concentration.
Figure 8B:
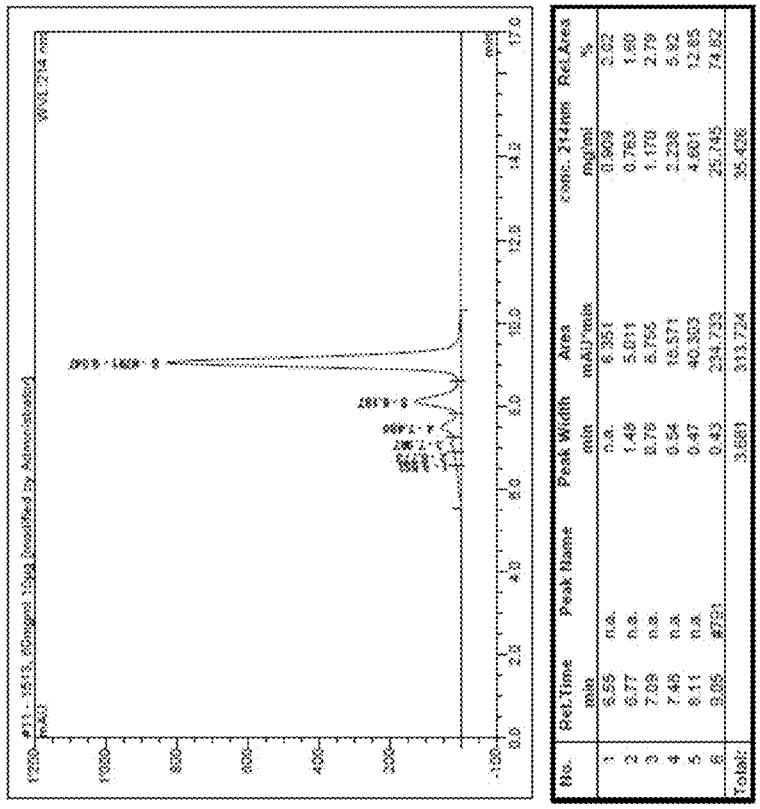
FIG. 8B shows stability of 34rFW1.4_K47R under accelerated conditions determined by SE-HPLC analysis after 2 weeks incubation at 40° C. and using 60 mg/ml concentration.
Figure 8A:
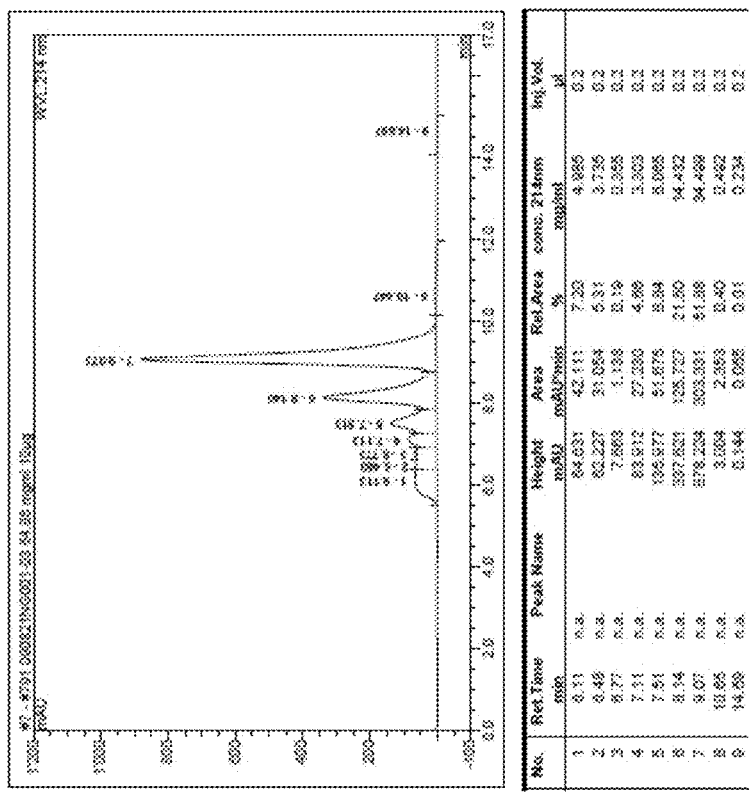
FIG. 8A shows stability of 34rFW1.4 under accelerated conditions determined by SE-HPLC analysis after 2 weeks incubation at 40° C. and using 60 mg/ml concentration.
Figure 9B:
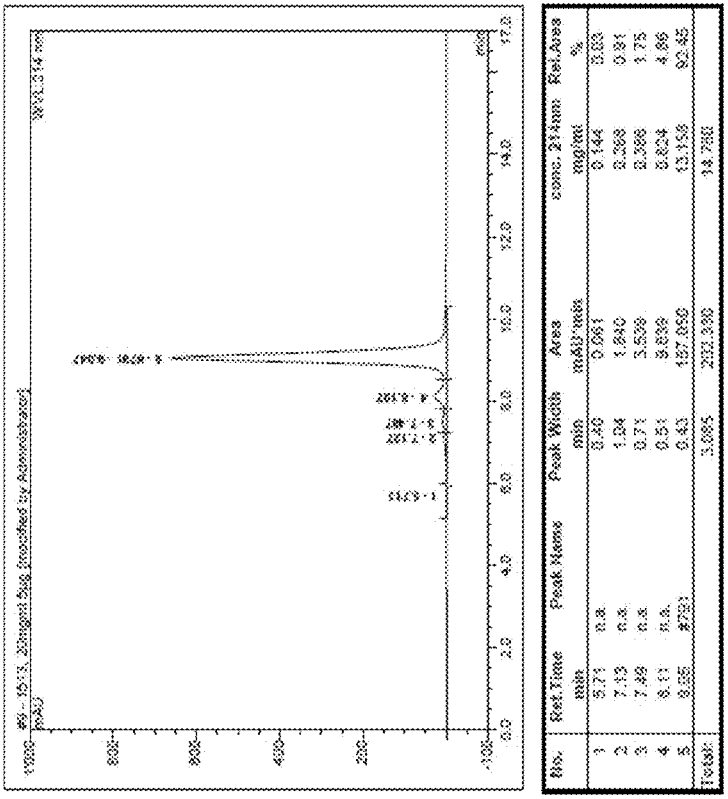
FIG. 9B shows stability of 34rFW1.4_K47R under accelerated conditions determined by SE-HPLC analysis after 2 weeks incubation at 40° C. and using 20 mg/ml concentration.
Figure 9A:
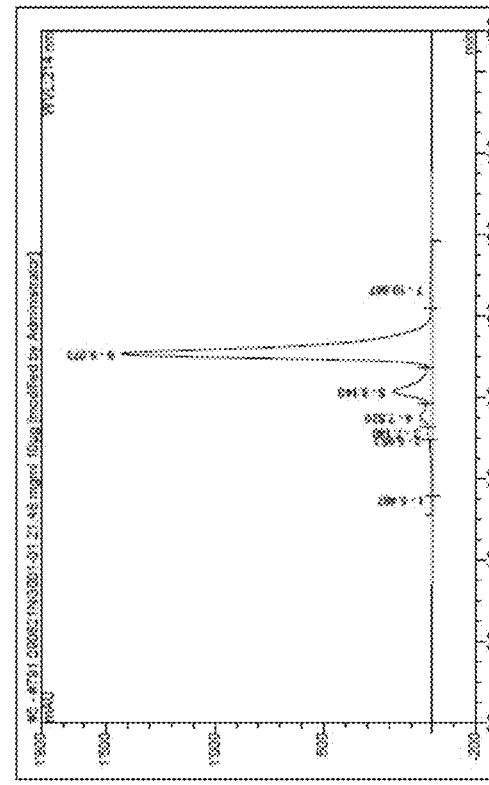
FIG. 9A shows stability of 34rFW1.4 under accelerated conditions determined by SE-HPLC analysis after 2 weeks incubation at 40° C. and using 20 mg/ml concentration.

The 34rFW1.4 antibody, mutant 34rFW1.4_VL_K50R, and 34rFW1.4_VLK50R_DHP were concentrated up to 20, 40 and 60 mg/mL in phosphate buffered saline (50 mM Na2HPO4, 150 mM NaCl, pH 6.5) formulation and incubated 2 weeks at 40° C. The 34rFW1.4 and 34rFW1.4_K47R antibodies were concentrated up to 20 and 60 mg/mL in phosphate buffered saline (50 mM Na2HPO4, 150 mM NaCl, pH 6.5) formulation and incubated 2 weeks at 40° C. Samples were analyzed before and after 14 days incubation for degradation using 12.5% sodium dodecyl sulfate-polyacrylamide gel electrophoresis (SDS-PAGE) under reducing and non-reducing conditions. Size-exclusion high-performance liquid chromatography (SE-HPLC) was used to determine monomer content and soluble aggregates of the samples before and after the incubation period. Monomers were resolved from non-monomeric species on a TSKgel Super SW2000 column (TOSOH Bioscience) and the percentage of monomeric protein was calculated as the area of the monomer peak divided by the total area of all product peaks. The results of the studies for 34rFW1.4 and 34rFW1.4_VLK50R_DHP are shown in FIGS. 2A-B, 3A-B, and 4A-B, respectively. The results for 34rFW1.4_VL_K50R are shown in FIGS. 5B, 6B, and 7B. These experiments demonstrated that 34rFW1.4_VLK50R_DHP had a reduced propensitiy for aggregation compared with 34rFW1.4. The mutant 34rFW1.4_K47R also demonstrated such a reduction as shown in FIGS. 8B and 9B.

In addition, the thermal stability and binding affinities of 34rFW1.4 and 34rFW1.4_VLK50R_DHP antibodies were compared. The results demonstrated that the mutations made to generate the 34rFW1.4_VLK50R_DHP antibody did not affect the stability or binding activity relative to the parent 34rFW1.4 antibody.

EQUIVALENTS

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the invention, and exclusive use of all modifications that come within the scope of the appended claims is reserved. It is intended that the present invention be limited only to the extent required by the appended claims and the applicable rules of law.

All literature and similar material cited in this application, including, patents, patent applications, articles, books, treatises, dissertations, web pages, figures and/or appendices, regardless of the format of such literature and similar materials, are expressly incorporated by reference in their entirety. In the event that one or more of the incorporated literature and similar materials differs from or contradicts this application, including defined terms, term usage, described techniques, or the like, this application controls.

The section headings used herein are for organizational purposes only and are not to be construed as limiting the subject matter described in any way.

While the present inventions have been described in conjunction with various embodiments and examples, it is not intended that the present teachings be limited to such embodiments or examples. On the contrary, the present inventions encompass various alternatives, modifications, and equivalents, as will be appreciated by those of skill in the art.

The claims should not be read as limited to the described order or elements unless stated to that effect. It should be understood that various changes in form and detail may be made without departing from the scope of the appended claims. Therefore, all embodiments that come within the scope and spirit of the following claims and equivalents thereto are claimed.

What is claimed is:

1. A method of blocking the function of TNFα in a subject, the method comprising administering to the subject a pharmaceutical composition comprising an antibody having the sequence of SEQ ID NO: 10, wherein the subject has uveitis, and wherein the pharmaceutical composition is administered topically to an eye of the subject.

2. The method of claim 1, wherein the pharmaceutical composition is administered in a single or divided dose comprising 0.1 to 100 mg of the antibody.

3. A method of reducing TNFα-mediated inflammation in a subject in need thereof, the method comprising administering to a subject a therapeutically effective amount of an antibody that comprises a variable light chain that has an Arginine at Aho position 50 and the sequence of SEQ ID NO: 2, and a variable heavy chain comprising the sequence of SEQ ID NO: 5, wherein the subject has uveitis, and wherein the pharmaceutical composition is administered topically to an eye of the subject.

4. The method of claim 3, wherein the therapeutically effective amount of the antibody is in a range of about 0.1 to 100 mg/kg of patient body weight.

5. The method of claim 3, wherein the antibody comprises the sequence of SEQ ID NO: 10.

* * * * *